(12) United States Patent
Haldar et al.

(10) Patent No.: US 9,028,842 B2
(45) Date of Patent: May 12, 2015

(54) COMPOSITIONS AND METHODS FOR TREATMENT, RESEARCH AND THERAPEUTIC APPLICATIONS FOR MALARIA

(71) Applicant: Northwestern University, Evanston (IL)

(72) Inventors: Kasturi Haldar, Chicago, IL (US); Pamela Tamez, Chicago, IL (US); Souvik Bhattacharjee, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/918,339

(22) Filed: Jun. 14, 2013

(65) Prior Publication Data

US 2013/0273086 A1   Oct. 17, 2013

Related U.S. Application Data

(62) Division of application No. 12/255,902, filed on Oct. 22, 2008, now Pat. No. 8,465,746.

(60) Provisional application No. 60/981,707, filed on Oct. 22, 2007.

(51) Int. Cl.
| | | |
|---|---|---|
| *A61K 39/015* | (2006.01) | |
| *A61K 38/00* | (2006.01) | |
| *A61K 39/00* | (2006.01) | |
| *G01N 33/569* | (2006.01) | |
| *A61K 9/00* | (2006.01) | |

(52) U.S. Cl.
CPC ........... *A61K 39/0005* (2013.01); *A61K 9/0019* (2013.01); *A61K 39/015* (2013.01); *G01N 33/56905* (2013.01); *G01N 2333/445* (2013.01); *A61K 38/00* (2013.01)

(58) Field of Classification Search
CPC ... A61K 38/00; A61K 39/005; A61K 39/015; A61K 9/0019
USPC .................... 424/185.1, 184.1, 268.1, 272.1; 530/326
See application file for complete search history.

(56) References Cited

PUBLICATIONS

Bozdech, Z. et al. "Expression profiling of the schizont and trophozoite stages of *Plasmodium falciparum* with a long-oligonucleotide microarray" 2003 Genome Biol 4, R9.
Cooke et al. "A Maurer's cleft-associated protein is essential for expression of the major malaria virulence antigen on the surface of infected red blood cells" 2006 J Cell Biol 172, 899-908.
Craig et al., "Molecules on the surface of the *Plasmodium falciparum* infected erythrocyte and their role in malaria pathogenesis and immune evasion" 2001 Mol Biochem Parasitol 115, 129-43.
Desai et al., "A voltage-dependent channel involved in nutrient uptake by red blood cells infected with the malaria parasite" 2000 Nature 406, 1001-1005.
Dzikowski et al., "Mutually exclusive expression of virulence genes by malaria parasites is regulated independently of antigen production" 2006 PLoS Pathog 2, e22.
Gardner, M.J. et al. "Genome sequence of the human malaria parasite *Plasmodium Falciparum*" 2002 Nature 419, 498-511.
Haldar et al., "Malaria: Mechanisms of Erythrocytic Infection and Pathological Correlates of Severe Disease" 2007 Annual Review of Pathology: Mechanisms of Disease 2, 217-249.
Hiller et al., "A host-targeting signal in virulence proteins reveals a secretome in malarial infection" 2004 Science 306, 1934-7.
Hiller et al., "Identification of a stomatin orthologue in vacuoles induced in human erythrocytes by malaria parasites: A role for microbial raft-proteins in apicomplexan vacuole biogenesis" 2003 J Biol Chem, 48413-48421.
Jeffares et al., "Genome variation and evolution of the malaria parasite *Plasmodium falciparum*" 2007 Nat Genet 39, 120-5.
Lauer et al., "A membrane network for nutrient import in red cells infected with the malaria parasite" 1997 Science 276, 1122-5.
Lauer et al., "Sphingolipid synthesis as a target for chemotherapy against malaria parasites" 1995 Proc Natl Acad Sci U S A 92, 9181-5.
Lauer, S. et al. "Vacuolar uptake of host components, and a role of cholesterol and sphingomyelin in malarial infection" 2000 Embo J 19, 3556-64.
Marti et al., "Targeting malaria virulence and remodeling proteins to the host erythrocyte" 2004 Science 306, 1930-3.
Mehlin et al., "Heterologous expression of proteins from *Plasmodium falciparum*: results from 1000 genes" 2006 Mol Biochem Parasitol 148, 144-60.
Miller et al., "The pathogenic basis of Malaria" 2002 Nature 415, 673-9.
Mu et al., "Genome-wide variation and identification of vaccine targets in the *Plasmodium falciparum* genome" 2007 Nat Genet 39, 126-30.
Murphy et al. "Erythrocyte G protein as a novel target for malarial Chemotherapy" 2006 PLoS Med 3, e528.
Pei et al. "The ring-infected erythrocyte surface antigen (RESA) of *Plasmodium falciparum* stabilizes spectrin tetramers and suppresses further Invasion" 2007 Blood 110, 1036-42.
Pleass et al., "Opinion: antibody-based therapies for malaria" 2005 Nat Rev Microbiol 3, 893-9.
Rasti et al., "Molecular aspects of malaria pathogenesis" 2004 FEMS Immunol Med Microbiol 41, 9-26.
Sargeant et al. "Lineage-specific expansion of proteins exported to erythrocytes in malaria parasites" 2006 Genome Biol 7, R12.
Volkman et al., "A genome-wide map of diversity in *Plasmodium falciparum*" 2007 Nat Genet 39, 113-9.
Voss et al. "A var gene promoter controls allelic exclusion of virulence genes in *Plasmodium falciparum* malaria" 2006 Nature 439, 1004-8.

*Primary Examiner* — Padma V Baskar
(74) *Attorney, Agent, or Firm* — Casimir Jones S.C.

(57) ABSTRACT

The present invention provides anti-*Plasmodium* immunogenic compositions comprising EVP1 (PFD0495c) or an antigenic portion thereof, as well as methods of immunizing against malaria employing these compositions. In other embodiments, the present invention provides methods of identifying *Plasmodium* infection employing agents that bind to EVP1 or an antibody generated thereto.

3 Claims, 24 Drawing Sheets

FIG. 1C

PFD0495c

SS | REPEAT | TM

HT | Cterm

| Strain | Repeat* # |
|---|---|
| P.falciparum (PFD0495c) | |
| 3D7 Lab | 21 |
| 3D7 PDB* | 17 |
| HB3 | 21 |
| Dd2 | 25 |
| Ghanian | 19 |

*{DD(E/V/K/N)V(S/R/H/N)(N/H)(I/T)(N/K)}

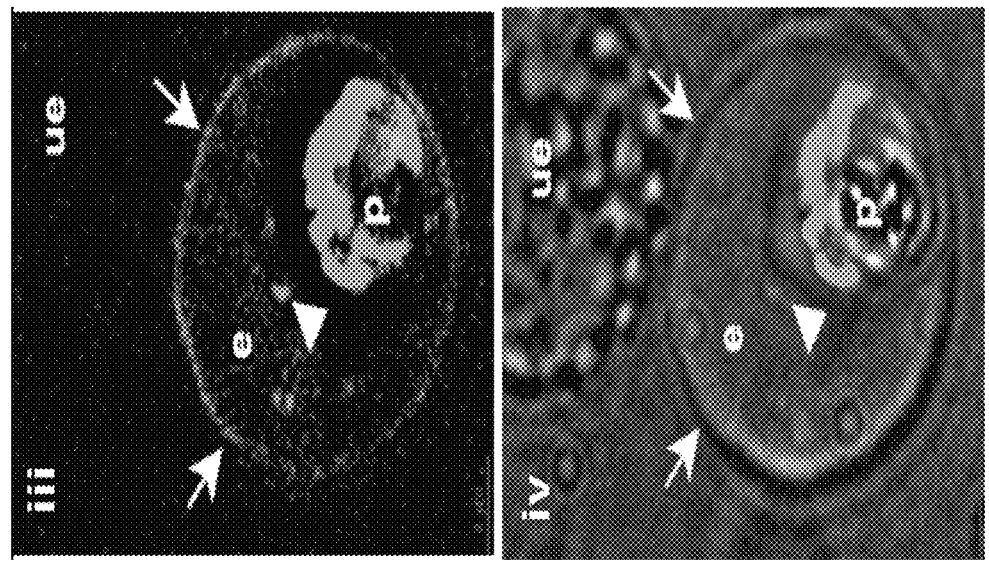
FIG. 2A
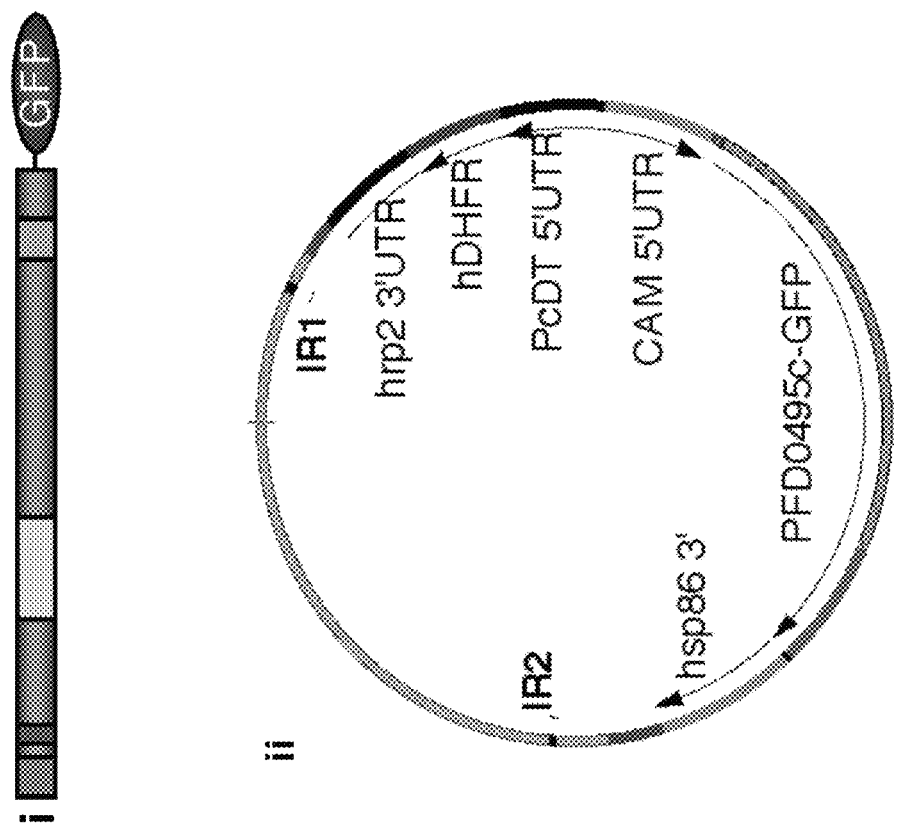

FIG. 4

| Step # | | Days Completed |
|---|---|---|
| 1. | Genome scanning/in silico input for candidate genes | |
| 2. | Expression of transgenes integrated into the chromosome | 14 |
| 3. | Topology studies to identify cytoplasmic domains of parasite proteins detected in the erythrocyte. | 3 |
| 4. | Expression and delivery of GST-fusion into resealed erythrocyte ghosts and consequences for *P. falciparum* invasion and/or intracellular growth | 14 |
| 5. | Characterization of resealed infected ghosts and transgenic parasite lines for intraerythrocytic function. | 30-60 |

FIG. 6B

| P. falciparum gene |
|---|
| PF10_0177 |
| PF13_0317 |
| PFA0210c |
| PFC0435w |
| PFD0495c |
| PFL0600w |
| PFL1660c |
| PFC0555c |
| PF13_0090 |

FIG. 7
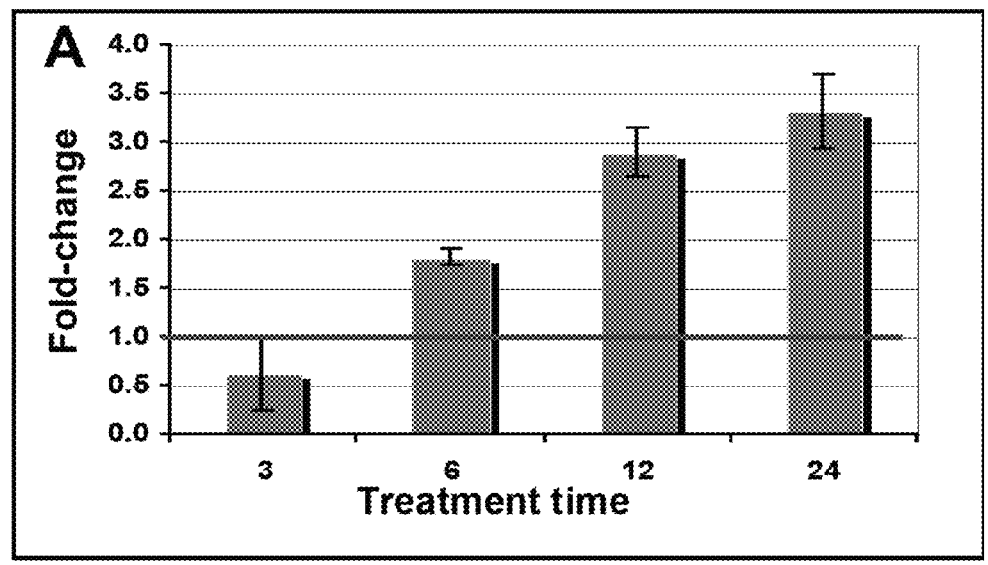
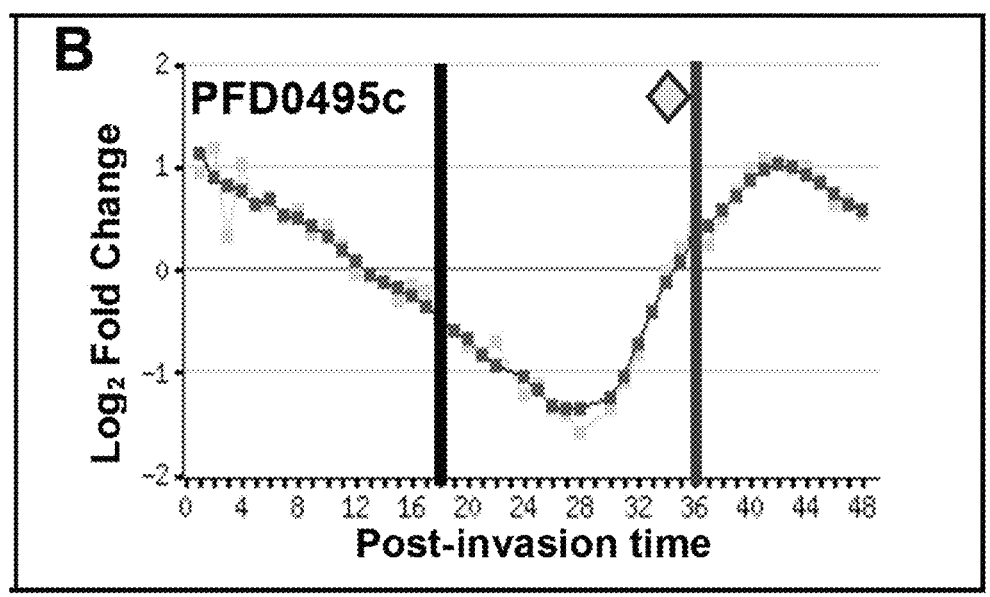

FIG. 8

PFD0495c

▓▓▓▓▓▓▓▓▓▓▓▓▓▓YIIKNDHLNSEQS▓▓▓▓▓▓▓▓▓▓▓TKKNEFFLGESILGATSS
RSTSLNIEQNKNTNIIKDKNEQSYDEHIVMNPNTNRALSINTVFNYNKENKEKKIFSFSE
FPKEFNILDVVWPYMKQPKELFKKSSVITFLMDHYFRHELYILESRIAMKPRRRTYEAPC
FEHDDFELERDFFFLEDCDEDHQFFNKYKSYFFSLNVLDHCKSLRTKKQKCNNMKDDEVS
NIN▓▓▓▓▓▓▓▓DDEVSNIN▓▓▓▓▓▓▓▓DDVVRNIN▓▓▓▓▓▓▓DDEVHHTN▓▓▓▓▓▓▓D
DKVNHTN▓▓▓▓▓▓▓DDKVNHTN▓▓▓▓▓▓▓DDNVNHTN▓▓▓▓▓▓▓DDKVNHTN▓▓▓▓▓
▓▓DDKVNHTNNYYNDKKNNAGDIKTNNSIREEKKLEHPDRNIEKKIDLITYNKKRIEEY
YDSIISYFFGLIILYHNKKETNLNYYTKFLTLDKYKNMYNCLNNDISKIYEKAILFSHEE
FCIIQKKDLKPHGLRGNIKYYYFFNRIVSTSLYLLHEILQKLDGKMYTFQKLPLKIQNHL
INLPDIRIKEIKKRMRQQKKKNQNSLLESSSYKDLYYVSSEYYDYVSKCLIWSNYYFFNY
MSTTIVYSVKKRSYEYIQKEKSKINLFLEYAHNDIIEYIKDITYYFKLIVNKIESKRLFS
EPVMLCFQLFSDHYLYLLKNILSILLIHIEKPVTRKSNRDLKKIFNCIKDQENITKNILD
EFHSKNKIRYNPTEFLIYKFFSSIQYKQNIAHKYIIQSNINIISLMLKIFN▓▓▓▓▓▓▓
▓▓▓▓▓▓▓▓▓▓▓▓DLDIDDTLKFQHDQEFLNYFKRYQDFNNQLFDSFRSDDR

FIG. 9A

```
HB3_PFD0495c       YIIKNDHLNSEQSSFSRIIAEYCDTKKNEFFLGESILGATSS  60
PDB_PFD0495c       YIIKNDHLNSEQSSFSRIIAEYCDTKKNEFFLGESILGATSS  60
Ghanaian_PFD0495c  YIIKNDHLNSEQSSFSRIIAEYCDTKKNEFFLGESILGATSS  60
Lab_3D7_PFD0495c   YIIKNDHLNSEQSSFSRIIAEYCDTKKNEFFLGESILGATSS  60
Dd2_PFD0495c       YIIKNDHLNSEQSSFSRIIAEYCDTKKNEFFLGESILGATSS  60
                                ****************************************

HB3_PFD0495c       RSTSLNIEQNKNTNIIKDKNEQSYDEHIVMNPNTNRALSINTVFNYNKENKEKKIFSFSE  120
PDB_PFD0495c       RSTSLNIEQNKNTNIIKDKNEQSYDEHIVMNPNTNRALSINTVFNYNKENKEKKIFSFSE  120
Ghanaian_PFD0495c  RSTSLNIEQNKNTNIIKDKNEQSYDEHIVMNPNTNRALSINTVFNYNKENKEKKIFSFSE  120
Lab_3D7_PFD0495c   RSTSLNIEQNKNTNIIKDKNEQSYDEHIVMNPNTNRALSINTVFNYNKENKEKKIFSFSE  120
Dd2_PFD0495c       RSTSLNIEQNKNTNIIKDKNEQSYDEHIVMNPNTNRALSINTVFNYNKENKEKKIFSFSE  120
                   ************************************************************

HB3_PFD0495c       FPKEFNILDVVWPYMKQPKELFKKSSVITFLMDHYFRHELYILESRIAMKPRRRTYEAPC  180
PDB_PFD0495c       FPKEFNILDVVWPYMKQPKELFKKSSVITFLMDHYFRHELYILESRIAMKPRRRTYEAPC  180
Ghanaian_PFD0495c  FPKEFNILDVVWPYMKQPKELFKKSSVITFLMDHYFRHELYILESRIAMKPRRRTYEAPC  180
Lab_3D7_PFD0495c   FPKEFNILDVVWPYMKQPKELFKKSSVITFLMDHYFRHELYILESRIAMKPRRRTYEAPC  180
Dd2_PFD0495c       FPKEFNILDVVWPYMKQPKELFKKSSVITFLMDHYFRHELYILESRIAMKPRRRTYEAPC  180
                   ************************************************************

HB3_PFD0495c       FEHDDFELERDFFFLEDCDEDHQFFNKYKSYFFSLNVLDHCKSLRTKKQKCNNMKDDEVS  240
PDB_PFD0495c       FEHDDFELERDFFFLEDCDEDHQFFNKYKSYFFSLNVLDHCKSLRTKKQKCNNMKDDEVS  240
Ghanaian_PFD0495c  FEHDDFELERDFFFLEDCDEDHQFFNKYKSYFFSLNVLDHCKSLRTKKQKCNNMKDDEVS  240
Lab_3D7_PFD0495c   FEHDDFELERDFFFLEDCDEDHQFFNKYKSYFFSLNVLDHCKSLRTKKQKCNNMKDDEVS  240
Dd2_PFD0495c       FEHDDFELERDFFFLEDCDEDHQFFNKYKSYFFSLNVLDHCKSLRTKKQKCNNMKDDEVS  240
                   ************************************************************

HB3_PFD0495c       NIN        DDEVSNIN        DDVVRNIN        D  300
PDB_PFD0495c       NIN        DDEVSNIN        DDVVR---        D  292
Ghanaian_PFD0495c  NIS        DDEVSNIK        DDVVRNIN        DDVVRNIN        D  300
Lab_3D7_PFD0495c   NIN        DDEVSNIK        DDVVRNIN        DDEVHHTN        D  300
Dd2_PFD0495c       NIN        DDEVSNIK        DDVVRNIN        DDEVHHTN        D  300
                   **.*******.*******.**  *  **.****   ::  *****  *::  ***.*.****

HB3_PFD0495c       DNVNHTN        DDKVNHTN        DDKVNHTN  ---------------  341
PDB_PFD0495c       DKVNHTN        DDKVNHTN        DDKVNHTN  ---------------  333
Ghanaian_PFD0495c  DNVNHTN        DDKVNHTN        DDKVNHTN  ---------------  341
Lab_3D7_PFD0495c   DKVNHTN        DDKVNHTN        DDKVNHTN  ---------------  341
Dd2_PFD0495c       DKVNHTN        DDKVNHTN        DDKVNHTN        DDKVNHTN  360
                   *.*******************.***************  :          :          :

HB3_PFD0495c       ---------------        DDKVNHTN        DDKVNHTN        DDKVNHTN  388
PDB_PFD0495c       ---------------        DDKVNHTN        DDKVNHTN        DDKVNHTN  371
Ghanaian_PFD0495c  ---------------        DDKVNHTN        DDKVNHTN        DDKVNHTN  387
Lab_3D7_PFD0495c   ---------------        DDKVNHTN        DDKVNHTN        DDKVNHTN  388
Dd2_PFD0495c       DDNVNHTN        DDKVNHTN        DDKVNHTN        DDKVNHTN  420
                          :      :*********************:*****   ;
```

FIG. 9B

```
HB3_PFD0495c       ▓▓▓▓▓DDKVNHTNNYYNDKKNNAGDIKTNNSIREEKKLEHPDRNIEKKIDLITYNKKR 448
PDB_PFD0495c       ▓▓▓▓▓-------NYYNDKKNNAGDIKTNNSIREEKKLEHPDRNIEKKIDLITYNKKR 416
Ghanaian_PFD0495c  ▓▓▓▓▓-------NYYNDKKNNAGDIKTNNSIREEKKLEHPDRNIEKKIDLITYNKKR 432
Lab_3D7_PFD0495c   ▓▓▓▓▓DDKVNHTNNYYNDKKNNAGDIKTNNSIREEKKLEHPDRNIEKKIDLITYNKKR 448
Dd2_PFD0495c       ▓▓▓▓▓DDKVNHTNNYYNDKKNNAGDIKTNNSIREEKKLEHPDRNIEKE-DRFNYIKKD 479
                        :              *************************:  *  .* **

HB3_PFD0495c       IEEYYDSIISYFFGLIILYHNKKETNLNYYTKFLTLDKYKNMYNCLNNDISKIYEKAILF 508
PDB_PFD0495c       IEEYYDSIISYFFGLIILYHNKKETNLNYYTKFLTLDKYKNMYNCLNNDISKIYEKAILF 476
Ghanaian_PFD0495c  IEEYYDSIISYFFGLIILYHNKKETNLNYYTKFLTLDKYKNMYNCLNNDISKIYEKAILF 492
Lab_3D7_PFD0495c   IEEYYDSIISYFFGLIILYHNKKETNLNYYTKFLTLDKYKNMYNCLNNDISKIYEKAILF 508
Dd2_PFD0495c       RRILQYNFIFFRINNIIS----KETNLNYYTKLLTLDKYKNMYNCLNNDISKIYEKAILF 535
                     .:* : :.  **        ************:***************************

HB3_PFD0495c       SHEEFCIIQKKDLKPHGLRGNIKYYYFFNRIVSTSLYLLHEILQKLDGKMYTFQKLPLKI 568
PDB_PFD0495c       SHEEFCIIQKKDLKPHGLRGNIKYYYFFNRIVSTSLYLLHEILQKLDGKMYTFQKLPLKI 536
Ghanaian_PFD0495c  SHEEFCIIQKKDLKPHGLRGNIKYYYFFNRIVSTSLYLLHEILQKLDGKMYTFQKLPLKI 552
Lab_3D7_PFD0495c   SHEEFCIIQKKDLKPHGLRGNIKYYYFFNRIVSTSLYLLHEILQKLDGKMYTFQKLPLKI 568
Dd2_PFD0495c       FTRVLYIQKK--IKSSWIESQYKILLFFS---YCHIFIPVTNITKIRWTDVYLSEITIKD 590
                      :* :*  :*.  :..: * **.    :::   : *:  .  .:.:.:*

HB3_PFD0495c       QNHLINLPDIRIKEIKKRMRQQKKKNQNSLLESSSYKDLYYVSSEYYDYVSKCLIWSNYY 628
PDB_PFD0495c       QNHLINLPDIRIKEIKKRMRQQKKKNQNSLLESSSYKDLYYVSSEYYDYVSKCLIWSNYY 596
Ghanaian_PFD0495c  QNHLINLPDIRIKEIKKRMRQQKKKNQNSLLESSSYKDLYYVSSEYYDYVSKCLIWSNYY 612
Lab_3D7_PFD0495c   QNHLINLPDIRIKEIKKRMRQQKKKNKNSLLESSSYKDLYYVSSEYYDYVSKCLIWSNYY 628
Dd2_PFD0495c       TESFN---SSGYKNQENKTYETTEKKENSLLESSSYKDLYYVSSEYYDYVSKCLIWSNYY 647
                    :  ::::    .  *:.:::   : .:*:;*****************************

HB3_PFD0495c       FFNYMSTTIVYSVKKRSYEYIQKEKSKINLFLEYAHNDIIEYIKDITYYFKLIVNKIESK 688
PDB_PFD0495c       FFNYMSTTIVYSVKKRSYEYIQKEKSKINLFLEYAHNDIIEYIKDITYYFKLIVNKIESK 656
Ghanaian_PFD0495c  FFNYMSTTIVYSVKKRSYEYIQKEKSKINLFLEYAHNDIIEYIKDITYYFKLIVNKIESK 672
Lab_3D7_PFD0495c   FFNYMSTTIVYSVKKRSYEYIQKEKSKINLFLEYAHNDIIEYIKDITYYFKLIVNKIESK 688
Dd2_PFD0495c       FFNYMSTTIVYSVKKRSYEYIEKEKSKINLFLEYAHNDIIEYIKDITYYFKLIVNKIESK 707
                   *********************:**************************************

HB3_PFD0495c       RLFSEPVMLCFQLFSDHYLYLLKNILSILLIHIEKPVTRKSNRDLKKIFNCIKDQENITK 748
PDB_PFD0495c       RLFSEPVMLCFQLFSDHYLYLLKNILSILLIHIEKPVTRKSNRDLKKIFNCIKDQENITK 716
Ghanaian_PFD0495c  RLFSEPVMLCFQLFSDHYLYLLKNILSILLIHIEKPVTRKSNRDLKKIFNCIKDQENITK 732
Lab_3D7_PFD0495c   RLFSEPVMLCFQLFSDHYLYLLKNILSILLIHIEKPVTRKSNRDLKKIFNCIKDQENITK 748
Dd2_PFD0495c       RLFSEPVMLCFQLFSDHYLYLLKNILSILLIHIEKPVTRKSNRDLKKIFNCIKDQENITK 767
                   ************************************************************

HB3_PFD0495c       NILDEFHSKNKIRYNPTEFLIYKFFSSIQYKQNIAHKYIIQSNINIISLMLKIFN▓▓▓▓▓ 808
PDB_PFD0495c       NILDEFHSKNKIRYNPTEFLIYKFFSSIQYKQNIAHKYIIQSNINIISLMLKIFN▓▓▓▓▓ 776
Ghanaian_PFD0495c  NILDEFHSKNKIRYNPTEFLIYKFFSSIQYKQNIAHKYIIQSNINIISLMLKIFN▓▓▓▓▓ 792
Lab_3D7_PFD0495c   NILDEFHSKNKIRYNPTEFLIYKFFSSIQYKQNIAHKYIIQSNINIISLMLKIFN▓▓▓▓▓ 808
Dd2_PFD0495c       NILDEFHSKNKIRYNPTEFLIYKFFSSIQYKQNIAHKYIIQSNINIISLMLKIFN▓▓▓▓▓ 827
```

FIG. 15

SEQ ID NO:41 (Accession No.: XM_001351379.1)

Plasmodium falciparum 3D7 protein

```
ATGTATAAGAAATGTTTCATTTTATATCCTATCTTTTTTCCCTCCTTATATATTTATATTATTAAGAATG
ATCATTTGAACTCAGAACAAAGTTCATTCTCAAGAATAATAGCAGAATACTGTGATACAAAAAAAATGA
ATTTTTTTTGGGGGAATCTATTTTAGGTGCTACATCCTCAAGAAGCACTTCTCTTAACATAGAACAGAAT
AAAAACACAAATATTATTAAAGATAAGAATGAACAAAGTTATGATGAACATATTGTAATGAATCCAAATA
CCAATCGAGCTCTTTCCATAAATACTGTATTCAATTACAATAAAGAAAATAAGGAAAAAAAATTTTTTC
CTTCTCCGAATTTCCAAAGGAATTTAATATACTTGATGTTGTTTGGCCATACATGAAACAACCTAAAGAA
CTTTTTAAAAAATCATCTGTAATCACTTTTTTAATGGACCATTATTTTAGACATGAACTATATATTTTAG
AAAGTAGAATTGCAATGAAACCAAGAAGGAGAACATATGAAGCTCCATGTTTTGAACATGATGATTTTGA
ATTAGAAAGAGATTTTTTTTTTTTAGAAGACTGTGATGAAGATCATCAATTTTTTAATAAATACAAAAGT
TATTTTTTTTCGTTGAATGTACTAGATCATTGTAAAAGTTTAAGGACTAAGAAGCAGAAATGTAATAATA
TGAAGGATGATGAGGTGAGCAATATTAACGATGATGAAGTGAGCAATATTAACGATGATGAAGTGAGCAA
TATTAACGATGATGAAGTGAGCAATATAAAAGATGATGTGGTGAGAAATATTAACGATGATGTGGTGAGA
AATATTAACGATGATGAGGTGCACCATACAAATGATGATAAGGTGAACCATACAAATGATGATAAGGTGA
ACCATACGAATGATGATAAGGTGAACCATACGAATGATGATAAGGTGAACCATACAAATGATGATAAGGT
GAACCATACAAATGACGATAATGTGAACCATACAAATGATGATAAGGTGAACCATACAAATGACGATAAG
GTGAACCATACAAATGACGATAAGGTGAACCATACAAATGACGATAAGGTGAACCATACAAATAATTATT
ATAATGATAAAAGAATAATGCAGGTGATATAAAAACTAATAATAGTATACGTGAGGAAAAAAAACTAGA
GCACCCGGACAGGAACATTGAAAAGAAGATCGATTTAATTACATATAATAAAAAAAGGATAGAAGAATAT
TATGACAGTATAATTTCATATTTTTCGGATTAATAATATTATATCATAATAAAAAAGAGACGAATCTAA
ATTATTACACAAAATTTTTAACATTAGATAAATATAAGAATATGTATAATTGTTTAAATAATGATATATC
TAAAATATATGAAAAAGCAATATTATTTTCACATGAAGAGTTTTGTATAATACAGAAAAAAGATTTAAAA
CCTCATGGTTTGAGAGGTAATATAAAATATTATTATTTTTTAATCGTATTGTTAGCACATCTTTATATT
TGTTACATGAAATATTACAAAAATTAGATGGAAAGATGTATACCTTTCAGAAATTACCATTAAAGATACA
GAATCATTTAATTAATCTTCCGGATATAAGAATCAAGGAAATTAAAAAACGTATGAGACAACAGAAAAAA
AAGAATCAAAATTCTCTTTTAGAAAGTAGTAGTTATAAAGATTTATATTATGTATCTAGTGAATATTATG
ATTATGTTAGTAAGTGTTTAATATGGTCTAATTATTATTTTTTAATTATATGTCTACCACTATAGTATA
TAGTGTTAAAAAAAGAAGCTATGAATATATACAAAAAGAAAAATCCAAAATAAATTTATTTTTAGAATAT
GCACATAATGATATTATAGAATATATAAAAGACATAACATATTATTTAAATTAATTGTTAATAAAATAG
AATCAAAACGCTTATTCTCTGAACCCGTAATGTTATGCTTTCAACTGTTTTCTGATCATTATTTATATTT
ACTCAAAAATATATTATCTATACTTTTAATACATATAGAAAAACCAGTTACAAGAAAATCAAACAGAGAT
CTAAAAAAATATTTAATTGTATAAAAGATCAAGAAAATATAACCAAAAATATTTTAGATGAATTCCATT
CCAAAAATAAAATTAGATATAATCCAACCGAATTCCTCATATATAAATTTTTTCAAGTATACAATATAA
ACAAAATATAGCACATAAATATATAATACAAAGTAATATTAATATTATATCCTTGATGTTGAAAATTTTT
AATTATTTTCATATACTTGTTATCTCATTAATCTTTTATCTAAACCTTCATTCTATGTATACTCTATTTA
TTGATTTAGATATTGATGATACTTTAAAGTTTCAGCATGATCAAGAGTTCTTAAATTATTTTAAAAGATA
TCAGGATTTTAATAATCAACTCTTTGATTCCTTCCGTTCCGACGACAGATGA
```

US 9,028,842 B2

COMPOSITIONS AND METHODS FOR TREATMENT, RESEARCH AND THERAPEUTIC APPLICATIONS FOR MALARIA

The present application is a divisional of U.S. patent application Ser. No. 12/255,902, filed Oct. 22, 2008, now U.S. Pat. No. 8,465,746, which claims priority to U.S. Provisional Application Ser. No. 60/981,707 filed Oct. 22, 2007, each of which is herein incorporated by reference in its entirety.

STATEMENT REGARDING FEDERAL FUNDING

This invention was made with government support under grant numbers AI007476, AI039071, HL069630, and HL078826 awarded by the National Institutes of Health. The government has certain rights in the invention.

FIELD OF THE INVENTION

The present invention provides anti-Plasmodium compositions comprising EVP1 (PFD0495c) or an antigenic portion thereof, as well as methods of immunizing against malaria employing these compositions. In other embodiments, the present invention provides methods of identifying *Plasmodium* infection employing agents that bind to EVP1 or an antibody generated thereto.

BACKGROUND

The most virulent of human malaria parasites *Plasmodium falciparum* kills approximately 2 million people worldwide, most of whom are children under five. In addition to its high mortality, malaria causes economic losses in adults who are unable to work because of repeated cycles of acute infection. The disease is now a well accepted cause of poverty in Africa. There are no effective vaccines against malaria and constant need for new drugs due to emergence of resistance of existing drugs. As such, what is needed are novel treatments and therapies for malaria.

The blood stage parasites that cause all of the symptoms and pathologies of malaria infect and remodel mature erythrocytes. Several hundred parasite proteins exported to the erythrocyte presumably underlie these remodeling events, but unfortunately most encode for 'hypothetical' proteins of unknown function. Those essential for parasitization of the erythrocyte cannot be identified in genetic knock outs. Parasite proteins such as PfEMP1 that have previously been shown to be present at the erythrocyte surface undergo rapid antigenic variation, and the diversity of the encoding var genes enables the parasite to avoid host defense.

As such, what is needed are compositions and methods for immunizing subjects against *Plasmodium* infection to prevent malaria, as well as methods for detecting *Plasmodium* infection.

SUMMARY OF THE INVENTION

The present invention provides anti-Plasmodium compositions comprising EVP1 or an antigenic portion thereof, as well as methods of immunizing against malaria employing these compositions. In other embodiments, the present invention provides methods of identifying *Plasmodium* infection employing agents that bind to EVP1 or an antibody generated thereto.

In some embodiments, the present invention provides compositions and methods for transgenic and cellular assays to use in combination with microarray and bioinformatics analyses to identify proteins known to be required for intracellular growth. In the present case, the protein is exported to the infected erythrocyte membrane, is critical in an essential, tubovesicular-import pathway, and contains a variant repeat region recognized by immune serum. These studies reveal the first parasite antigen unambiguously determined to be at the infected-erythrocyte surface and encoded by a single copy gene conserved across *Plasmodium* species. This protein, which was known as PFD0495c, is therefore termed "Conserved Erythrocyte Surface Protein" (CESP1), or "Conserved Erythrocyte Surface Antigen 1" (CESA1), or it can be referred to as "Erythrocyte Vesicle Protein 1" (EVP1) and is a target for vaccine and drug therapies. EVP1 is the preferred nomenclature as this protein defines a vesicular membrane compartment in the infected host cells.

Current vaccine targets based on conserved malaria parasite antigens are localized on the surface of sporozoites (that infect liver cells) or merozoites (that infect erythrocytes). Targeting the sporozoite does not directly block blood stage infection. Merozoites must invade erythrocytes in minutes. Thus, antibodies that block merozoite invasion must act extremely rapidly. In contrast EVP1 (CESP1) is on the surface of the infected erythrocyte for hours and thus antibodies blocking EVP1 (CESP1) function are contemplated to act on their target.

As such, the present invention further provides compositions and methods useful as vaccines and for inducing immune responses against malarial infection in vivo in a subject. Compositions and methods of the present invention therefore provide for treatment, research, therapeutic applications with regards to parasitic diseases such as malaria.

In some embodiments, the present invention provides compositions suitable for injection into a subject comprising: i) an adjuvant and/or physiological tolerable buffer, and ii) an isolated protein comprising Erythrocyte Vesicle Protein 1 (EVP1) or an antigenic portion thereof. In certain embodiments, the isolated protein comprises SEQ ID NOs:1-6 or an antigenic portion thereof, or SEQ ID NOs:7-28. In further embodiments, the isolated protein consists of SEQ ID NOs:1-6 or antigenic portion thereof, or SEQ ID NOs:7-28. In particular embodiments, the isolated protein is conjugated to a hapten or other immune stimulating moiety.

In certain embodiments, the present invention provides methods of vaccinating a person against *Plasmodium* infection, comprising: administering a composition to a subject comprising an isolated protein comprising Erythrocyte Vesicle Protein 1 (EVP1) or an antigenic portion thereof. In particular embodiments, the present invention provides methods for eliciting an immune response in a subject, comprising: administering a composition to a subject such that said subject manifests an immune response, wherein said composition comprises Erythrocyte Vesicle Protein 1 (EVP1) or an antigenic portion thereof. In some embodiments, the isolated protein comprises SEQ ID NOs:1-6 or an antigenic portion thereof, or SEQ ID NOs:7-28. In further embodiments, the isolated protein consists of SEQ ID NOs:1-6 or antigenic portion thereof, or SEQ ID NOs:7-28. In certain embodiments, the isolated protein is conjugated to a hapten or other immune stimulating moiety. In particular embodiments, the composition further comprises an adjuvant and/or physiological tolerable buffer. In other embodiments, the subject is a human or a domesticated animal, or a bird reptile, or rodent. In additional embodiments, the *Plasmodium* infection is *Plasmodium falciparum* infection. In other embodiments, the

*Plasmodium* species is selected from those that infection humans, including: *Plasmodium falciparum* (the cause of malignant tertian malaria); *Plasmodium vivax* (the most frequent cause of benign tertian malaria); *Plasmodium ovale* (the other, less frequent, cause of benign tertian malaria); *Plasmodium malariae* (the cause of benign quartan malaria); *Plasmodium knowlesi; Plasmodium brasilianum; Plasmodium cynomolgi; Plasmodium cynomolgi bastianellii; Plasmodium inui; Plasmodium rhodiani; Plasmodium schweitzi; Plasmodium semiovale;* and *Plasmodium simium.*

In certain embodiments, the present invention provides methods of detecting *Plasmodium* bacteria in a sample comprising: contacting a sample with an antibody or other agent configured to bind Erythrocyte Vesicle Protein 1 (EVP1) or an antibody thereto. In particular embodiments, the contacting is performed with the antibody or a fragment of the antibody. In further embodiments, the *Plasmodium* is *Plasmodium falciparum*. In other embodiments, the present invention provides methods of detecting *Plasmodium* bacteria in a sample comprising: contacting a sample with a nucleic acid sequence or nucleic acid sequences configured to detect EVP1 DNA or RNA. In other embodiments, the nucleic acid sequence is at least a portion of SEQ ID NO:41.

DESCRIPTION OF THE FIGURES

FIGS. 1A-1C. Identification of PFD0495c as a candidate gene linked to sphingolipid synthesis. (A) Summary of transcriptional response suggesting PPMP-parasites are trophozoite-like, derived from FIGS. 6A and 6B. (B) Log odds ratio plot[25,26] of transcriptional changes in PPMP-treated parasites relative to control trophozoites with white squares indicating genes predicted to be exported to the erythrocyte and conserved and synthetic across *Plasmodium* species 3. *PFC0435w is down regulated ~4 fold. **PFD0495c is upregulated ~3 fold. (C) Schematic of PFD0495c features and number of variant repeat sequences across indicated *P. falciparum* strains. SS, ER type signal sequence; HT, host targeting motif; repeat, variant repeat sequence indicated by asterisk; TM, predicted transmembrane domain; and, Cterm, C terminal domain downstream of TM domain.

FIGS. 2A-2C. PFD0495c is exported to the erythrocyte membrane. (A) Export of PFD0495c-GFP expressed as a transgene inserted into the *P. falciparum* chromosome using piggyBac. (Ai) C-terminal position of GFP tag. (Aii) piggyBac plasmid used for transfection. (iii) fluorescence image of clone 1 (iv) fluorescence and DIC image showing export of PDF0495c chimera to the erythrocyte (e) periphery (arrow) and intraerythrocytic spots (arrow head). GFP accumulates in parasite (p) due to constitutive expression using the cam promoter. ue, uninfected erythrocytes. (B) Topology of PFD0495c. C-terminus of PFD0495c-GFP is localized to erythrocyte cytoplasmic face. Anti-GFP signal is detected with tetanolysin alone. Control signal to PPM (aMSP-1) is detected only with saponin treatment. (C) Resealed erythrocyte ghosts were loaded with 50 μM GSTPFD0495cCterm (PFD0495c), GST-SBPCterm (SBP) or GST alone (GST), infected with *P. falciparum* at 2% schizonts and ring (R), trophozoite (T), schizonts (S) were monitored after 24 h (Day 1), 48 h (Day 2). Giemsa-stained smears indicate parasite morphology.

FIGS. 7A and 7B. qRT-PCR shows that PFD0495c transcript is up-regulated by PPMP treatment. (A) Ring-stage parasites (12 hpi) were treated with 5 μM PPMP for times indicated. RNA was harvested and reverse-transcribed into cDNA. Quantitative PCR was performed according to ABI protocols using 1 ng cDNA, 2 μM primers, and SYBR green. By 12 and 24 hr of treatment (24 and 36 hpi, respectively) PFD0495c transcript is significantly up-regulated compared to vehicle control. Up-regulation of PFD0495c in PPMP-treated parasites cannot be due to developmental delay because then the transcript level would be lower than the mock-treated control (see panel B). (B) Transcriptional profile over 48 hr life cycle provided by PlasmoDB. Peak of transcription occurs at 42 hpi. Gray diamond indicates upregulation in PPMP-treated cells after 24 h compared to corresponding normal parasites at 36 h. Since PPMP-treated parasites are slightly immature compared to mock treated control, up-regulation of PFD0495c cannot be a result of growth retardation of the treated parasites.

FIG. 8. Sequence of PFD0495c (SEQ ID NO:1). Location of PFD0495c on *P. falciparum* chromosome 4 and *P. vivax* genome (taken from PlasmoDB). In block diagram and sequence of PFD0495c: shaded box with sequence "MYK . . . ", ER-type signal sequence; shaded box with sequence "SFS . . . ", host targeting motif; shaded region with sequence "DDE . . . ", repeat region; shaded region with sequence "YFH . . . ", TM domain; Cterm, C-terminal region downstream from TM domain.

FIGS. 9A and 9B. ClustalW alignment of PFD0495c across *P. falciparum* strains. Sequence data for *P. falciparum* Ghanaian strain (SEQ ID NO:4) was obtained from The Sanger Institute; HB3 (SEQ ID NO:2) and Dd2 (SEQ ID NO:6) sequence information was provided by the Broad Institute of Harvard and MIT. 3D7 (SEQ ID NO:5) sequence data was obtained from PlasmoDB. Shading boxes are the same as indicated for FIG. 8.

FIG. 15 shows the nucleic acid sequence of *Plasmodium falciparum* 3D7 EVP1 protein (SEQ ID NO:41, which is Accession No.: XM_001351379.1. This sequence may be used to design probes and primers to detect EVP1 in a sample from a patient suspected of being infected.

DEFINITIONS

Figure 1A:
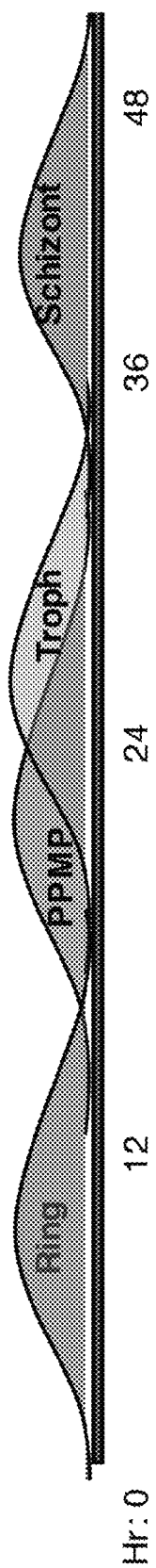

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "epitope" as used herein refers to that portion of an antigen that makes contact with a particular antibody. When a protein or fragment of a protein (e.g., EVP1, or fragments described in Table 1) is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject suspected of being infected with a *Plasmodium* species" refers to a subject that presents one or more symptoms indicative of such infection (e.g., symptoms of malaria). A subject suspected of being infected with *Plasmodium* species (e.g., falciparum) may also have one or more risk factors (e.g., exposure to mosquitoes in Africa). A subject suspected of infection generally not been tested for such infection.

A "patient antibody," as used herein, is an antibody generated in a patient (e.g., human) as a result of infection with a *Plasmodium* bacteria. In other words, it is the patient's own antibodies generated as a result of infection. Such antibodies provide evidence of infection and are therefore useful to detect in order to provide a diagnosis of *Plasmodium* infection.

As used herein, the term "instructions for using said kit for detecting *Plasmodium* infection in said subject" includes instructions for using the reagents contained in the kit for the detection and characterization of *Plasmodium* infection in a sample from a subject. In some embodiments, the instructions further comprise the statement of intended use required by the U.S. Food and Drug Administration (FDA) in labeling in vitro diagnostic products. The present invention contemplates kits with reagents for detecting *Plasmodium* infection, including antibodies to the antigens recited in Table 1, and nucleic acids sequences (e.g., primer pairs able to amplify at least a portion of SEQ ID NOs:1-6).

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Exemplary primers for detecting the *Plasmodium* target nucleic acids of the present invention are provided in the Examples below. One of skill in the art could design similar primers based on, for example, SEQ ID NOs:1-6.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

DETAILED DESCRIPTION OF THE INVENTION

The present invention provides anti-Plasmodium vaccine compositions comprising EVP1 or an antigenic portion thereof, as well as methods of immunizing against malaria employing these compositions. In other embodiments, the present invention provides methods of identifying Plasmodium infection employing agents that bind to EVP1 or an antibody generated thereto.

I. Identification of EVP1

Plasmodium falciparum is a protozoan parasite that causes the most virulent of human malarias. The blood stage parasites export proteins into their host erythrocyte that underlie modifications linked to major pathologies of the disease and parasite survival in the blood[1,2]. Several hundred gene products that are predicted to be exported[3,4] have the highest rates of nonsynonymous polymorphisms[5-7] and are of interest for identifying urgently needed new vaccine candidates and mechanisms of drug resistance as well as understanding disease severity in humans[8,9]. Unfortunately most are 'hypothetical' proteins of unknown function[3,4]. Those that are essential for parasitization of the erythrocyte cannot be 'knocked out'. In performing experiments for developing the present invention, an integrated series of transgenic and cellular assays were developed and used in combination with microarray and bioinformatics analyses, to identify the first *P. falciparum* exported protein required for intracellular growth. It is also the first parasite polymorphic protein unambiguously at the infected-erythrocyte surface that is encoded by a single copy gene, conserved across Plasmodium species and reacts with human immune serum, which has important implications for vaccine development. Using the methods as described herein to analyze hundreds of *P. falciparum* genes may rapidly yield multiple, high-value targets to advance effective vaccines and drugs against malaria.

Figure 5:
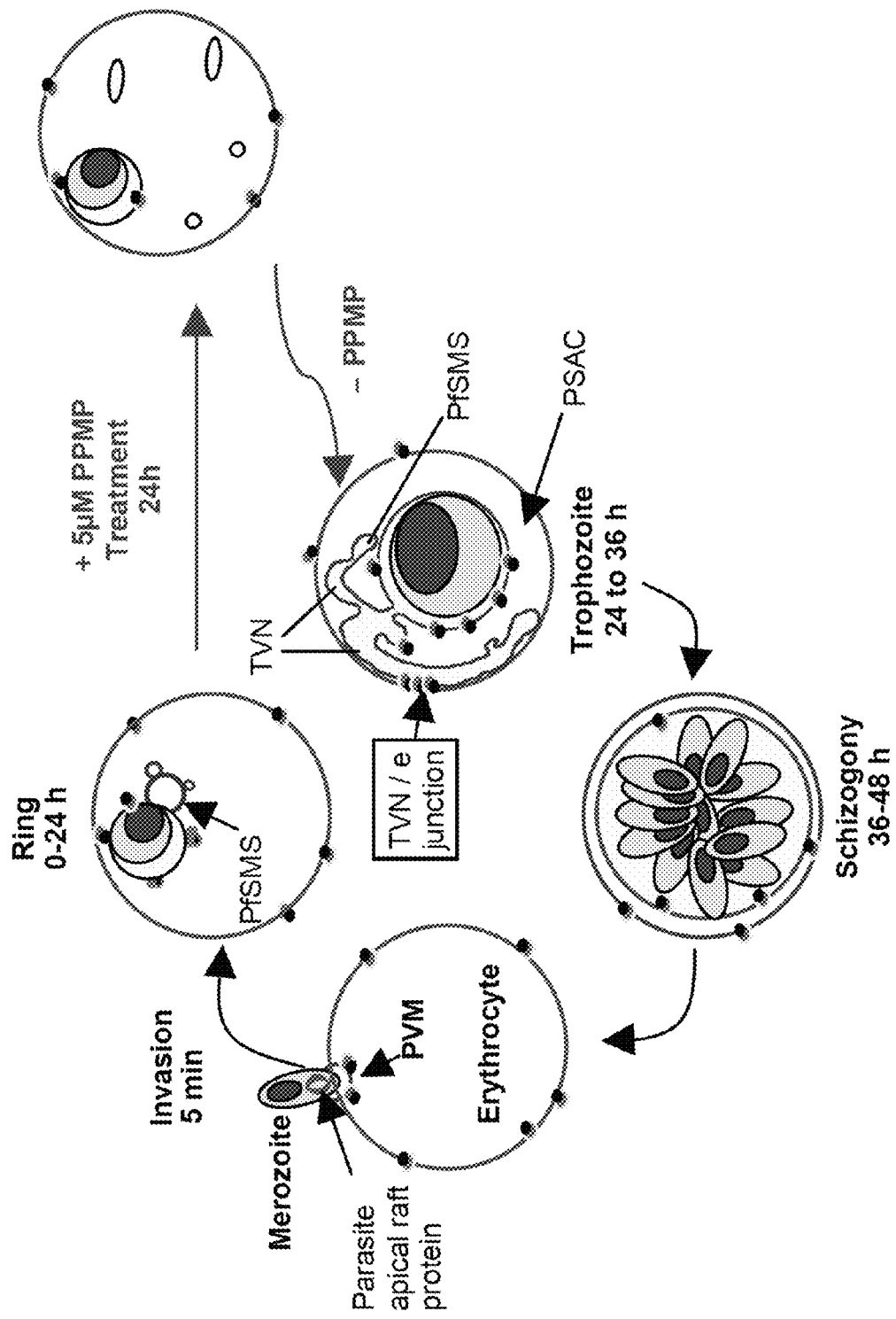
FIG. 5. Schematic of *P. falciparum* asexual blood stage cycle and model for involvement of erythrocyte and parasite rafts and sphingolipid synthesis in forming both the parasitophorous vacuolar membrane (PVM) and its attached tubovesicular network (TVN). Merozoites release parasite apical raft protein (loop and dots indicating proteins such as Pfstomatin or RhopH1) and recruit host rafts (dots such as flotillins and Gs) into the new vacuole. Intracellular ring stage parasites bud nascent TVN vesicles that stabilize into tubules at the trophozoite stage. dl-threo-PPMP inhibits parasite sphingomyelin synthase (PfSMS) in the TVN and blocks development of TVN-tubules. Parasite surface anion channel (PSAC) imports solute. TVN/erythrocyte (TVN/e) junction used by host raft proteins and lipids to directly access the TVN. Trophozoites mature to schizonts that divide into merozoites, which re-initiate a new round of infection.

Blood stage infection by the human malaria parasite *Plasmodium falciparum* begins when the extracellular merozoite stage invades the mature erythrocyte. The newly formed intracellular ring stage parasite is surrounded by a parasitophorous vacuolar membrane (PVM). As ring parasites mature to the trophozoite stage, a tubovesicular network (TVN) emerges from the PVM to support import of nutrients as well raft proteins and lipids from the erythrocyte membrane[10,11] (FIG. 5).

Tubule formation and import functions can be blocked by sphingolipid analogues (such as dl-threo-1-phenyl-2-palmitoyl-3-morpholino-1-propanol; PPMP)[11] that inhibit a parasite sphingomyelin synthase activity exported to the erythrocyte[12]. Development of the TVN is a remodeling feature of the erythrocyte but unambiguous identification of parasite genes involved in TVN development and function have remained elusive. Several hundred parasite proteins are predicted to be exported to the erythrocyte[3,4,13] but remain largely unvalidated, and those required for parasitization of the erythrocyte remain entirely unknown.

To facilitate the identification of essential, exported genes that regulate the TVN, an intersection of those linked to TVN assembly and function with those predicted to be exported to the erythrocyte and conserved across the genus *Plasmodium* was examined. To identify genes linked to the TVN, transcriptional changes induced in *P. falciparum* genes in response to treatment of infected erythrocytes with PPMP for 24 h were examined.

Figure 1B:
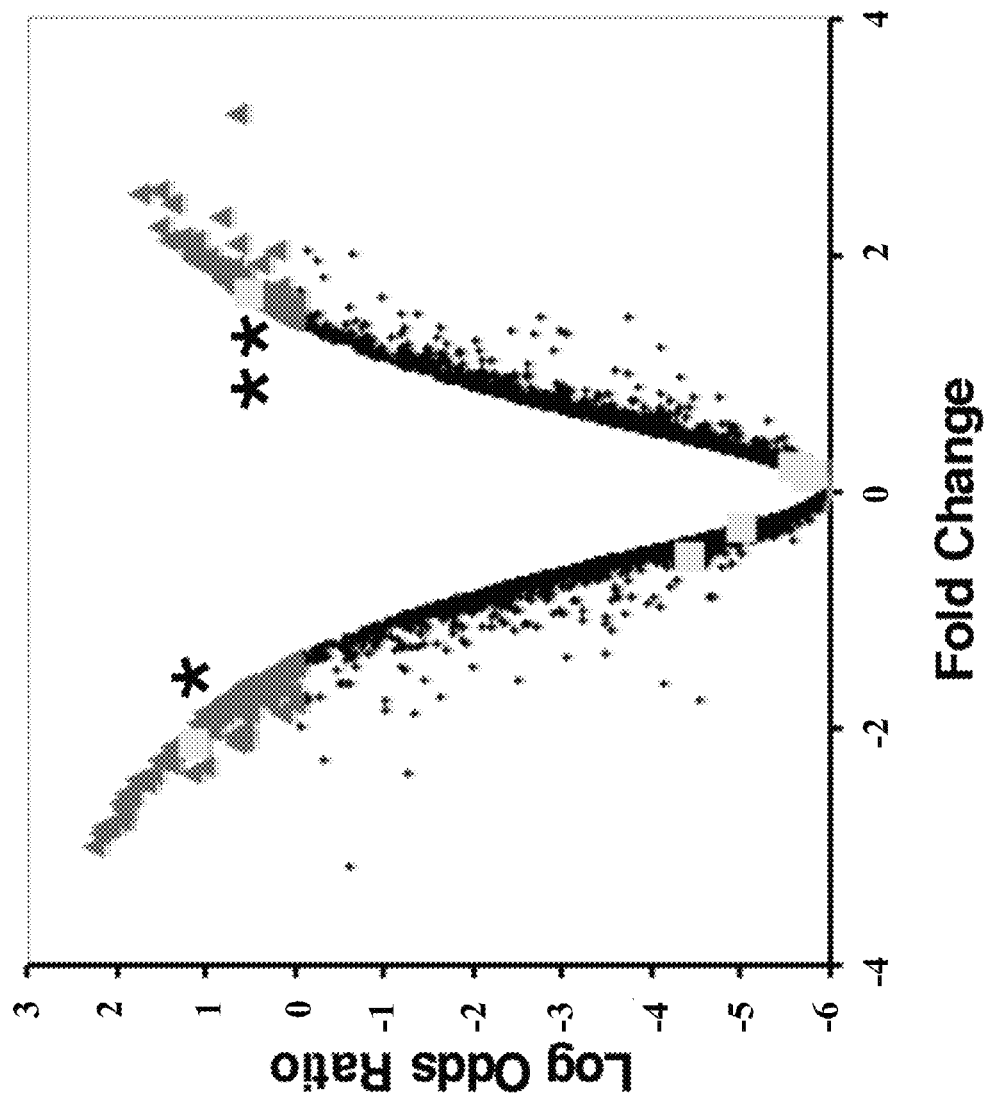
Figure 6:
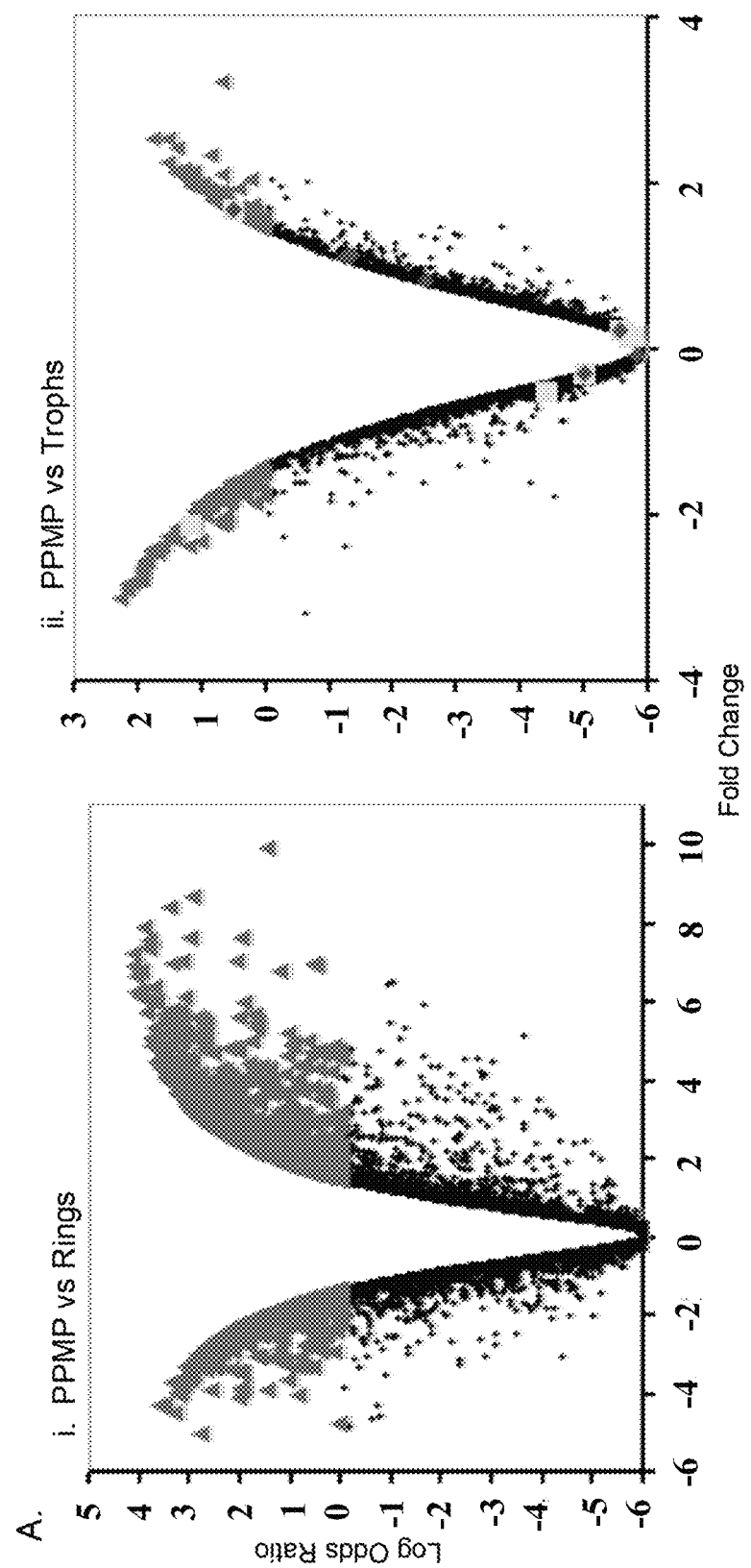
FIGS. 6A and 6B. Response to PPMP-treatment of conserved genes with host targeting motif. *P. falciparum* 3D7 ring stage parasites were treated with either 5 μM dl-threo-PPMP or vehicle ([ethanol]f=0.01%) for 24 hr, and the observed transcriptional change was determined by microarrays. (A) Log odds ratio plots of changes in PPMP-treated parasites relative to (i) rings (starting population) or (ii) trophozoites (obtained by mock treatment) revealed that transcriptional response of treated set is closer to the profile of trophozoite stage parasites. Thus PPMP-parasites are trophozoite-like. Gray indicates genes with fold changes greater than zero (373 genes for rings, and 81 for trophozoites). Since the number of genes that change is greater for rings than trophozoites, the PPMP-treated parasites are more similar to trophozoites and quite distinct from rings. White boxes indicates genes exported to the erythrocyte and conserved and syntenic across species as predicted by 1 (and shown in B). Gray circles indicates genes exported to the erythrocyte and conserved across species as predicted by 5, using an independent algorithm distinct from 1. At the trophozoite stage 39 genes were upregulated and 42 were down-regulated. *PFC0435w is downregulated 4 fold. **PFD0495c is upregulated ~3 fold. (B) List of genes containing a host-targeting motif 1 conserved between *Plasmodium falciparum* and *P. yoelii*. Response to PPMP treatment is shown in yellow in panel A.

As summarized in FIG. 1a, b and FIG. 6, the overall transcriptional profile of PPMP-treated parasites is distinct from rings and is trophozoite-like, and these parasites are slightly less mature than normal trophozoites. As such, changes in transcriptional profiles relative to the trophozoite stage were examined (FIG. 1b, FIG. 6). In genes that are predicted to be exported to the erythrocyte[3,4] those conserved between human and rodent malaria parasites[3] (FIG. 6) were investigated as they were likely to reflect essential functions of parasite remodeling of the host cell preserved across parasite species. An intersection of these genes with those that show PPMP-induced changes in transcriptional profiles relative to the trophozoite stage yielded two conserved genes (PFD0495c and PFC0435w; asterisks, FIG. 1b), of which one (PFD0495c) was up-regulated (double asterisk FIG. 1b). It is contemplated that this upregulation is not due to a delay in parasite maturation (induced by PPMP), and hence it was further confirmed by RT-PCR (FIG. 7).

Figure 2B:
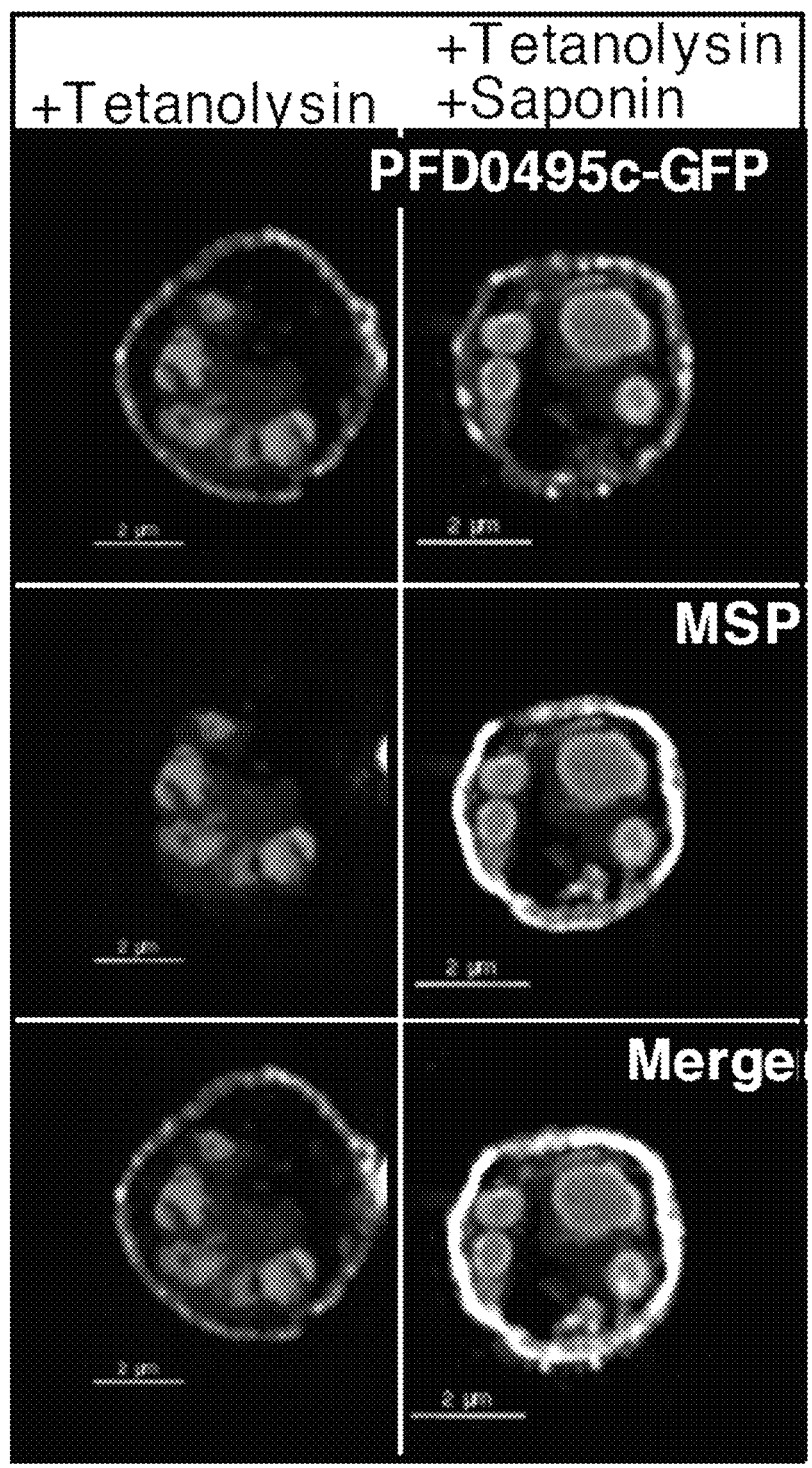
Figure 10:
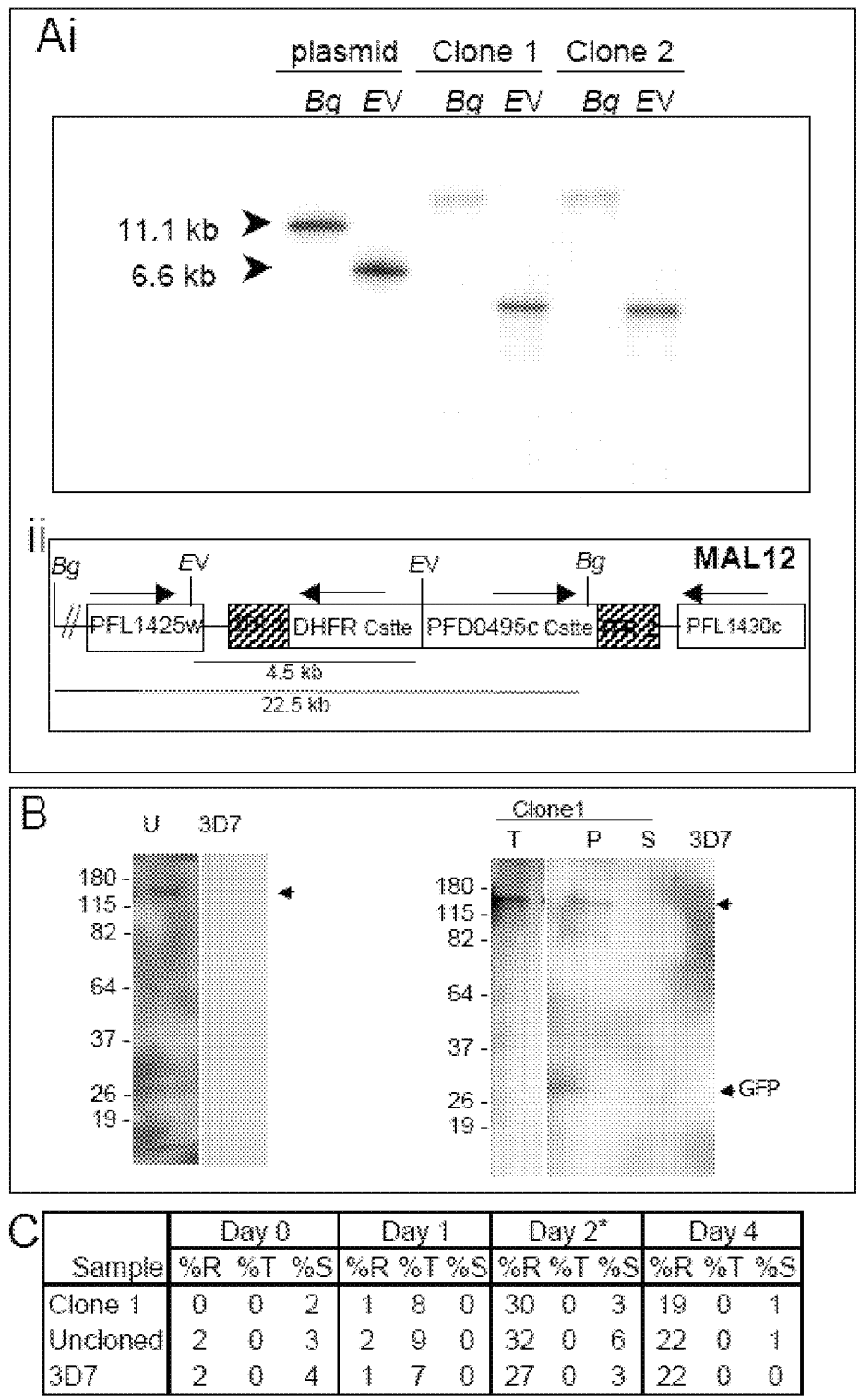
FIG. 10. Site of insertion of PFD0495c-GFP into *P. falciparum* chromosome 12 and western blots of transgenic parasites. (Ai) Southern analysis of clone 1. Southern hybridization analysis shows that clone1 has a single insertion in the genome with no evidence of episomes. Genomic DNA (2 ug) from two independent clones (1 and 2) and control plasmid DNA were digested with either BglII or EcoRV and probed with hdhfr coding sequence. (Aii) Insertion of the expression cassette within the piggyBac Inverted Terminal Repeats occurred in chromosome 12 between loci PFL1425w (T complex protein) and PFL1430c (hypothetical protein) as determined by PCR. PFL1425w is expressed in the asexual stages but does not have a predicted ER-type signal sequence so would remain within the parasite cytosol. PFL1430c is expressed in the sexual stages and to a lesser extent in asexual stages. It does have a predicted ER-type signal sequence but no host-targeting motif, so it would not be exported beyond the PVM. No differences are seen in parasite growth (see panel C). (B) Western blots indicating a band (arrow) of 150 kDa (expected size of 130 kDa for protein chimera) in total cell lysates of clone 1 and 3D7 parasites (WT). GFP chimera protein of uncloned population present only in pellet fraction after hypotonic lysis. Total cell lysates (T), pellet after hypotonic lysis (P) and supernatant (S). (C) Growth curve of clone 1, uncloned population, and 3D7 parasites over 4 days. Percoll purified schizonts were seeded at 2-4% schizonts in 2% hematocrit. Duplicate cultures were monitored for two cycles of growth by Giemsa-stained smears. *At Day 2, all lines were sub-cultured to 3% late rings, which matured to 3% trophs/schizonts on Day 3 and indicated parasitemia on Day 4. Counts are from duplicate experiments. Error is 10%.
Figure 11:
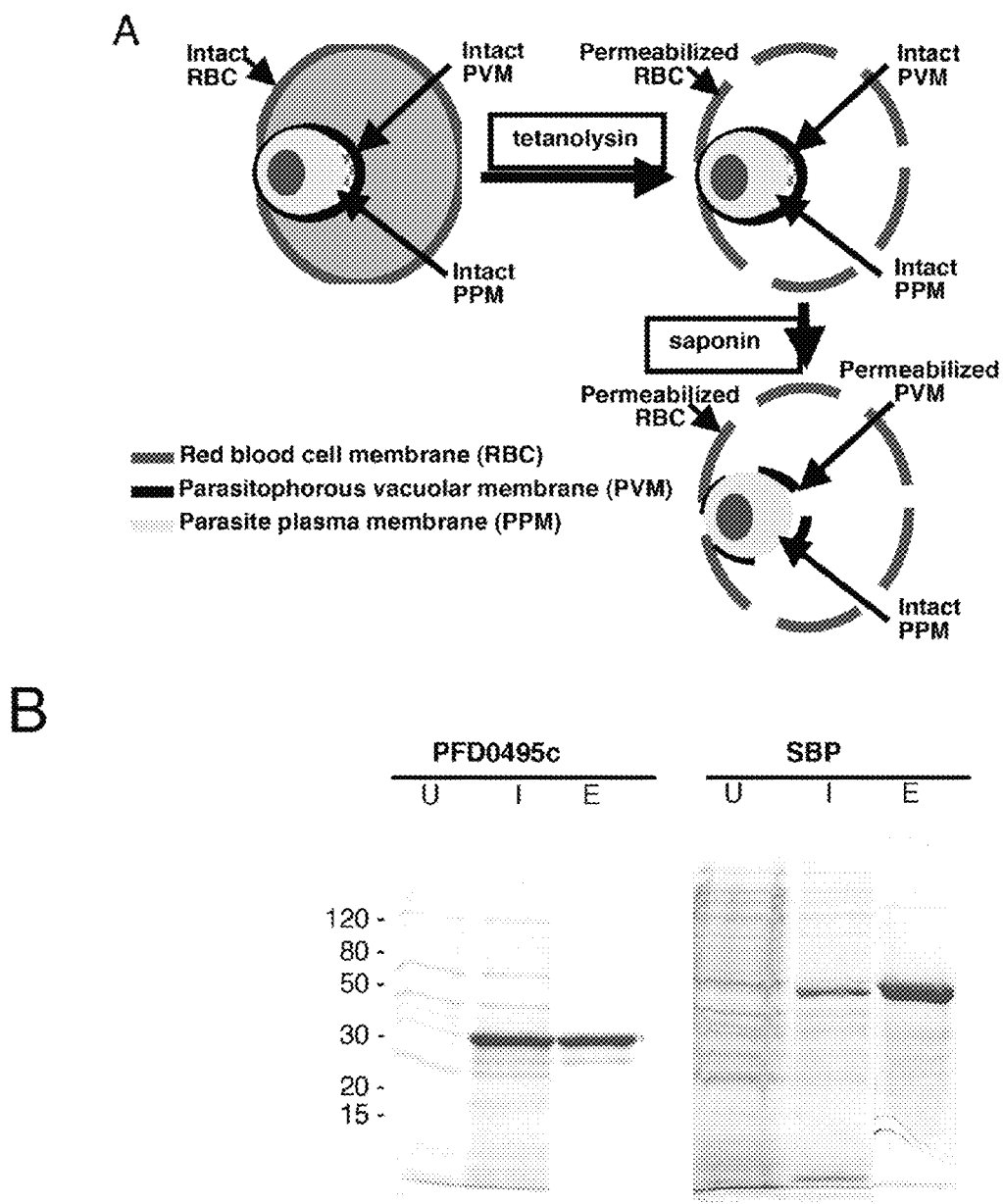
FIG. 11. Schematic of selective permeabilization experiment to determine topology of PFD0495c and purification of recombinant GST fusion used in ghost loading assays. (A) Tetanolysin selectively permeabilizes only the erythrocyte plasma membrane, leaving the PVM intact. Only in combination with saponin will the PVM be permeabilized and control MSP1 antibodies gain access to epitope. If anti-GFP signal can be detected with tetanolysin alone, then the C-terminus is present on the cytoplasmic face of the erythrocyte. (B) Coomassie stained SDS-PAGE analyses of GST-fusions of C-terminal domains of PFD0495c and SBP expressed in *E. coli* (>90% purity) purification under native conditions. U, uninduced, I, induced, E, eluate containing purified protein.

To establish that PFD0495c is exported to the erythrocyte, piggyBac (a type II transposon element from the lepidopteran *Trichoplusia ni*, that specifically excises and integrates at TTAA target sites) was utilized to randomly insert a tagged copy of PFD0495c-GFP in the genome[14] (FIG. 2ai-ii). Integrants detected after 11 days of drug selection were cloned (FIG. 10). PFD0495c-GFP was expressed as a 130 kDa membrane-bound protein (FIG. 10) that was exported to the erythrocyte in 100% of infected erythrocytes in uncloned and cloned isolates (FIG. 2aiii-iv). Clone 1, which was selected for further characterization, showed a single site of insertion between PFL1425w and PFL1430c (FIG. 10). This insertion site is contemplated to influence export. Further, clone 1 showed no significant defect on in vitro parasite growth compared to either the uncloned population or parent 3D7 parasites (FIG. 10). Topology studies revealed that the C-terminus of PFD0495c is exposed on the cytoplasmic face of the erythrocyte membrane (FIG. 2b and schematic in FIG. 11).

Figure 2C:
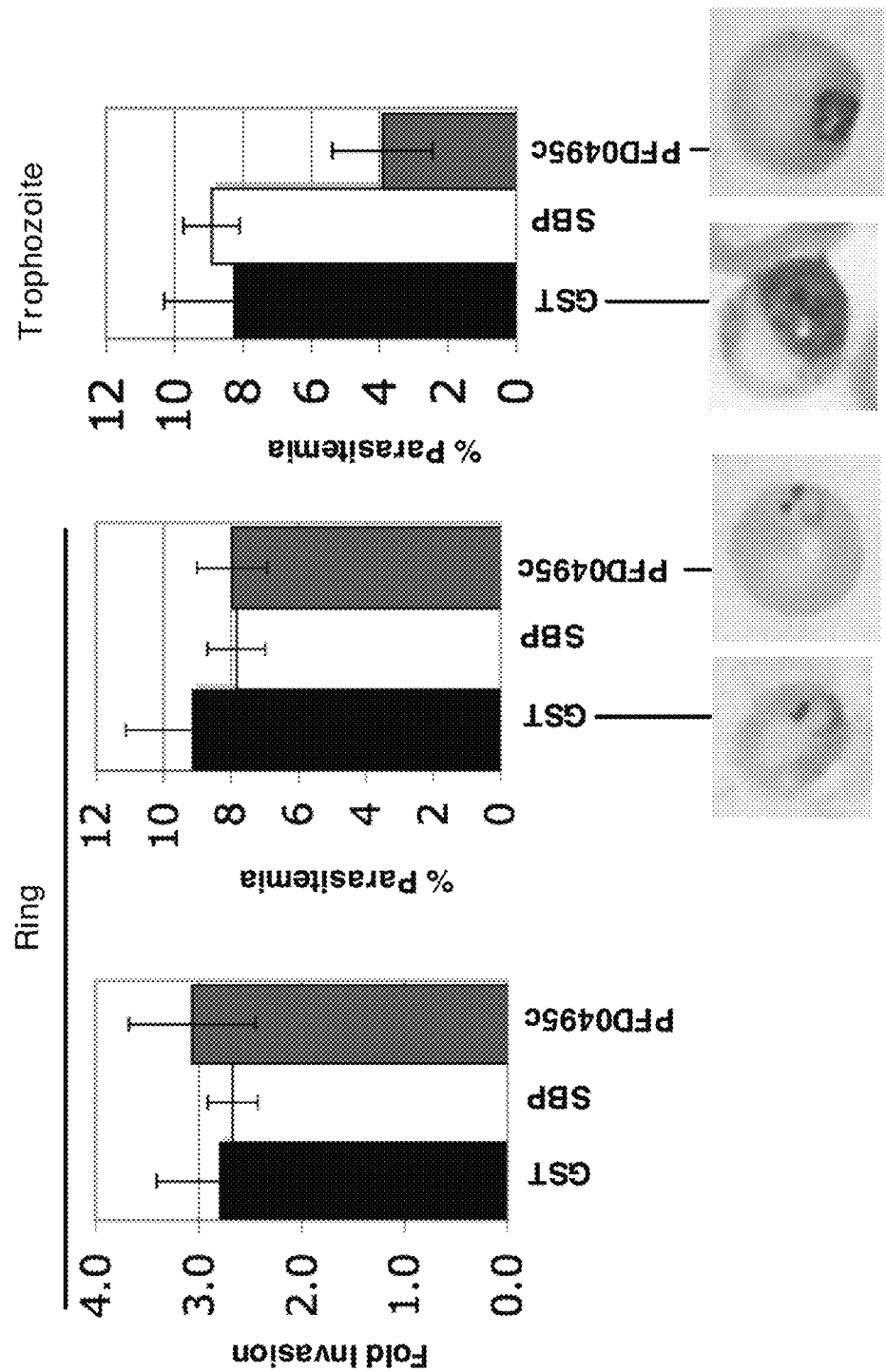
Figure 12:
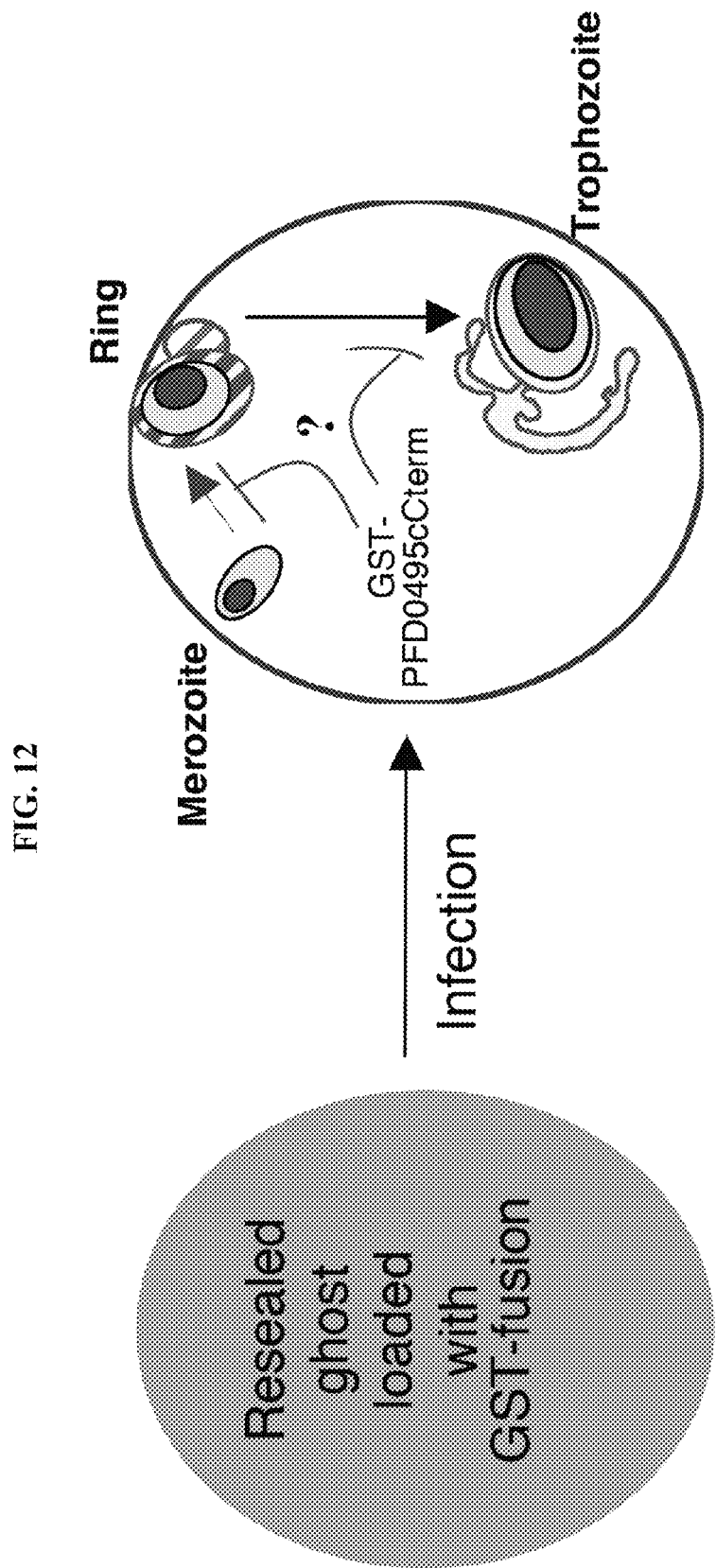
FIG. 12. Strategy designed to target PFD0495c cytoplasmic interactions in erythrocyte ghosts to identify whether this blocks either parasite invasion or intraerythrocytic growth. GST-fusions of C-terminal domain of PFD0495c loaded into re-sealed erythrocyte ghosts block interactions of the endogenous protein on the cytoplasmic face of the new and developing PVM-TVN. Our results show that GST fusion of C-terminal domain of PFD0495c blocks parasite growth but not invasion. GST fusion of C-terminal domain of PfSBP (exposed on cytoplasmic face of Maurer's clefts) has no effect on infection consistent with prior data that the gene can be knocked out. The strategy does not require any prior information about the function of a protein and thus provides a powerful tool to annotate functions of 'hypothetical' genes in the *P. falciparum* genome. Parasite proteins targeted to the erythrocyte show the highest ratios of nonsynonymous to synonymous polymorphisms and may provide targets for drug and vaccine development.

To assess its functional importance to infection, an approach was utilized in developing embodiments of the present invention that has been employed to identify known cytoplasmic determinants of both host and parasite origin needed for parasite invasion[15,16]. To extend this to a gene of hypothetical function, such as PFD0495c, 50 μM of a recombinant form of the C-terminal region of PFD0495c fused to glutathione S-transferase (GST-PFD0495cCterm; FIG. 11) was introduced into the cytoplasm of resealed erythrocyte ghosts[15] (FIG. 12). Introduction of GST-PFD0495cCterm had no significant effect on invasion (measured as ring formation), but was inhibitory to trophozoite growth. GST alone, or a recombinant fusion of a parasite protein domain (PfSBPCterm) known to be exposed to the erythrocyte cytoplasm but not required for infection[17], had no effect (FIG. 2c).

Figure 3:
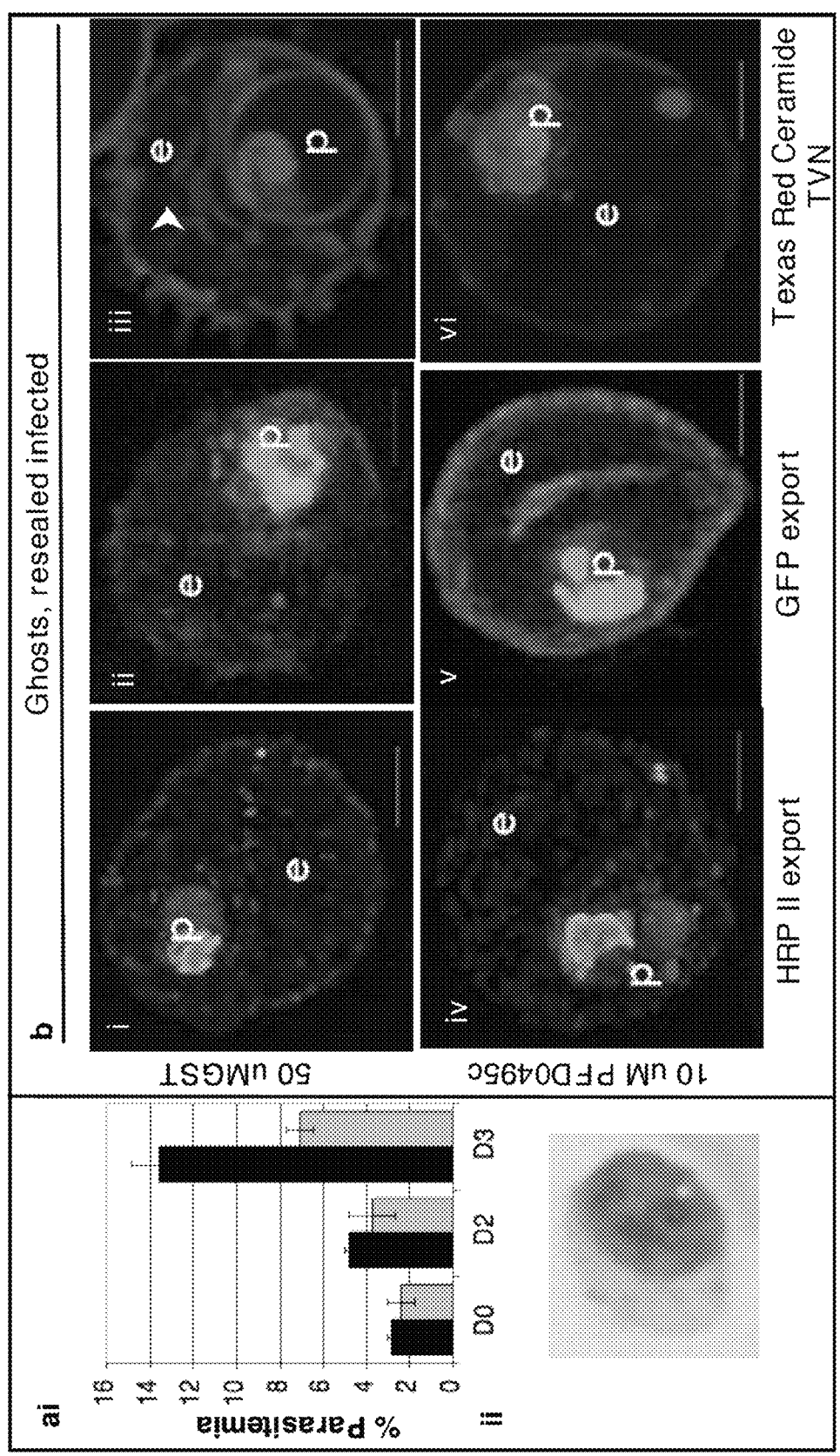
FIGS. 3A-3D. PFD0495c regulates the TVN in the infected erythrocyte cytoplasm. (A) (i) Erythrocyte ghosts were resealed with 10 μM GST-PFD0495cCterm (gray bars) or 50 μM GST alone (black bars) and infected with *P. falciparum* to achieve ring parasitemias of 2-3% on Day 1 (D1). On Day 2 in ghosts loaded with 50 μM GST, trophozoites, schizonts and few new rings were observed. However in D2 ghosts loaded with 10 μM GST-PFD0495cCterm, only trophozoites were seen (see aii). On Day 3 (D3), parasitemia in ghosts loaded with GST alone was well over 12-14% rings, while in ghosts with 10 μM GST-PFD0495cCterm it remained at 6-7%. (B) Trophozoite stage parasites in ghosts resealed with 50 μM GST (Bi, ii, iii), or 10 μM GST-PFD0495cCterm (biv, v, vi), were infected with: (bi, iv) 3D7 *P. falciparum* and probed with anti-HRPII or anti-MSP1 and Hoechst; (Bii, v) clone 1 expressing PFD0495c-GFP and visualized for live green fluorescence; (Biii, vi) 3D7 *P. falciparum* stained with the membrane permeable probe TR-ceramide and visualized live. (C) Transgenic *P. falciparum* parasites expressing PfHRPII-GFP (ci-ii) or PFD0495c-GFP (ciii-iv) treated in absence (Ci, Ciii) or presence (cii, civ) of 5 μM PPMP for 30 min were incubated with membrane impermeable endocytic lipid marker FM4-64 (red) also for 30 min and imaged live. A second copy of PFD0495c promotes internalization of FM4-64 probe in the presence of PPMP (Civ versus Cii). (D) Ring stage parasites (3D7 iii, PFD0495c-GFP clone 1 iii-iv) were incubated in absence (Di, Diii) and presence of 5 μM PPMP (Dii, Div) for 24 hr and stained with Texas Red-ceramide for TVN visualization and Hoechst for parasite DNA. In the presence of PPMP clone 1 accumulates an abundance of small loops and tubovesicular structures (Div) compared to few punctate spots in 3D7 (Dii). Arrows show tubules, loops; arrowheads, vesicular structures; small arrowheads, punctate spots. For all panels erythrocyte (e), parasite (p) and intraerythrocytic structures (arrow). Scale bar, 2 μm.
Figure 3:
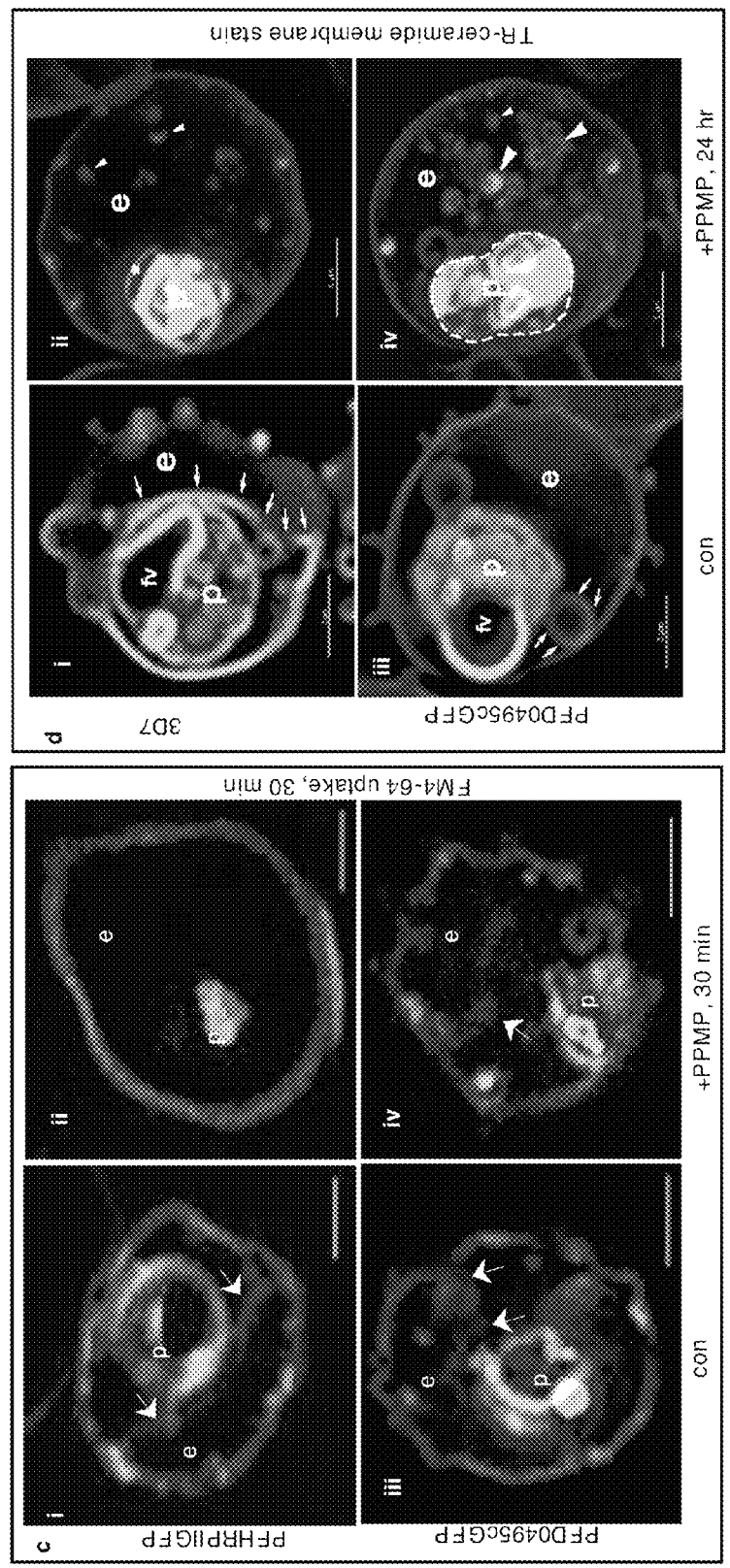
Figure 13:
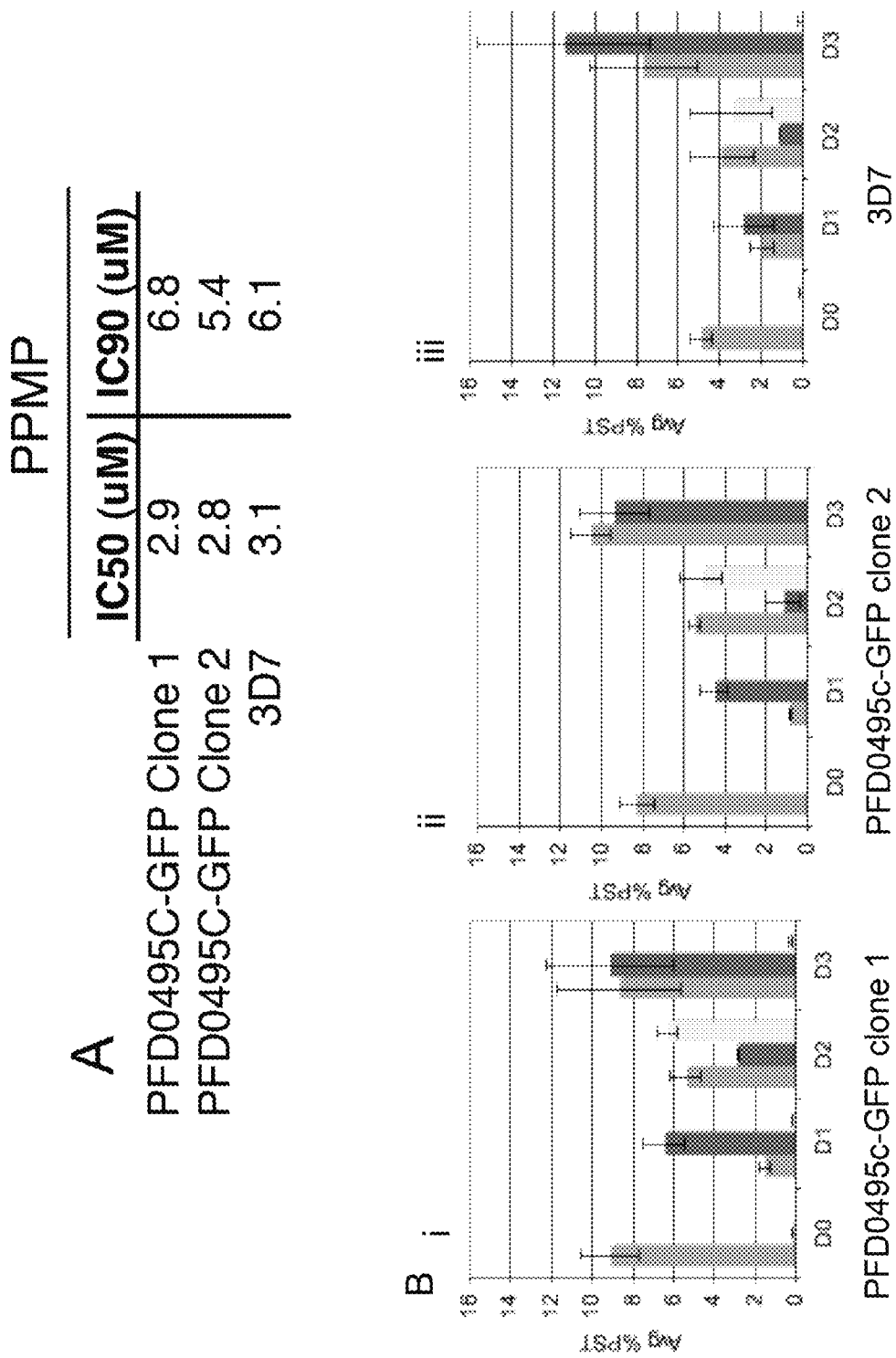
FIG. 13. Comparative analyses of effects of PPMP on maturation of parent 3D7 and clones 1 and 2 expressing PFD0495c-GFP. (A) IC50 and IC90 measurements as measured in standard hypoxanthine uptake experiments. Both PFD0495c-expressing clones displayed similar sensitivity to PPMP as 3D7 *P. falciparum* parasites, indicating that neither was altered in sphingomyelin synthase activity. (B) Reversibility of PPMP on asexual parasite growth after 24 h in culture for (i) clone 1, (ii) clone 2, (iii) 3D7 *P. falciparum* parasites. 12 h Ring stage parasites (medium gray) at Day 0 were incubated in 5 μM PPMP for 24 h. At Day 1, late rings and young trophozoites (dark gray) were detected. Removal of PPMP at day 1 enabled control and transgenic parasites to mature to trophozoites (dark gray) and schizonts (light gray) at day 2 as well as new rings (medium gray) and trophozoites (dark gray) at day 3. When PPMP was washed out, both PFD0495c-expressing clones progressed through the asexual cycle similar to 3D7 parasites. Rings and trophozoites matured to trophozoites and schizonts, respectively. This experiment provides support that neither clone is altered in sphingomyelin synthase activity.

To investigate whether inhibition of trophozoite maturation could be specifically linked to intraerythrocytic transport functions, the concentration of GSTPFD0495cCterm in the erythrocyte cytoplasm was reduced to 10 μM. This allowed growth of enlarged trophozoites (see FIG. 3ai-ii) and had no deleterious effect on parasite protein export (FIG. 3bi and iv; ii and v). However, GST-PFD0495cCterm disrupted tubular-TVN development (FIG. 3biii and vi) as well as the next cycle of parasite growth (FIG. 3a), consistent with a defect in subsequent maturation of trophozoites to the schizont stage. If reagents designed to block PFD0495c function block TVN development, it was contemplated that PFD0495c may influence TVN function/structure. A major function of the TVN is lipid and raft protein import from the infected erythrocyte surface, that can be can be blocked by preventing TVN-tubule development by treating cells with PPMP[10]. As shown in FIG. 3ci, infected erythrocytes expressing a (non-specific) transgene PfHRPII-GFP (or 3D7 parasites; not shown) internalize a membrane impermeable endocytic lipid marker FM4-6418 via TVN tubules, and this import can be blocked by short-term (30 min) treatment with PPMP (FIG. 3cii). However, clone 1 expressing a second copy of PFD0495c continues to internalize FM4-64 despite treatment with PPMP (FIG. 3civ vs. ii). After long term (24 h) treatment with PPMP labeling of all intraerythrocytic membranes with a membrane-permeable lipid, Texas Red (TR) ceramide, revealed elevated accumulation of numerous membrane loops in the erythrocyte cytoplasm in clone 1 cells, compared to residual intraerythrocytic structures seen in their 3D7 counterparts (FIG. 3dii versus iv). It is contemplated that this difference in TVN organization was not due to, for example, changes in parasite sphingomyelin synthase activity inhibited by PPMP (FIG. 13) or transfection per se. In addition, the effects of PPMP on parasite growth in the parent line and multiple transgenic clones were completely reversible upon washing out drug (FIG. 13), suggesting that membrane accumulation seen in FIG. 3div, is not due to non-specific degeneration of intraerythrocytic structures as a consequence of parasite death but due to the presence of a second copy of PFD0495c in the genome.

Figure 4:
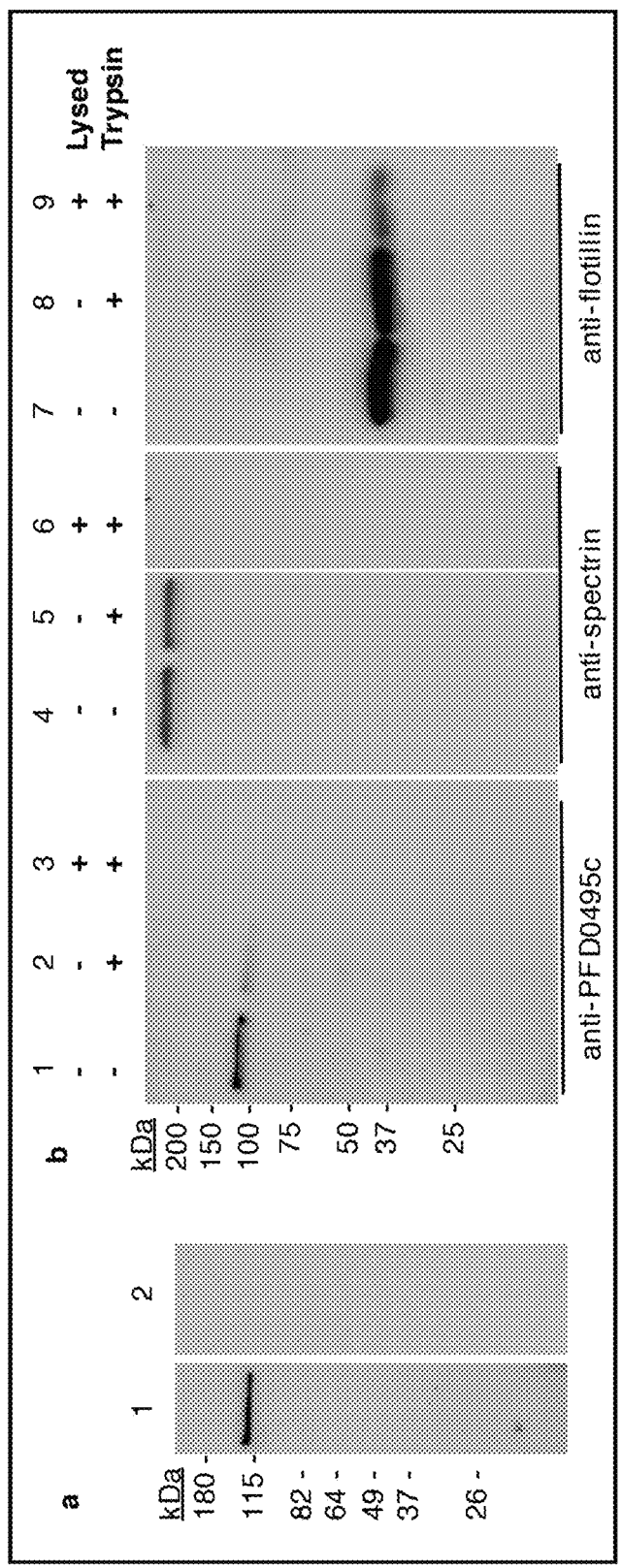
FIGS. 4A-4D. PFD0495c is a conserved, parasite antigen at the erythrocyte surface identified through genomic screens. (A) Western blots show that antibodies to the C-terminus of PFD0495c recognize a single ~120 kDa band in infected (lane 1) but not uninfected (lane 2) erythrocytes. (B) Mild trypsin treatment of 2×10⁶ intact, schizont-infected erythrocytes leads to reduction of PFD0495c (lane 2). As controls, one aliquot of infected erythrocytes was left untreated (lane 1), and another aliquot was lysed then treated with trypsin (lane 3). Intact cells, untreated (lanes 4, 7) and treated with trypsin (lanes 5, 8) as well as lysed cells treated with trypsin (lanes 6 and 9) were also probed with antibodies to spectrin (lanes 4-6), and flotillin 2 (lanes 7-9) as indicated, to confirm that trypsin treatment alone did not compromise the integrity of the infected erythrocyte membrane. Note: mild trypsin treatment reduces but does not abrogate flotillin levels due to inefficient digestion. (C) Western blot shows human immune sera reacts with the repeat region of PFD0495c. GST fusions (1 μg) of the repeat region (lanes 3, 6, 9) and C-terminus (lanes 4, 7, 10) of PFD0495c were blotted and probed with pooled human immune sera (lanes 1-5) or non-immune sera (lanes 6-8). Ponceau staining shows equal loading (lanes 9-11). Controls included GST alone (lanes 5, 8, 11), schizont-infected erythrocytes (lane 1, 1×10⁵), and uninfected erythrocytes (lane 2, 1×10⁵). (D) Flow diagram of strategy to identify and functionally characterize *P. falciparum* proteins exported to the erythrocyte and required for blood stage parasite infection. Steps 2-4 can be completed in ~5 weeks indicating time to identifying whether a candidate predicted to be involved in erythrocyte remodeling is exported to the host cell, essential for either invasion or intracellular parasite growth. Additional functional characterization can be completed in ~4-8 weeks.
Figure 4:
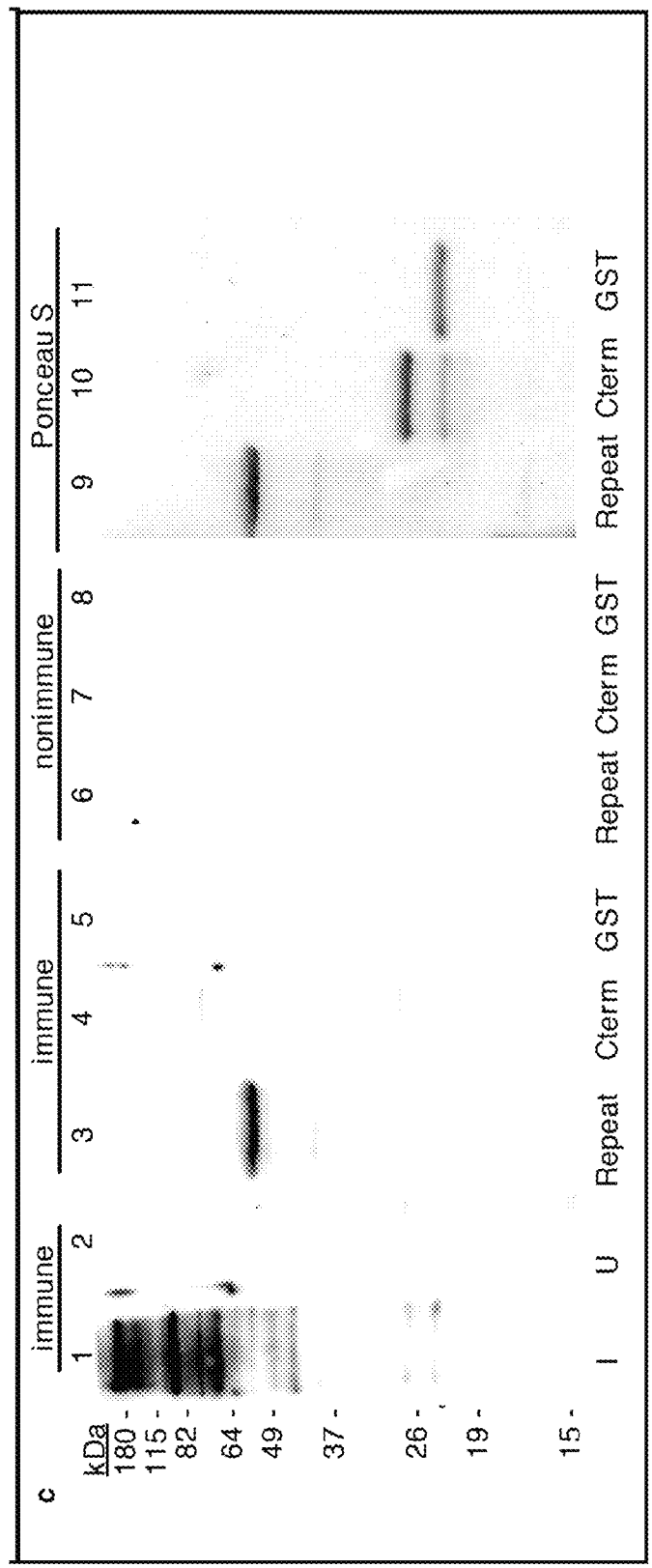
Figure 14:
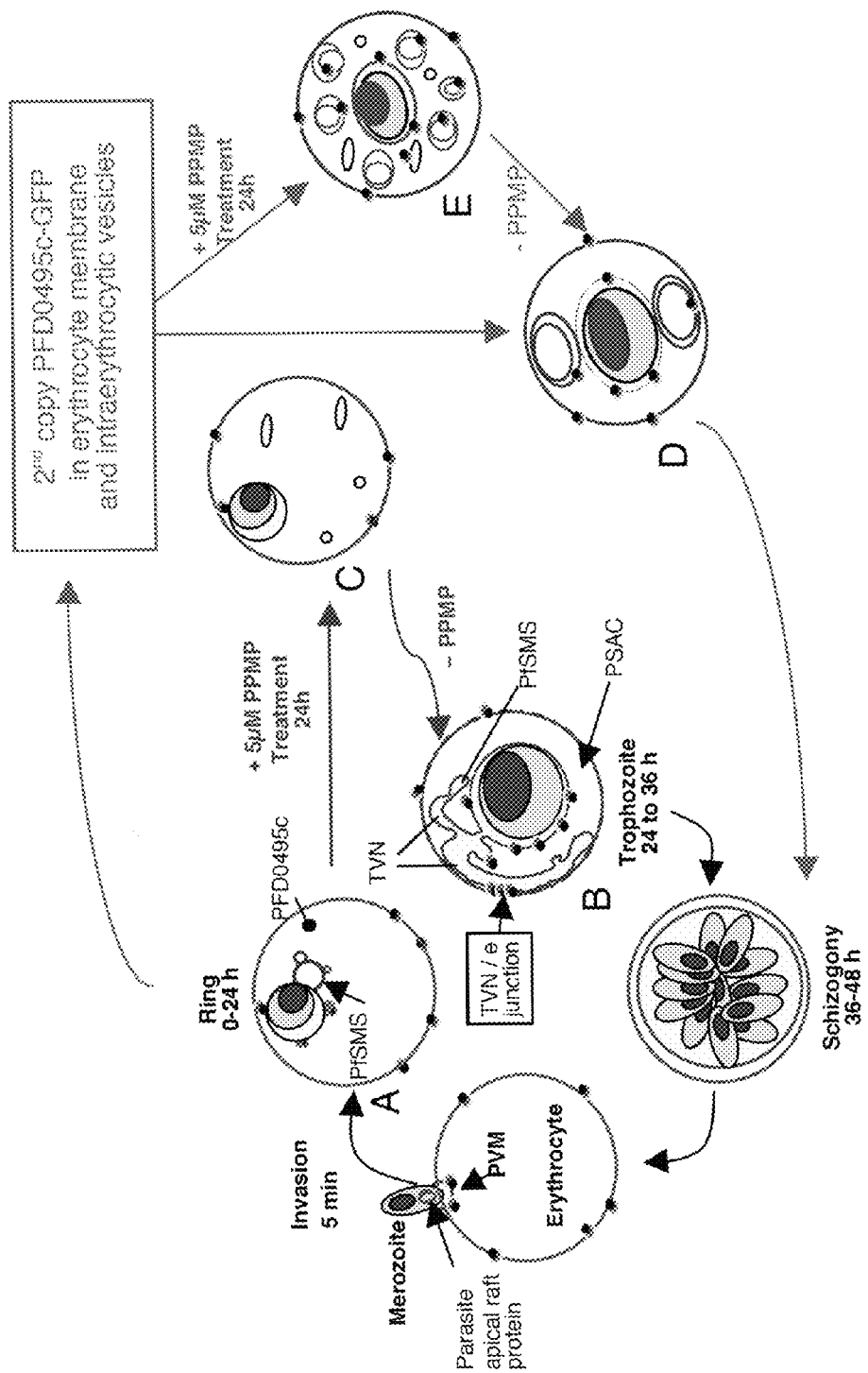
FIG. 14. Exemplary model for involvement of erythrocyte and parasite rafts, sphingolipid synthesis in the PVM-TVN and a hypothetical gene PFD0495c. As outlined in FIG. 5, rings (A) bud nascent TVN vesicles that, in the presence of sphingomyelin synthesis, stabilize into tubules at the trophozoite stage (B). dl-threo-PPMP inhibits sphingomyelin synthesis in the TVN and blocks development of TVN-tubules (C). Expression of the transgene PFD0495c-GFP stimulates large loops (not tubules) in TVN of trophozoites and schizonts (D). Treatment of transgenic cells with dl-threo-PPMP induces many small loops and vesicles in the erythrocyte (E). These vesicles are stained by a membrane impermeable dye that is usually excluded from uptake in PPMP treated cells. While not necessary to understand to practice the present invention, it is contemplated that PFD0495c drives vesicular lipid uptake at the infected erythrocyte membrane, and sphingomyelin synthase drives tubule formation and lipid uptake via tubules possibly to increase the efficiency of uptake. PSAC, Parasite surface anion channel (PSAC) for solute import 21. TVN/erythrocyte (TVN/e) junction used by host raft proteins and lipids use to directly access the TVN.

Together these data support that PFD0495c promotes vesicular lipid uptake at the infected erythrocyte membrane. Further, the recombinant form of C-terminus PFD0495c does not block export of either soluble or membrane parasite proteins to the erythrocyte. It does, however, block TVN assembly possibly because it inhibits the action of the endogenous C-terminal domain of PFD0495 in lipid vesiculation at the erythrocyte membrane (FIG. 14), which may be needed (e.g., in addition to sphingomyelin synthase-induced tubules) for proper development of the TVN. Experimentation demonstrates that PFD0495c-GFP is at the erythrocyte membrane with a functionally important, cytoplasmically-oriented C-terminus. This, in conjunction with the prediction that it is a type I membrane protein, demonstrates that PFD0495c is exposed at the infected erythrocyte surface. Antibodies to the C-terminal domain detect a single protein band of ~120 kDa in infected erythrocytes (FIG. 4a; the predicted size of the protein is ~100 kDa, but its apparent decrease in mobility could be due to the fact that it is a transmembrane protein). Mild protease treatment of infected erythrocytes leads to significant loss of the native PFD0495c (FIG. 4b). In contrast, spectrin, a high molecular weight cytoskeletal protein immediately under the erythrocyte membrane, and flotillin, a cytoplasmically oriented protein embedded in the erythrocyte bilayer, are not degraded (e.g., unless cells are lysed), demonstrating that PFD0495c is exposed on the surface of intact, infected erythrocytes. The location of its predicted transmembrane domain suggests that the bulk of the protein (from the N-terminus domain containing conserved sequences as well as repeat sequences of DD(EN/K/N)V(S/R/H/N)(N/H)(I/T)(N/K) to the transmembrane region) is likely to be extracellular. The number of repeats varies from 17-25 across P. falciparum strains (FIG. 1c and FIGS. 8-9). Antibodies in human immune serum react with these repeat sequences, but not the conserved, cytoplasmically-oriented C-terminus (FIG. 4c), suggesting an extracellular domain of PFD0495c is antigenic and interacts with the host immune system. Together, the data demonstrate PFD0495c is a polymorphic, but Conserved Erythrocyte Surface Antigen, and thus termed CESA-1 (or more preferably Erythrocyte Vesicle Protein 1, EVP1).

Other blood stage proteins reported to be at the infected erythrocyte surface are encoded by large variant gene families[19]. PfEMP1, one such protein, is not required for parasitization of the erythrocyte[20,21] and thus its utility as a vaccine target may be limited. In contrast, CESA-1 (EVP1) is a single copy gene with essential function and conserved regions exposed at the erythrocyte surface, suggesting that an immune reaction directed against it could not be evaded by merely turning on an alternate gene family member. The data provided herein demonstrate that a portion of the protein is exposed at the erythrocyte surface and that CESA-1 (EVP1) interacts with the host immune system during infection. Further, this interaction may occur over hours. Since invasion of the erythrocyte is rapid, current, leading blood stage vaccine candidates such as MSP1 and 2 as well as AMA1 are accessible on infectious merozoites for minutes prior to invasion.

A road map (FIG. 4d) to rapidly move from in silico predictions is provided herein in confirming export of parasite-encoded genes to the erythrocyte and identifying parasite protein domain(s) functioning within the erythrocyte cytoplasm. Protein interactions of such domains important for invasion or intracellular parasite growth may be disrupted by loading their recombinant forms in resealed erythrocyte ghosts. The use of small peptide domains (e.g., for example, of 30-90 amino acids) in GST fusions circumvents difficulties in expressing recombinant forms of P. falciparum proteins without codon optimization and is consistent with published data that small protein domains of P. falciparum are efficiently expressed as soluble protein in E. coli[22]. Larger, more insoluble domains can be truncated into smaller domains to identify specific inhibitory portions. It is contemplated that truncations in conjunction with secondary structure prediction and production of overlapping fragments can assist in production of optimal fragments.

It is contemplated that P. falciparum genes of hypothetical function involved in blood stage infection provide a rich vein for vaccine and drug targets because they lack recognizable orthologues in human hosts and other organisms. The strategies as described herein (FIG. 4d) are applicable to over 50% of parasite genes involved in pathogen-host interactions with nonsynonymous polymorphisms in a genome of ~5000 genes where over half have hypothetical function and less than 10% have a recognizable active site[23]. A critical feature is utilization of powerful genomic and functional assays to identify critical, essential exported proteins that have no prior in silico annotatable features. The strategy as described herein revealed that conserved parasite antigens may be expressed at the infected erythrocyte surface and present urgently needed, new targets to develop both vaccines and drugs against this major human pathogen.

II. *Plasmodium* Antigens

In preferred embodiments, the present invention provides anti-Plasmodium vaccine compositions that may be used, for example, to protect subjects from getting malaria. In certain embodiments, the vaccine compositions comprise an isolated EVP1 protein (e.g., SEQ ID NOs:1-6) or an antigen portions thereof. In particular embodiments, the vaccine compositions an EVP1 fragment comprising or consisting of a sequence selected from SEQ ID NOs:7-28, as shown in Table 1 below.

TABLE 1

| Sequence | SEQ ID NO |
|---|---|
| DDEVSNINDDEVSNIN | SEQ ID NO: 7 |
| DDEVSNINDDEVSNIK | SEQ ID NO: 8 |
| DDVVRNINDDVVRNIN | SEQ ID NO: 9 |
| DDEVHHTNDDKVNHTN | SEQ ID NO: 10 |
| DDKVNHTNDDKVNHTN | SEQ ID NO: 11 |
| DDNVNHTNDDKVNHTN | SEQ ID NO: 12 |
| MYKKCFILYPIFFPSLYI | SEQ ID NO: 13 |
| SFSRIIAEYCD | SEQ ID NO: 14 |
| YFHILVISLIFYLNLHSMYTLFI | SEQ ID NO: 15 |
| DLDIDDTLKFQHDQEFLNYFKRYQDFNNQLFDSFRSDDR | SEQ ID NO: 16 |
| LKFQHDQEFLNYFKRYQDFN | SEQ ID NO: 17 |
| VMNPNTNRALSINTVFNYNKENK | SEQ ID NO: 18 |
| LNYYTKFLTLDKYKNMYNCLNND | SEQ ID NO: 19 |
| PHGLRGNIKYYYFFNRIVST | SEQ ID NO: 20 |
| NYYFFNYMSTTIVYSVKKRSYEYIQ | SEQ ID NO: 21 |
| DITYYFKLIVNKIESKRLFSEPVMLCFQLFS | SEQ ID NO: 22 |
| SKNKIRYNPTEFLIYKFFSSIQY | SEQ ID NO: 23 |
| DDNVNHTNDDKVN | SEQ ID NO: 24 |
| DDKVNHTNDDNVNHTNDDKVNHTN | SEQ ID NO: 25 |
| DDNVNHTNDDKVNHTNDDK | SEQ ID NO: 26 |
| GESILGATSSRSTSLNIEQN | SEQ ID NO: 27 |
| MYKKCFILYPIFFPSLYIYIIKNDHLNSEQSSFSRI | SEQ ID NO: 28 |

In certain embodiments, the isolated fragments of EPV1 are 10-100 amino acids in length (e.g., 10 . . . 25 . . . 35 . . . 45 . . . 50 . . . 75 . . . 95 . . . or 100 amino acids in length). In other embodiments, they are conjugated to a hapten. It is noted that antigenic portions of full-length EVP1 (e.g., SEQ ID NOs:1-6) can be identified by methods known in the art.

For example, portions of the EVP1 protein (e.g., 15-100 amino acids in length) can be selected from EVP1 and injected into an animal (e.g., mouse, rat, or rabbit). The immune response of the animal can be examined to determine if antibodies have been generated to the portion injected (e.g., by a Western blot a sample from the subject). The animal may also be challenged with live *Plasmodium* bacteria (e.g., *Plasmodium falciparum*) to determine if the injected portion provides protection from infection by the *Plasmodium* bacteria.

III. Detection of *Plasmodium* Infection

In some embodiments, the present invention provides methods for detection of the *Plasmodium* infection by detecting the presence of EVP1 protein or nucleic acid in a patient sample. In some embodiments, expression is detected in bodily fluids (e.g., including but not limited to, plasma, serum, whole blood, mucus, and urine).

1. Detection of Nucleic Acid

In some embodiments, detection of EVP1 is detected by measuring the existence of nucleic acid encoding EVP1 in a patient sample. FIG. 15 provides the nucleic acid sequence of EVP1 from *Plasmodium falciparum*, which may be used to design primers and probes. In some embodiments, nucleic acid is detected by Northern blot analysis. Northern blot analysis involves the separation of nucleic acid and hybridization of a complementary labeled probe.

In still further embodiments, nucleic acid is detected by hybridization to an oligonucleotide probe). A variety of hybridization assays using a variety of technologies for hybridization and detection are available. For example, in some embodiments, TAQMAN assay (PE Biosystems, Foster City, Calif.; See e.g., U.S. Pat. Nos. 5,962,233 and 5,538,848, each of which is herein incorporated by reference) is utilized. The assay is performed during a PCR reaction. The TAQMAN assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In other embodiments, nucleic acid is detected using a detection assay including, but not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci. USA 88, 189-93 (1991)); FULL-VELOCITY assays; and sandwich hybridization methods (e.g., U.S. Pat. No. 5,288,609, herein incorporated by reference in its entirety). In other embodiments, the detection assay employed is the INVADER assay (Third Wave Technologies) which is described in U.S. Pat. Nos. 5,846,717, 5,985,557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes).

2. Detection of Protein

In some embodiments, the EVP1 proteins are detected. Protein expression can be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme linked immunosorbent assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In certain embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. In other embodiments, the immunoassay described in U.S. Pat. Nos. 5,599, 677 and 5,672,480 (each of which is herein incorporated by reference) is utilized.

3. Antibodies and Antibody Fragments

The present invention provides isolated antibodies and antibody fragments against EVP1. Such antibodies and antibody fragments can be used, for example, in diagnostic and therapeutic methods. The antibody, or antibody fragment, can be any monoclonal or polyclonal antibody that specifically recognize EVP1. In some embodiments, the present invention provides monoclonal antibodies, or fragments thereof, that specifically bind to EVP1. In some embodiments, the monoclonal antibodies, or fragments thereof, are chimeric or humanized antibodies. In other embodiments, the monoclonal antibodies, or fragments thereof, are human antibodies.

The antibodies of the present invention find use in experimental, diagnostic and therapeutic methods. In certain embodiments, the antibodies of the present invention are used to detect the presence or absence of *Plasmodium* infection in a sample from a patient.

Polyclonal antibodies can be prepared by any known method. Polyclonal antibodies can be raised by immunizing an animal (e.g. a rabbit, rat, mouse, donkey, etc) by multiple subcutaneous or intraperitoneal injections of EVP1 protein (a purified peptide fragment, full-length recombinant protein, fusion protein, etc.) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against EVP1 is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239:1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies. Bispecific antibodies are antibodies that are capable of specifically recognizing and binding at least two different epitopes. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

IV. Kits

In yet other embodiments, the present invention provides kits for the detection and characterization of *Plasmodium* infection. In some embodiments, the kits contain antibodies specific for EVP1, in addition to detection reagents and buffers. In other embodiments, the kits contain reagents specific for the detection of nucleic acid (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins. The kit can comprise, for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In other embodiments the kit comprises pairs of primers for detecting EVP1 nucleic acid.

EXPERIMENTAL

The following examples are provided in order to demonstrate and further illustrate certain preferred embodiments and aspects of the present invention and are not to be construed as limiting the scope thereof.

Sequence data for *P. falciparum* Ghanaian strain was obtained from The Sanger Institute website. Sequencing of *P. falciparum* Ghanaian strain was accomplished as part of the Malaria Genome Project with support by The Wellcome Trust. HB3 and Dd2 sequence information was provided by the *Plasmodium falciparum* Sequencing Project Broad Institute of Harvard and MIT. PlasmoDB provided additional sequence information and transcriptional plots. These sequences are incorporated herein by reference in their entireties.

Example 1

Transcriptional Response to PPMP Treatment by Microarrays

Ring stage parasites were treated with either 5 µM dl-threo-PPMP or vehicle ([ethanol]f=0.01%) for 24 hr and were harvested for RNA isolation. Untreated ring stage parasites were also harvested. The experimental design served to compare PPMP— to either mock-treated or ring stage transcripts. RNA was isolated according to Invitrogen (Carlsbad, Calif.) protocols using Trizol. First strand cDNA synthesis and hybridizations were performed according to previous protocols[24]. Microarray slides were scanned using GenePix 4000B Scanner and analyzed with GenePix Pro 4.1. The statistical program R with the add-in package SMA (http://www.fol-lowed by stat.berkeley.edu/%7Eterry/zarray/Software/sma-code.html) was used to normalize data[25,26]. Only high quality features and those with signal two standard deviations above background were analyzed, leaving 4580 elements from a total of 8088 oligos. Features with a log odds ratio above zero were considered.

Example 2

Transfection Using PiggyBac Type II Transposable Element

Full length PFD0495c (gi 23510091]) was amplified from gDNA using the oligos 5'-aaaaagcaggettcgaaggagatagaac-catgATGTATAAGAAATGTTTCATTTTATATCCTATC TTTTTTC-3' (SEQ ID NO:29) and 5'-agaaagctgggtcT-CATCTGTCGTCGGAACG GAAGGAATC-3'(SEQ ID NO:30) (partial attB sites in lower case). Cloning with the Gateway system was according to Invitrogen protocols. To make the destination vector, the dhfr gene with control regions and PfCAM promoter and PfHSP86 3' UTR was ligated to pXL-BAC-HH14, which contained OriC, the ampicillin resistance gene and the IR and TR sequences. The transposase plasmid was described previously[14].

Both integration and transposase plasmids (100 µg each) were simultaneously electroporated into erythrocytes. Forty-eight hours after transfection, selection with 2.5 nM WR99210 was initiated. After 11 days of selection, GFP-expressing parasites were detected. GFP-expressing parasites were then cloned by limiting dilution at 0.2 parasites/well in a 96-well plate. Fresh media and 1% hematocrit were added at days 6 and 13, and at day 17 parasitemia of each well was determined by examining thick smears stained by Giemsa.

Example 3

Determination of PFD0495c-GFP Topology Using Tetanolysin

Selective permeabilization of the erythrocyte plasma membrane using tetanolysin was performed according to published protocols[27]. Erythrocytes infected with PFD0495c-GFP expressing parasites (38-42-h post-invasion) were probed with antibodies to GFP (Molecular Probes) or MSP1 (Anthony Holder) and appropriate secondary antibodies conjugated to rhodamine or Cy-5. Cells were viewed using DeltaVision Deconvolution microscopy as described[10]. A high-resolution 3-D image was captured with an Olympus IX inverted fluorescence microscope and a Photometrix cooled CCD camera (CH350/LCCD) driven by DeltaVision software (softWoRx) from Applied Precision Inc (Seattle, Wash.). Twelve to fifteen 200 nm optical sections were taken through the depth of the cell, and DeltaVision software was used to deconvolve images and reconstruct a 3-D view.

Example 4

Expression of GST Fusions

To produce recombinant GST-PFD0495c cargo, the C-terminus (amino acids 795 to 833) was amplified using oligonucleotides 5'-aaaaagcaggcttcGATTTAGATATTGATG ATACTTTAAAGTTTCAGCATGATCAA-3' (SEQ ID NO:31) and 5'-agaaagctgggtcTCATCTGTCGTCG-GAACGGAAGGAATC-3' (SEQ ID NO:32) and the repeat region (amino acids 268 to 389) was amplified with 5'-aaaaagcaggcttcGATGATGTGGT GAGAAATATTAAC-GATGATGTG-3' (SEQ ID NO:33) and 5'-agaaagctgggtcT-CAAC TATTATTAGTTTTTATATCACCTGCAT-TATTCTTTTTATCATTATA-3' (SEQ ID NO:34) (partial attB sites in lowercase). To produce GST-SBP cargo, the C-terminus of SBP (amino acids 239 to 337) was amplified using oligos 5'-aaaaagcaggcttcGGAAAAAGAAAAG GATATTACCTAGCAAAAAAAC-3' (SEQ ID NO:35) and 5' agaaagctgggtcTTAAGGTTTC TCTAGCAACT-GTTTTTGTTGTGG-3' (SEQ ID NO:36).

Cloning into the Gateway system was performed with pDEST15 (Invitrogen). Expression of recombinant fusions was induced with 1 mM Isopropyl-(beta)-D-thiogalactopyra-noside (IPTG) (Eppendorf) for 2 h at 37° C. Protein purification was performed with glutathione resin (Clontech) in non-denaturing buffer containing 50 mM NaCl, 50 mM Tris, 5 mM EDTA, pH 8.

Example 5

Loading GST-fusions into Erythrocyte Cytoplasm and Subsequent Infection by *Plasmodium falciparum*

Erythrocytes were loaded with GST cargo and resealed according to previous protocols[15]. Schizonts were percoll-purified to >95% purity and mixed with loaded ghosts at 2% parasitemia. Numbers of rings, trophozoites and schizonts were enumerated by a counter who was blinded to sample identity. Parasite morphology was monitored for any differences. Images of blood smears were taken by light microscopy with a Zeiss Axioskop upright microscope and Nuance spectral camera/un-mixing system (Cambridge Research and Instrumentation).

Example 6

Immunofluorescence Assay

Indirect immunofluorescence assay was conducted as described[27]. Ghosts that were infected with 3D7 were probed with antibodies to HRPII (Santa Cruz) and MSP1 (MR4) and appropriate secondary antibodies conjugated to FITC or rhodamine. Nuclei were stained with 10 µg/mL Hoechst 33342. Images were captured using DeltaVision Deconvolution microscopy as described[10].

Example 7

Monitoring Endocytic Lipid Import with the Lipid Marker FM4-64

FM4-64 (N-(3-triethylammoniumpropyl)-4-(6-(4-(diethylamino)phenyl)hexatrienyl)pyridinium dibromide) is a fluorescent lipid marker that has been used to study endocytosis in eukaryotic cells[18]. To visualize active uptake of FM4-64 from the erythrocyte plasma membrane during intraerythrocytic growth, trophozoite stage parasites expressing either PfHRPII-GFP or PFD0495c-GFP were incubated in the absence or presence of 5 µM dl-threo-PPMP for 30 min at 37° C. Infected erythrocytes were washed three times in PBS then stained with 16 µM FM4-64 for 30 min at 37° C. Nuclei were stained with 10 µg/mL Hoechst 33342, and cells were washed with PBS three times. Cells were imaged live with DeltaVision Deconvolution microscopy[10].

Example 8

Visualization of Tubo-vesicular Network by BODIPY-Texas Red C5 Ceramide Staining To visualize TVN membranes, erythrocytes or ghosts infected with indicated *P. falciparum* strain were washed free of serum and stained with 2.5 µM BODIPY-Texas Red C5 ceramide (N-((4-(4,4-difluoro-5-(2-thienyl)-4-bora-3a,4a-diaza-s-indacene-3-yl)phenoxy)acetyl)sphingosine, Invitrogen) for 15 min at 37° C. Nuclei were stained with 10 µg/mL Hoechst 33342. The cells were washed in RPMI 1640 three times and viewed live by DeltaVision Deconvolution microscopy as described[9].

Example 9

Protease Treatments

Intact infected erythrocytes in serum-free RPMI were treated with 1 mg/ml of trypsin (Sigma) in ice for 30 min. Trypsin inactivation was carried out by adding an equal volume of PBS containing 20 µg/ml soybean trypsin inhibitor and protease inhibitor cocktail (Roche) and incubating at 4° C. for 5 min. Samples were analyzed in western blots with the indicated antibodies. Anti-peptide antibodies were raised in rabbits against the PFD0495c peptide LKFQHDQEFLNYFKRYQDFN (SEQ ID NO:17) (NeoMPS, San Diego, Calif.).

Example 10

Immunogenicity of PFD0495c Repeat Region

GST fusions of the repeat sequence as well at the C-terminal domain of CESA-1 were expressed. In Western blots they were separated and probed with antibodies to pooled adult, human immune sera from southwest Cameroon.

Example 11

Quantitative RT-PCR

Quantitative PCR was used to confirm the array results. Parasites were synchronized by successive rounds of percoll and sorbitol. Ring stage parasites were treated with either 5 µM dl-threo-PPMP or vehicle (ethanol=0.01%) for 3, 6, 12, and 24 h. RNA was isolated using Trizol (Invitrogen) and treated with DNAse (Promega) according the manufacturer's recommendations. Integrity of the RNA was confirmed with the 2100 Bioanalyzer (Agilent). First strand cDNA synthesis was initiated by priming 5 ug RNA with 40 ug/mL oligo(dT) 12-18 at 65° C. for 5 min then incubating reaction with 0.5 mM dNTPs and 200 U SuperScript reverse transcriptase (Invitrogen) for 60 min at 42° C. The reaction was inactivated by heating to 70° C. for 15 min. Each qRT-PCR reaction, done in triplicate, contained 1 ng cDNA, 2 µM primers (forward 5'-GCTCTTTCCATAAATACTGTATT-3' (SEQ ID NO:37), reverse 5' ATGGCCAAACAACATCA-3' (SEQ ID NO:38) and SYBR green chemistry (Applied Biosystems) and was done using the 7900HT ABI system according to ABI protocols.

Amplification of *P. falciparum* 18S ribosomal RNA (GI 160642), an endogenous control, was done in parallel (forward 5'-ACAATTGGAGGGCAAGT-'3 (SEQ ID NO:39), reverse 5'-TTGGAGCTGGAATTACC-3' (SEQ ID NO:40)) to standardize the amount of sample in each well. A control reaction that did not receive reverse transcriptase was included to account for non-specific amplification due to contaminating DNA. Relative quantification was performed using the comparative method, whereby the amount of PFD0495c was normalized to the endogenous control 18S rRNA. Control samples receiving only vehicle were used to calibrate each PPMP sample at that time point.

Example 12

PiggyBac Insertion Site Analysis

To confirm integration into the genome, Southern analysis was performed, digesting 2 ug DNA (either gDNA or plasmid) with 10 units of either BglII or EcoRV. The coding sequence of hdhfr labeled with $^{32}$P was used as a probe. No episomes were maintained, and only one insertion was detected for both clones 1 and 2 of PFD0495c-GFP. PiggyBac insertion sites in the genome were identified by using an adaptor ligation-mediated PCR method. Briefly, Rsa I digested genomic DNA was ligated to compatible adaptors and used in a PCR reaction with an internal piggyBac primer and a primer in the adaptor. The PCR products obtained were then directly sequenced to identify the insertion sites. Insertion of the expression cassette within the piggyBac Inverted Terminal Repeats occurred in chromosome 12 between loci PFL1425w (T complex protein) and PFL1430c (hypothetical protein).

Example 13

Western Blots to Confirm Expression and Membrane Association of PFD0495c-GFP To confirm expression of the GFP linked transgene, Western blots of the cloned line were analyzed. Total parasite lysates (5×105 parasites) were blotted and probed with antibodies to GFP (Molecular Probes) and peroxidase-conjugated secondary (Bio-Rad). Because PFD0495c has a predicted transmembrane domain, the solubility of the transgene by hypotonic lysis was tested. Schizont pellets were lysed in 100 volumes of water supplemented with a cocktail of protease inhibitors (Roche) and centrifuged at 95,000 rpm for 15 minutes to separate membrane from soluble fractions. Pellet and supernatant fractions (parasite equivalents of 5×105) were blotted and probed with anti-GFP antibody followed by peroxidase-conjugated secondary antibody.

Example 14

Growth of PFD0495c-GFP Transgenic Line and 3D7

To compare growth of PFD0495c-GFP expressing parasites to 3D7, Giemsa stained blood smears were counted to determine numbers of rings, trophozoites and schizonts. Percoll-purified schizonts were mixed with erythrocytes at ~2% parasitemia in 2% hematocrit. Blood smears were made every 24 hr from day 0 to 4, and medium was changed daily. At day 2 ring stage parasites were subcultured to 3% parasitemia. The experiment was conducted in duplicate, and the counter was blinded to sample identity. There were no detectable differences in growth among the uncloned population, clone 1 PFD0495c-GFP, and 3D7 parasites.

Example 15

Measurements of IC50 and IC90 of PPMP in PFD0495c-GFP Transgenic Line and 3D7 Strains Previous studies showed that PPMP is a sphingolipid analog that inhibits an essential parasite sphingomyelin synthase (PfSMS) activity exported to the erythrocyte and after 36 h of treatment, the effects of this inhibitor are cidal with low micromolar concentrations inhibiting 50% and 90% parasite growth[12]. A change in activity levels of exported PfSMS activity is thus expected to be reflected in the IC50 and/or IC90. Hence, the concentrations to inhibit 50% and 90% growth in parent and transgenic lines were determined by standard hypoxanthine incorporation assay (12). Synchronized ring stage parasites were treated with PPMP over a concentration range of 0.02-20 uM at 0.6% pst and 1% hct in hypoxanthine-free CRPMI. After incubating for 24 hr, 0.5 uCi [8-$^3$H]Hypoxanthine (GE Biosciences) was added to each well. After an 18 hr incubation infected erythrocytes were harvested onto glass fiber filters, which were dried and counted. All data were regressed using the logistic dose response function of Tablecurve 2D software.

Example 16

Reversibility of Treatment with PPMP after 24 Hr

Synchronized ring stage parasites at 5-10% pst were incubated with 5 uM PPMP for 24 hr (day 1). Infected erythrocytes were washed with RPMI 1640 three times to remove PPMP then put back into culture. Blood smears were made at days 0, 1, 2, and 3 and stained with Giemsa. Parasites were fed fresh media every 24 hr. Rings, trophozoites and schizonts were enumerated by a counter who was blinded to sample identity. Both PFD0495c-GFP clones responded to PPMP in the same manner as 3D7. After a 24 incubation with PPMP, 3D7 parasites and both PFD0495c-GFP clones remained at the trophozoite stage rather than progressing to schizonts. When PPMP was washed out, all parasites continued the cell cycle and at day 2 matured to schizonts, which formed new rings by day 3.

Example 17

In vivo Treatment

Mice were pretreated treated with the extracellular portion of the protein (PFD0495c). These mice were more resistant to subsequent infection.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references are herein incorporated by reference as if fully set forth herein.
1. Miller, L. H., Baruch, D. I., Marsh, K. & Doumbo, O. K. The pathogenic basis of malaria. *Nature* 415, 673-9 (2002).
2. Haldar, K., Murphy, S. C., Milner, D. A., Jr. & Taylor, T. E. Malaria: Mechanisms of Erythrocytic Infection and Pathological Correlates of Severe Disease. *Annual Review of Pathology: Mechanisms of Disease* 2, 217-249 (2007).
3. Hiller, N. L. et al. A host-targeting signal in virulence proteins reveals a secretome in malarial infection. *Science* 306, 1934-7 (2004).
4. Marti, M., Good, R. T., Rug, M., Knuepfer, E. & Cowman, A. F. Targeting malaria virulence and remodeling proteins to the host erythrocyte. *Science* 306, 1930-3 (2004).
5. Jeffares, D. C. et al. Genome variation and evolution of the malaria parasite *Plasmodium falciparum*. *Nat Genet.* 39, 120-5 (2007).
6. Mu, J. et al. Genome-wide variation and identification of vaccine targets in the *Plasmodium falciparum* genome. *Nat Genet.* 39, 126-30 (2007).
7. Volkman, S. K. et al. A genome-wide map of diversity in *Plasmodium falciparum*. *Nat Genet.* 39, 113-9 (2007).
8. Craig, A. & Scherf, A. Molecules on the surface of the *Plasmodium falciparum* infected erythrocyte and their role in malaria pathogenesis and immune evasion. *Mol Biochem Parasitol* 115, 129-43 (2001).
9. Pleass, R. J. & Holder, A. A. Opinion: antibody-based therapies for malaria. *Nat Rev Microbiol* 3, 893-9 (2005).
10. Lauer, S. et al. Vacuolar uptake of host components, and a role for cholesterol and sphingomyelin in malarial infection. *Embo J* 19, 3556-64 (2000).
11. Lauer, S. A., Rathod, P. K., Ghori, N. & Haldar, K. A membrane network for nutrient import in red cells infected with the malaria parasite. *Science* 276, 1122-5 (1997).
12. Lauer, S. A., Ghori, N. & Haldar, K. Sphingolipid synthesis as a target for chemotherapy against malaria parasites. *Proc Natl Acad Sci USA* 92, 9181-5 (1995).
13. Sargeant, T. J. et al. Lineage-specific expansion of proteins exported to erythrocytes in malaria parasites. *Genome Biol* 7, R12 (2006).
14. Balu, B., Shoue, D. A., Fraser, M. J., Jr. & Adams, J. H. High-efficiency transformation of *Plasmodium falciparum* by the lepidopteran transposable element piggyBac. *Proc Natl Acad Sci USA* 102, 16391-6 (2005).
15. Murphy, S. C. et al. Erythrocyte G protein as a novel target for malarial chemotherapy. *PLoS Med* 3, e528 (2006).
16. Pei, X. et al. The ring-infected erythrocyte surface antigen (RESA) of *Plasmodium falciparum* stabilizes spectrin tetramers and suppresses further invasion. *Blood* 110, 1036-42 (2007).

17. Cooke, B. M. et al. A Maurer's cleft-associated protein is essential for expression of the major malaria virulence antigen on the surface of infected red blood cells. *J Cell Biol* 172, 899-908 (2006).
18. Vida, T. A. & Emr, S. D. A new vital stain for visualizing vacuolar membrane dynamics and endocytosis in yeast. *J Cell Biol* 128, 779-92 (1995).
19. Rasti, N., Wahlgren, M. & Chen, Q. Molecular aspects of malaria pathogenesis. *FEMS Immunol Med Microbiol* 41, 9-26 (2004).
20. Voss, T. S. et al. A var gene promoter controls allelic exclusion of virulence genes in *Plasmodium falciparum* malaria. *Nature* 439, 1004-8 (2006).
21. Dzikowski, R., Frank, M. & Deitsch, K. Mutually exclusive expression of virulence genes by malaria parasites is regulated independently of antigen production. *PLoS Pathog* 2, e22 (2006).
22. Mehlin, C. et al. Heterologous expression of proteins from *Plasmodium falciparum*: results from 1000 genes. *Mol Biochem Parasitol* 148, 144-60 (2006).
23. Gardner, M. J. et al. Genome sequence of the human malaria parasite *Plasmodium falciparum*. *Nature* 419, 498-511 (2002).
24. Bozdech, Z. et al. Expression profiling of the schizont and trophozoite stages of *Plasmodium falciparum* with a long-oligonucleotide microarray. *Genome Biol* 4, R9 (2003).
25. Lonnstedt, I. & Speed, T. P. Replicated microarray data. *Statistica Sinica* 12, 31-46 (2002).
26. Yang, Y. H. et al. Normalization for cDNA microarray data: a robust composite method addressing single and multiple slide systematic variation. *Nucleic Acids Res* 30, e15 (2002).
27. Hiller, N. L., Akompong, T., Morrow, J. S., Holder, A. A. & Haldar, K. Identification of a stomatin orthologue in vacuoles induced in human erythrocytes by malaria parasites: A role for microbial raft-proteins in apicomplexan vacuole biogenesis. *J Biol Chem*, 48413-48421 (2003).
28. K. Haldar, M. A. Ferguson, G. A. Cross, *J Biol Chem* 260, 4969-4974 (1985).
29. W. Trager, J. B. Jensen, *Science* 193, 673-675 (1976).
30. R. Higuchi, C. Fockler, G. Dollinger, R. Watson, *Biotechnology (NY)* 11, 1026-1030 (1993).
31. S. A. Desai, S. M. Bezrukov, J. Zimmerberg, *Nature* 406, 1001-1005 (2000).

We claim:

1. A composition suitable for injection into a subject comprising: i) an adjuvant and/or physiological tolerable buffer, and ii) an isolated peptide consisting of the amino acid sequence SEQ ID NOs: 17 and 7-12.

2. The composition of claim 1, wherein said isolated peptide is conjugated to a hapten or other immune stimulating moiety.

3. A composition suitable for injection into a subject comprising: i) an adjuvant and/or physiological tolerable buffer, and ii) an isolated peptide consisting of the amino acid sequence SEQ ID NOs: 17 and 7-12, wherein said isolated peptide is conjugated to a hapten or other immune stimulating moiety.

* * * * *

SEQUENCE LISTING

```
<160> NUMBER OF SEQ ID NOS: 41

<210> SEQ ID NO 1
<211> LENGTH: 833
<212> TYPE: PRT
<213> ORGANISM: Plasmodium falciparum

<400> SEQUENCE: 1

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile Ile Ala Glu Tyr Cys Asp Thr Lys Lys Asn Glu Phe
        35                  40                  45

Phe Leu Gly Glu Ser Ile Leu Gly Ala Thr Ser Ser Arg Ser Thr Ser
    50                  55                  60

Leu Asn Ile Glu Gln Asn Lys Asn Thr Asn Ile Ile Lys Asp Lys Asn
65                  70                  75                  80

Glu Gln Ser Tyr Asp Glu His Ile Val Met Asn Pro Asn Thr Asn Arg
                85                  90                  95

Ala Leu Ser Ile Asn Thr Val Phe Asn Tyr Asn Lys Glu Asn Lys Glu
            100                 105                 110

Lys Lys Ile Phe Ser Phe Ser Glu Phe Pro Lys Glu Phe Asn Ile Leu
        115                 120                 125

Asp Val Val Trp Pro Tyr Met Lys Gln Pro Lys Glu Leu Phe Lys Lys
    130                 135                 140

Ser Ser Val Ile Thr Phe Leu Met Asp His Tyr Phe Arg His Glu Leu
145                 150                 155                 160

Tyr Ile Leu Glu Ser Arg Ile Ala Met Lys Pro Arg Arg Thr Tyr
                165                 170                 175

Glu Ala Pro Cys Phe Glu His Asp Phe Glu Leu Glu Arg Asp Phe
            180                 185                 190

Phe Phe Leu Glu Asp Cys Asp Glu Asp His Gln Phe Phe Asn Lys Tyr
        195                 200                 205

Lys Ser Tyr Phe Phe Ser Leu Asn Val Leu Asp His Cys Lys Ser Leu
```

```
                210                 215                 220
Arg Thr Lys Lys Gln Lys Cys Asn Asn Met Lys Asp Asp Glu Val Ser
225                 230                 235                 240

Asn Ile Asn Asp Asp Glu Val Ser Asn Ile Asn Asp Asp Glu Val Ser
                245                 250                 255

Asn Ile Asn Asp Asp Glu Val Ser Asn Ile Lys Asp Asp Val Val Arg
                260                 265                 270

Asn Ile Asn Asp Asp Val Val Arg Asn Ile Asn Asp Asp Glu Val His
                275                 280                 285

His Thr Asn Asp Asp Lys Val Asn His Thr Asn Asp Asp Lys Val Asn
                290                 295                 300

His Thr Asn Asp Asp Lys Val Asn His Thr Asn Asp Asp Lys Val Asn
305                 310                 315                 320

His Thr Asn Asp Asp Lys Val Asn His Thr Asn Asp Asp Asn Val Asn
                325                 330                 335

His Thr Asn Asp Asp Lys Val Asn His Thr Asn Asp Asp Lys Val Asn
                340                 345                 350

His Thr Asn Asp Asp Lys Val Asn His Thr Asn Asp Asp Lys Val Asn
                355                 360                 365

His Thr Asn Asn Tyr Tyr Asn Asp Lys Lys Asn Asn Ala Gly Asp Ile
                370                 375                 380

Lys Thr Asn Asn Ser Ile Arg Glu Glu Lys Lys Leu Glu His Pro Asp
385                 390                 395                 400

Arg Asn Ile Glu Lys Lys Ile Asp Leu Ile Thr Tyr Asn Lys Lys Arg
                405                 410                 415

Ile Glu Glu Tyr Tyr Asp Ser Ile Ile Ser Tyr Phe Phe Gly Leu Ile
                420                 425                 430

Ile Leu Tyr His Asn Lys Lys Glu Thr Asn Leu Asn Tyr Tyr Thr Lys
                435                 440                 445

Phe Leu Thr Leu Asp Lys Tyr Lys Asn Met Tyr Asn Cys Leu Asn Asn
450                 455                 460

Asp Ile Ser Lys Ile Tyr Glu Lys Ala Ile Leu Phe Ser His Glu Glu
465                 470                 475                 480

Phe Cys Ile Ile Gln Lys Lys Asp Leu Lys Pro His Gly Leu Arg Gly
                485                 490                 495

Asn Ile Lys Tyr Tyr Tyr Phe Phe Asn Arg Ile Val Ser Thr Ser Leu
                500                 505                 510

Tyr Leu Leu His Glu Ile Leu Gln Lys Leu Asp Gly Lys Met Tyr Thr
                515                 520                 525

Phe Gln Lys Leu Pro Leu Lys Ile Gln Asn His Leu Ile Asn Leu Pro
530                 535                 540

Asp Ile Arg Ile Lys Glu Ile Lys Lys Arg Met Arg Gln Gln Lys Lys
545                 550                 555                 560

Lys Asn Gln Asn Ser Leu Leu Glu Ser Ser Tyr Lys Asp Leu Tyr
                565                 570                 575

Tyr Val Ser Ser Glu Tyr Tyr Asp Tyr Val Ser Lys Cys Leu Ile Trp
                580                 585                 590

Ser Asn Tyr Tyr Phe Asn Tyr Met Ser Thr Thr Ile Val Tyr Ser
                595                 600                 605

Val Lys Lys Arg Ser Tyr Glu Tyr Ile Gln Lys Glu Lys Ser Lys Ile
                610                 615                 620

Asn Leu Phe Leu Glu Tyr Ala His Asn Asp Ile Ile Glu Tyr Ile Lys
625                 630                 635                 640
```

```
Asp Ile Thr Tyr Tyr Phe Lys Leu Ile Val Asn Lys Ile Glu Ser Lys
                645                 650                 655

Arg Leu Phe Ser Glu Pro Val Met Leu Cys Phe Gln Leu Phe Ser Asp
            660                 665                 670

His Tyr Leu Tyr Leu Leu Lys Asn Ile Leu Ser Ile Leu Leu Ile His
        675                 680                 685

Ile Glu Lys Pro Val Thr Arg Lys Ser Asn Arg Asp Leu Lys Lys Ile
    690                 695                 700

Phe Asn Cys Ile Lys Asp Gln Glu Asn Ile Thr Lys Asn Ile Leu Asp
705                 710                 715                 720

Glu Phe His Ser Lys Asn Lys Ile Arg Tyr Asn Pro Thr Glu Phe Leu
                725                 730                 735

Ile Tyr Lys Phe Phe Ser Ser Ile Gln Tyr Lys Gln Asn Ile Ala His
            740                 745                 750

Lys Tyr Ile Ile Gln Ser Asn Ile Asn Ile Ile Ser Leu Met Leu Lys
        755                 760                 765

Ile Phe Asn Tyr Phe His Ile Leu Val Ile Ser Leu Ile Phe Tyr Leu
    770                 775                 780

Asn Leu His Ser Met Tyr Thr Leu Phe Ile Asp Leu Asp Ile Asp Asp
785                 790                 795                 800

Thr Leu Lys Phe Gln His Asp Gln Glu Phe Leu Asn Tyr Phe Lys Arg
                805                 810                 815

Tyr Gln Asp Phe Asn Asn Gln Leu Phe Asp Ser Phe Arg Ser Asp Asp
            820                 825                 830

Arg

<210> SEQ ID NO 2
<211> LENGTH: 865
<212> TYPE: PRT
<213> ORGANISM: Plasmodium falciparum

<400> SEQUENCE: 2

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
                20                  25                  30

Phe Ser Arg Ile Ile Ala Glu Tyr Cys Asp Thr Lys Lys Asn Glu Phe
            35                  40                  45

Phe Leu Gly Glu Ser Ile Leu Gly Ala Thr Ser Ser Arg Ser Thr Ser
        50                  55                  60

Leu Asn Ile Glu Gln Asn Lys Asn Thr Asn Ile Ile Lys Asp Lys Asn
65                  70                  75                  80

Glu Gln Ser Tyr Asp Glu His Ile Val Met Asn Pro Asn Thr Asn Arg
                85                  90                  95

Ala Leu Ser Ile Asn Thr Val Phe Asn Tyr Asn Lys Glu Asn Lys Glu
            100                 105                 110

Lys Lys Ile Phe Ser Phe Ser Glu Phe Pro Lys Glu Phe Asn Ile Leu
        115                 120                 125

Asp Val Val Trp Pro Tyr Met Lys Gln Pro Lys Glu Leu Phe Lys Lys
    130                 135                 140

Ser Ser Val Ile Thr Phe Leu Met Asp His Tyr Phe Arg His Glu Leu
145                 150                 155                 160

Tyr Ile Leu Glu Ser Arg Ile Ala Met Lys Pro Arg Arg Arg Thr Tyr
                165                 170                 175
```

```
Glu Ala Pro Cys Phe Glu His Asp Asp Phe Glu Leu Glu Arg Asp Phe
            180                 185                 190

Phe Phe Leu Glu Asp Cys Asp Glu Asp His Gln Phe Phe Asn Lys Tyr
        195                 200                 205

Lys Ser Tyr Phe Phe Ser Leu Asn Val Leu Asp His Cys Lys Ser Leu
    210                 215                 220

Arg Thr Lys Lys Gln Lys Cys Asn Asn Met Lys Asp Asp Glu Val Ser
225                 230                 235                 240

Asn Ile Asn Asp Asp Glu Val Ser Asn Ile Asn Asp Asp Glu Val Ser
                245                 250                 255

Asn Ile Asn Asp Asp Glu Val Ser Asn Ile Lys Asp Asp Val Val Arg
            260                 265                 270

Asn Ile Asn Asp Asp Val Val Arg Asn Ile Asn Asp Asp Val Val Arg
        275                 280                 285

Asn Ile Asn Asp Asp Glu Val His His Thr Asn Asp Asp Asn Val Asn
        290                 295                 300

His Thr Asn Asp Asp Lys Val Asn His Thr Asn Asp Asp Lys Val Asn
305                 310                 315                 320

His Thr Asn Asp Asp Lys Val Asn His Thr Asn Asp Asp Lys Val Asn
                325                 330                 335

His Thr Asn Asp Asp Lys Val Asn His Thr Asn Asp Asp Lys Val Asn
            340                 345                 350

His Thr Asn Asp Asp Lys Val Asn His Thr Asn Asp Asp Lys Val Asn
        355                 360                 365

His Thr Asn Asp Asp Lys Val Asn His Thr Asn Asp Asp Lys Val Asn
        370                 375                 380

His Thr Asn Asp Asp Asn Val Asn His Thr Asn Asp Asp Lys Val Asn
385                 390                 395                 400

His Thr Asn Asn Tyr Tyr Asn Asp Lys Lys Asn Asn Ala Gly Asp Ile
                405                 410                 415

Lys Thr Asn Asn Ser Ile Arg Glu Glu Lys Lys Leu Glu His Pro Asp
            420                 425                 430

Arg Asn Ile Glu Lys Lys Ile Asp Leu Ile Thr Tyr Asn Lys Lys Arg
        435                 440                 445

Ile Glu Glu Tyr Tyr Asp Ser Ile Ile Ser Tyr Phe Phe Gly Leu Ile
        450                 455                 460

Ile Leu Tyr His Asn Lys Lys Glu Thr Asn Leu Asn Tyr Tyr Thr Lys
465                 470                 475                 480

Phe Leu Thr Leu Asp Lys Tyr Lys Asn Met Tyr Asn Cys Leu Asn Asn
                485                 490                 495

Asp Ile Ser Lys Ile Tyr Glu Lys Ala Ile Leu Phe Ser His Glu Glu
            500                 505                 510

Phe Cys Ile Ile Gln Lys Lys Asp Leu Lys Pro His Gly Leu Arg Gly
        515                 520                 525

Asn Ile Lys Tyr Tyr Phe Phe Asn Arg Ile Val Ser Thr Ser Leu
        530                 535                 540

Tyr Leu Leu His Glu Ile Leu Gln Lys Leu Asp Gly Lys Met Tyr Thr
545                 550                 555                 560

Phe Gln Lys Leu Pro Leu Lys Ile Gln Asn His Leu Ile Asn Leu Pro
                565                 570                 575

Asp Ile Arg Ile Lys Glu Ile Lys Lys Arg Met Arg Gln Gln Lys Lys
            580                 585                 590
```

-continued

Lys Asn Gln Asn Ser Leu Leu Glu Ser Ser Tyr Lys Asp Leu Tyr
            595                 600                 605

Tyr Val Ser Ser Glu Tyr Asp Tyr Val Ser Lys Cys Leu Ile Trp
        610                 615                 620

Ser Asn Tyr Tyr Phe Phe Asn Tyr Met Ser Thr Thr Ile Val Tyr Ser
625                 630                 635                 640

Val Lys Lys Arg Ser Tyr Glu Tyr Ile Gln Lys Glu Lys Ser Lys Ile
                645                 650                 655

Asn Leu Phe Leu Glu Tyr Ala His Asn Asp Ile Ile Glu Tyr Ile Lys
            660                 665                 670

Asp Ile Thr Tyr Tyr Phe Lys Leu Ile Val Asn Lys Ile Glu Ser Lys
        675                 680                 685

Arg Leu Phe Ser Glu Pro Val Met Leu Cys Phe Gln Leu Phe Ser Asp
    690                 695                 700

His Tyr Leu Tyr Leu Leu Lys Asn Ile Leu Ser Ile Leu Leu Ile His
705                 710                 715                 720

Ile Glu Lys Pro Val Thr Arg Lys Ser Asn Arg Asp Leu Lys Lys Ile
                725                 730                 735

Phe Asn Cys Ile Lys Asp Gln Glu Asn Ile Thr Lys Asn Ile Leu Asp
            740                 745                 750

Glu Phe His Ser Lys Asn Lys Ile Arg Tyr Asn Pro Thr Glu Phe Leu
        755                 760                 765

Ile Tyr Lys Phe Phe Ser Ser Ile Gln Tyr Lys Gln Asn Ile Ala His
    770                 775                 780

Lys Tyr Ile Ile Gln Ser Asn Ile Asn Ile Ile Ser Leu Met Leu Lys
785                 790                 795                 800

Ile Phe Asn Tyr Phe His Ile Leu Val Ile Ser Leu Ile Phe Tyr Leu
                805                 810                 815

Asn Leu His Ser Met Tyr Thr Leu Phe Ile Asp Leu Asp Ile Asp Asp
            820                 825                 830

Thr Leu Lys Phe Gln His Asp Gln Glu Phe Leu Asn Tyr Phe Lys Arg
        835                 840                 845

Tyr Gln Asp Phe Asn Asn Gln Leu Phe Asp Ser Phe Arg Ser Asp Asp
    850                 855                 860

Arg
865

<210> SEQ ID NO 3
<211> LENGTH: 833
<212> TYPE: PRT
<213> ORGANISM: Plasmodium falciparum

<400> SEQUENCE: 3

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile Ile Ala Glu Tyr Cys Asp Thr Lys Lys Asn Glu Phe
        35                  40                  45

Phe Leu Gly Glu Ser Ile Leu Gly Ala Thr Ser Arg Ser Thr Ser
    50                  55                  60

Leu Asn Ile Glu Gln Asn Lys Asn Thr Asn Ile Ile Lys Asp Lys Asn
65                  70                  75                  80

Glu Gln Ser Tyr Asp Glu His Ile Val Met Asn Pro Asn Thr Asn Arg
                85                  90                  95

```
Ala Leu Ser Ile Asn Thr Val Phe Asn Tyr Asn Lys Glu Asn Lys Glu
                100                 105                 110
Lys Lys Ile Phe Ser Phe Ser Glu Phe Pro Lys Glu Phe Asn Ile Leu
            115                 120                 125
Asp Val Val Trp Pro Tyr Met Lys Gln Pro Lys Glu Leu Phe Lys Lys
130                 135                 140
Ser Ser Val Ile Thr Phe Leu Met Asp His Tyr Phe Arg His Glu Leu
145                 150                 155                 160
Tyr Ile Leu Glu Ser Arg Ile Ala Met Lys Pro Arg Arg Thr Tyr
                165                 170                 175
Glu Ala Pro Cys Phe Glu His Asp Asp Phe Glu Leu Gly Arg Asp Phe
                180                 185                 190
Phe Phe Leu Glu Asp Cys Asp Glu Asp His Gln Phe Phe Asn Lys Tyr
            195                 200                 205
Lys Ser Tyr Phe Phe Ser Leu Asn Val Leu Asp His Cys Lys Ser Leu
            210                 215                 220
Arg Thr Lys Lys Gln Lys Cys Asn Asn Met Lys Asp Asp Glu Val Ser
225                 230                 235                 240
Asn Ile Asn Asp Asp Glu Val Ser Asn Ile Asn Asp Asp Glu Val Ser
                245                 250                 255
Asn Ile Asn Asp Asp Glu Val Ser Asn Ile Lys Asp Asp Val Val Arg
            260                 265                 270
Asn Ile Asn Asp Asp Val Val Arg Asn Ile Asn Asp Asp Glu Val His
            275                 280                 285
His Thr Asn Asp Asp Lys Val Asn His Thr Asn Asp Asp Lys Val Asn
            290                 295                 300
His Thr Asn Asp Asp Lys Val Asn His Thr Asn Asp Asp Lys Val Asn
305                 310                 315                 320
His Thr Asn Asp Asp Lys Val Asn His Thr Asn Asp Asp Asn Val Asn
                325                 330                 335
His Thr Asn Asp Asp Lys Val Asn His Thr Asn Asp Asp Lys Val Asn
            340                 345                 350
His Thr Asn Asp Asp Lys Val Asn His Thr Asn Asp Asp Lys Val Asn
            355                 360                 365
His Thr Asn Asn Tyr Tyr Asn Asp Lys Lys Asn Asn Ala Gly Asp Ile
            370                 375                 380
Lys Thr Asn Asn Ser Ile Arg Glu Glu Lys Lys Leu Glu His Pro Asp
385                 390                 395                 400
Arg Asn Ile Glu Lys Lys Ile Asp Leu Ile Thr Tyr Asn Lys Lys Arg
                405                 410                 415
Ile Glu Glu Tyr Tyr Asp Ser Ile Ile Ser Tyr Phe Phe Gly Leu Ile
                420                 425                 430
Ile Leu Tyr His Asn Lys Lys Glu Thr Asn Leu Asn Tyr Tyr Thr Lys
            435                 440                 445
Phe Leu Thr Leu Asp Lys Tyr Lys Asn Met Tyr Asn Cys Leu Asn Asn
            450                 455                 460
Asp Ile Ser Lys Ile Tyr Glu Lys Ala Ile Leu Phe Ser His Glu Glu
465                 470                 475                 480
Phe Cys Ile Ile Gln Lys Lys Asp Leu Lys Pro His Gly Leu Arg Gly
                485                 490                 495
Asn Ile Lys Tyr Tyr Tyr Phe Phe Asn Arg Ile Val Ser Thr Ser Leu
                500                 505                 510
```

```
Tyr Leu Leu His Glu Ile Leu Gln Lys Leu Asp Gly Lys Met Tyr Thr
            515                 520                 525

Phe Gln Lys Leu Pro Leu Lys Ile Gln Asn His Leu Ile Asn Leu Pro
530                 535                 540

Asp Ile Arg Ile Lys Glu Ile Lys Lys Arg Met Arg Gln Gln Lys Lys
545                 550                 555                 560

Lys Asn Gln Asn Ser Leu Leu Glu Ser Ser Ser Tyr Lys Asp Leu Tyr
            565                 570                 575

Tyr Val Ser Ser Glu Tyr Tyr Asp Tyr Val Ser Lys Cys Leu Ile Trp
            580                 585                 590

Ser Asn Tyr Tyr Phe Phe Asn Tyr Met Ser Thr Thr Ile Val Tyr Ser
            595                 600                 605

Val Lys Lys Arg Ser Tyr Glu Tyr Ile Gln Lys Glu Lys Ser Lys Ile
            610                 615                 620

Asn Leu Phe Leu Glu Tyr Ala His Asn Asp Ile Ile Glu Tyr Ile Lys
625                 630                 635                 640

Asp Ile Thr Tyr Tyr Phe Lys Leu Ile Val Asn Lys Ile Glu Ser Lys
            645                 650                 655

Arg Leu Phe Ser Glu Pro Val Met Leu Cys Phe Gln Leu Phe Ser Asp
            660                 665                 670

His Tyr Leu Tyr Leu Leu Lys Asn Ile Leu Ser Ile Leu Leu Ile His
            675                 680                 685

Ile Glu Lys Pro Val Thr Arg Lys Ser Asn Arg Asp Leu Lys Lys Ile
            690                 695                 700

Phe Asn Cys Ile Lys Asp Gln Glu Asn Ile Thr Lys Asn Ile Leu Asp
705                 710                 715                 720

Glu Phe His Ser Lys Asn Lys Ile Arg Tyr Asn Pro Thr Glu Phe Leu
            725                 730                 735

Ile Tyr Lys Phe Phe Ser Ser Ile Gln Tyr Lys Gln Asn Ile Ala His
            740                 745                 750

Lys Tyr Ile Ile Gln Ser Asn Ile Asn Ile Ile Ser Leu Met Leu Lys
            755                 760                 765

Ile Phe Asn Tyr Phe His Ile Leu Val Ile Ser Leu Ile Phe Tyr Leu
            770                 775                 780

Asn Leu His Ser Met Tyr Thr Leu Phe Ile Asp Leu Asp Ile Asp Asp
785                 790                 795                 800

Thr Leu Lys Phe Gln His Asp Gln Glu Phe Leu Asn Tyr Phe Lys Arg
            805                 810                 815

Tyr Gln Asp Phe Asn Asn Gln Leu Phe Asp Ser Phe Arg Ser Asp Asp
            820                 825                 830

Arg

<210> SEQ ID NO 4
<211> LENGTH: 849
<212> TYPE: PRT
<213> ORGANISM: Plasmodium falciparum

<400> SEQUENCE: 4

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile Ile Ala Glu Tyr Cys Asp Thr Lys Lys Asn Glu Phe
        35                  40                  45
```

-continued

Phe Leu Gly Glu Ser Ile Leu Gly Ala Thr Ser Ser Arg Ser Thr Ser
    50              55                  60

Leu Asn Ile Glu Gln Asn Lys Asn Thr Asn Ile Ile Lys Asp Lys Asn
65              70                  75                  80

Glu Gln Ser Tyr Asp Glu His Ile Val Met Asn Pro Asn Thr Asn Arg
                85                  90                  95

Ala Leu Ser Ile Asn Thr Val Phe Asn Tyr Asn Lys Glu Asn Lys Glu
                100                 105                 110

Lys Lys Ile Phe Ser Phe Ser Glu Phe Pro Lys Glu Phe Asn Ile Leu
            115                 120                 125

Asp Val Val Trp Pro Tyr Met Lys Gln Pro Lys Glu Leu Phe Lys Lys
130                 135                 140

Ser Ser Val Ile Thr Phe Leu Met Asp His Tyr Phe Arg His Glu Leu
145                 150                 155                 160

Tyr Ile Leu Glu Ser Arg Ile Ala Met Lys Pro Arg Arg Arg Thr Tyr
                165                 170                 175

Glu Ala Pro Cys Phe Glu His Asp Asp Phe Glu Leu Gly Arg Asp Phe
            180                 185                 190

Phe Phe Leu Glu Asp Cys Asp Glu Asp His Gln Phe Phe Asn Lys Tyr
        195                 200                 205

Lys Ser Tyr Phe Phe Ser Leu Asn Val Leu Asp His Cys Lys Ser Leu
    210                 215                 220

Arg Thr Lys Lys Gln Lys Cys Asn Asn Met Lys Asp Asp Glu Val Ser
225                 230                 235                 240

Asn Ile Ser Asp Asp Glu Val Ser Asn Ile Lys Asp Asp Glu Val Ser
                245                 250                 255

Asn Ile Lys Asp Asp Val Val Arg Asn Ile Asn Asp Asp Val Val Arg
            260                 265                 270

Asn Ile Asn Asp Asp Val Val Arg Asn Ile Asn Asp Asp Val Val Arg
        275                 280                 285

Asn Ile Asn Asp Asp Glu Val His His Thr Asn Asp Asp Asn Val Asn
    290                 295                 300

His Thr Asn Asp Asp Lys Val Asn His Thr Asn Asp Asp Lys Val Asn
305                 310                 315                 320

His Thr Asn Asp Asp Lys Val Asn His Thr Asn Asp Asp Lys Val Asn
                325                 330                 335

His Thr Asn Asp Asp Lys Val Asn His Thr Asn Asp Asp Lys Val Asn
            340                 345                 350

His Thr Asn Asp Asp Lys Val Asn His Thr Asn Asp Asp Lys Val Asn
        355                 360                 365

His Thr Asn Asp Asp Lys Val Asn His Thr Asn Asp Asp Lys Val Asn
    370                 375                 380

His Thr Asn Asn Tyr Tyr Asn Asp Lys Lys Asn Asn Ala Gly Asp Ile
385                 390                 395                 400

Lys Thr Asn Asn Ser Ile Arg Glu Glu Lys Lys Leu Glu His Pro Asp
                405                 410                 415

Arg Asn Ile Glu Lys Lys Ile Asp Leu Ile Thr Tyr Asn Lys Lys Arg
            420                 425                 430

Ile Glu Glu Tyr Tyr Asp Ser Ile Ser Tyr Phe Phe Gly Leu Ile
        435                 440                 445

Ile Leu Tyr His Asn Lys Lys Glu Thr Asn Leu Asn Tyr Tyr Thr Lys
    450                 455                 460

Phe Leu Thr Leu Asp Lys Tyr Lys Asn Met Tyr Asn Cys Leu Asn Asn

```
                465                 470                 475                 480
Asp Ile Ser Lys Ile Tyr Glu Lys Ala Ile Leu Phe Ser His Glu Glu
                    485                 490                 495

Phe Cys Ile Ile Gln Lys Lys Asp Leu Lys Pro His Gly Leu Arg Gly
                500                 505                 510

Asn Ile Lys Tyr Tyr Tyr Phe Phe Asn Arg Ile Val Ser Thr Ser Leu
            515                 520                 525

Tyr Leu Leu His Glu Ile Leu Gln Lys Leu Asp Gly Lys Met Tyr Thr
        530                 535                 540

Phe Gln Lys Leu Pro Leu Lys Ile Gln Asn His Leu Ile Asn Leu Pro
545                 550                 555                 560

Asp Ile Arg Ile Lys Glu Ile Lys Lys Arg Met Arg Gln Lys Lys
                565                 570                 575

Lys Asn Gln Asn Ser Leu Leu Glu Ser Ser Ser Tyr Lys Asp Leu Tyr
                580                 585                 590

Tyr Val Ser Ser Glu Tyr Tyr Asp Tyr Val Ser Lys Cys Leu Ile Trp
            595                 600                 605

Ser Asn Tyr Tyr Phe Phe Asn Tyr Met Ser Thr Thr Ile Val Tyr Ser
        610                 615                 620

Val Lys Lys Arg Ser Tyr Glu Tyr Ile Gln Lys Glu Lys Ser Lys Ile
625                 630                 635                 640

Asn Leu Phe Leu Glu Tyr Ala His Asn Asp Ile Ile Glu Tyr Ile Lys
                645                 650                 655

Asp Ile Thr Tyr Tyr Phe Lys Leu Ile Val Asn Lys Ile Glu Ser Lys
            660                 665                 670

Arg Leu Phe Ser Glu Pro Val Met Leu Cys Phe Gln Leu Phe Ser Asp
        675                 680                 685

His Tyr Leu Tyr Leu Leu Lys Asn Ile Leu Ser Ile Leu Leu Ile His
        690                 695                 700

Ile Glu Lys Pro Val Thr Arg Lys Ser Asn Arg Asp Leu Lys Lys Ile
705                 710                 715                 720

Phe Asn Cys Ile Lys Asp Gln Glu Asn Ile Thr Lys Asn Ile Leu Asp
                725                 730                 735

Glu Phe His Ser Lys Asn Lys Ile Arg Tyr Asn Pro Thr Glu Phe Leu
            740                 745                 750

Ile Tyr Lys Phe Phe Ser Ser Ile Gln Tyr Lys Gln Asn Ile Ala His
        755                 760                 765

Lys Tyr Ile Ile Gln Ser Asn Ile Asn Ile Ser Leu Met Leu Lys
        770                 775                 780

Ile Phe Asn Tyr Phe His Ile Leu Val Ile Ser Leu Ile Phe Tyr Leu
785                 790                 795                 800

Asn Leu His Ser Met Tyr Thr Leu Phe Ile Asp Leu Asp Ile Asp Asp
                805                 810                 815

Thr Leu Lys Phe Gln His Asp Gln Glu Phe Leu Asn Tyr Phe Lys Arg
            820                 825                 830

Tyr Gln Asp Phe Asn Asn Gln Leu Phe Asp Ser Phe Arg Ser Asp Asp
        835                 840                 845

Arg

<210> SEQ ID NO 5
<211> LENGTH: 865
<212> TYPE: PRT
<213> ORGANISM: Plasmodium falciparum
```

<400> SEQUENCE: 5

```
Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile Ile Ala Glu Tyr Cys Asp Thr Lys Lys Asn Glu Phe
        35                  40                  45

Phe Leu Gly Glu Ser Ile Leu Gly Ala Thr Ser Ser Arg Ser Thr Ser
    50                  55                  60

Leu Asn Ile Glu Gln Asn Lys Asn Thr Asn Ile Ile Lys Asp Lys Asn
65                  70                  75                  80

Glu Gln Ser Tyr Asp Glu His Ile Val Met Asn Pro Asn Thr Asn Arg
                85                  90                  95

Ala Leu Ser Ile Asn Thr Val Phe Asn Tyr Asn Lys Glu Asn Lys Glu
            100                 105                 110

Lys Lys Ile Phe Ser Phe Ser Glu Phe Pro Lys Glu Phe Asn Ile Leu
        115                 120                 125

Asp Val Val Trp Pro Tyr Met Lys Gln Pro Lys Glu Leu Phe Lys Lys
    130                 135                 140

Ser Ser Val Ile Thr Phe Leu Met Asp His Tyr Phe Arg His Glu Leu
145                 150                 155                 160

Tyr Ile Leu Glu Ser Arg Ile Ala Met Lys Pro Arg Arg Arg Thr Tyr
                165                 170                 175

Glu Ala Pro Cys Phe Glu His Asp Asp Phe Glu Leu Glu Arg Asp Phe
            180                 185                 190

Phe Phe Leu Glu Asp Cys Asp Glu Asp His Gln Phe Phe Asn Lys Tyr
        195                 200                 205

Lys Ser Tyr Phe Phe Ser Leu Asn Val Leu Asp His Cys Lys Ser Leu
    210                 215                 220

Arg Thr Lys Lys Gln Lys Cys Asn Asn Met Lys Asp Asp Glu Val Ser
225                 230                 235                 240

Asn Ile Asn Asp Asp Glu Val Ser Asn Ile Lys Asp Asp Glu Val Ser
                245                 250                 255

Asn Ile Lys Asp Asp Val Val Arg Asn Ile Asn Asp Asp Val Val Arg
            260                 265                 270

Asn Ile Asn Asp Asp Val Val Arg Asn Ile Asn Asp Asp Glu Val His
        275                 280                 285

His Thr Asn Asp Asp Asn Val Asn His Thr Asn Asp Asp Lys Val Asn
    290                 295                 300

His Thr Asn Asp Asp Lys Val Asn His Thr Asn Asp Asp Lys Val Asn
305                 310                 315                 320

His Thr Asn Asp Asp Lys Val Asn His Thr Asn Asp Asp Lys Val Asn
                325                 330                 335

His Thr Asn Asp Asp Lys Val Asn His Thr Asn Asp Asp Lys Val Asn
            340                 345                 350

His Thr Asn Asp Asp Lys Val Asn His Thr Asn Asp Asp Lys Val Asn
        355                 360                 365

His Thr Asn Asp Asp Asn Val Asn His Thr Asn Asp Asp Lys Val Asn
    370                 375                 380

His Thr Asn Asp Asp Lys Val Asn His Thr Asn Asp Asp Lys Val Asn
385                 390                 395                 400

His Thr Asn Asn Tyr Tyr Asn Asp Lys Lys Asn Asn Ala Gly Asp Ile
                405                 410                 415
```

-continued

```
Lys Thr Asn Asn Ser Ile Arg Glu Glu Lys Lys Leu Glu His Pro Asp
                420                 425                 430

Arg Asn Ile Glu Lys Lys Ile Asp Leu Ile Thr Tyr Asn Lys Lys Arg
            435                 440                 445

Ile Glu Glu Tyr Tyr Asp Ser Ile Ile Ser Tyr Phe Phe Gly Leu Ile
450                 455                 460

Ile Leu Tyr His Lys Lys Lys Glu Thr Asn Leu Asn Tyr Tyr Thr Lys
465                 470                 475                 480

Phe Leu Thr Leu Asp Lys Tyr Lys Asn Met Tyr Asn Cys Leu Asn Asn
                485                 490                 495

Asp Ile Ser Lys Ile Tyr Glu Lys Ala Ile Leu Phe Ser His Glu Glu
                500                 505                 510

Phe Cys Ile Ile Gln Lys Lys Asp Leu Lys Pro His Gly Leu Arg Gly
            515                 520                 525

Asn Ile Lys Tyr Tyr Phe Phe Asn Arg Ile Val Ser Thr Ser Leu
            530                 535                 540

Tyr Leu Leu His Glu Ile Leu Gln Lys Leu Asp Gly Lys Met Tyr Thr
545                 550                 555                 560

Phe Gln Lys Leu Pro Leu Lys Ile Gln Asn His Leu Ile Asn Leu Pro
                565                 570                 575

Asp Ile Arg Ile Lys Glu Ile Lys Lys Arg Met Arg Gln Gln Lys Lys
                580                 585                 590

Lys Asn Lys Asn Ser Leu Leu Glu Ser Ser Tyr Lys Asp Leu Tyr
            595                 600                 605

Tyr Val Ser Ser Glu Tyr Tyr Asp Tyr Val Ser Lys Cys Leu Ile Trp
            610                 615                 620

Ser Asn Tyr Tyr Phe Phe Asn Tyr Met Ser Thr Thr Ile Val Tyr Ser
625                 630                 635                 640

Val Lys Lys Arg Ser Tyr Glu Tyr Ile Gln Lys Glu Lys Ser Lys Ile
                645                 650                 655

Asn Leu Phe Leu Glu Tyr Ala His Asn Asp Ile Ile Glu Tyr Ile Lys
                660                 665                 670

Asp Ile Thr Tyr Tyr Phe Lys Leu Ile Val Asn Lys Ile Glu Ser Lys
            675                 680                 685

Arg Leu Phe Ser Glu Pro Val Met Leu Cys Phe Gln Leu Phe Ser Asp
690                 695                 700

His Tyr Leu Tyr Leu Leu Lys Asn Ile Leu Ser Ile Leu Leu Ile His
705                 710                 715                 720

Ile Glu Lys Pro Val Thr Arg Lys Ser Asn Arg Asp Leu Lys Lys Ile
                725                 730                 735

Phe Asn Cys Ile Lys Asp Gln Gly Asn Ile Thr Lys Asn Ile Leu Asp
            740                 745                 750

Glu Phe His Ser Lys Asn Lys Ile Arg Tyr Asn Pro Thr Glu Phe Leu
                755                 760                 765

Ile Tyr Lys Phe Phe Ser Ser Ile Gln Tyr Lys Gln Asn Ile Ala His
770                 775                 780

Lys Tyr Ile Ile Gln Ser Asn Ile Asn Ile Ile Ser Leu Met Leu Lys
785                 790                 795                 800

Ile Phe Asn Tyr Phe His Ile Leu Val Ile Ser Leu Ile Phe Tyr Leu
                805                 810                 815

Asn Leu His Ser Met Tyr Thr Leu Phe Ile Asp Leu Asp Ile Asp Asp
            820                 825                 830
```

```
Thr Leu Lys Phe Gln His Asp Gln Glu Phe Leu Asn Tyr Phe Lys Arg
            835                 840                 845

Tyr Gln Asp Phe Asn Asn Gln Leu Phe Asp Ser Phe Arg Ser Asp Asp
850                 855                 860

Arg
865

<210> SEQ ID NO 6
<211> LENGTH: 884
<212> TYPE: PRT
<213> ORGANISM: Plasmodium falciparum

<400> SEQUENCE: 6

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile Ile Ala Glu Tyr Cys Asp Thr Lys Lys Asn Glu Phe
        35                  40                  45

Phe Leu Gly Glu Ser Ile Leu Gly Ala Thr Ser Ser Arg Ser Thr Ser
    50                  55                  60

Leu Asn Ile Glu Gln Asn Lys Asn Thr Asn Ile Ile Lys Asp Lys Asn
65                  70                  75                  80

Glu Gln Ser Tyr Asp Glu His Ile Val Met Asn Pro Asn Thr Asn Arg
                85                  90                  95

Ala Leu Ser Ile Asn Thr Val Phe Asn Tyr Asn Lys Glu Asn Lys Glu
            100                 105                 110

Lys Lys Ile Phe Ser Phe Ser Glu Phe Pro Lys Glu Phe Asn Ile Leu
        115                 120                 125

Asp Val Val Trp Pro Tyr Met Lys Gln Pro Lys Glu Leu Phe Lys Lys
    130                 135                 140

Ser Ser Val Ile Thr Phe Leu Met Asp His Tyr Phe Arg His Glu Leu
145                 150                 155                 160

Tyr Ile Leu Glu Ser Arg Ile Ala Met Lys Pro Arg Arg Arg Thr Tyr
                165                 170                 175

Glu Ala Pro Cys Phe Glu His Asp Asp Phe Glu Leu Glu Arg Asp Phe
            180                 185                 190

Phe Phe Leu Glu Asp Cys Asp Glu Asp His Gln Phe Phe Asn Lys Tyr
        195                 200                 205

Lys Ser Tyr Phe Phe Ser Leu Asn Val Leu Asp His Cys Lys Ser Leu
    210                 215                 220

Arg Thr Lys Lys Gln Lys Cys Asn Asn Met Lys Asp Asp Glu Val Ser
225                 230                 235                 240

Asn Ile Asn Asp Asp Glu Val Ser Asn Ile Asn Asp Asp Glu Val Ser
                245                 250                 255

Asn Ile Lys Asp Asp Val Val Arg Asn Ile Asn Asp Asp Val Val Arg
            260                 265                 270

Asn Ile Asn Asp Asp Val Val Arg Asn Ile Asn Asp Asp Glu Val His
        275                 280                 285

His Thr Asn Asp Asp Asn Val Asn His Thr Asn Asp Asp Lys Val Asn
    290                 295                 300

His Thr Asn Asp Asp Lys Val Asn His Thr Asn Asp Asp Lys Val Asn
305                 310                 315                 320

His Thr Asn Asp Asp Asn Val Asn His Thr Asn Asp Asp Lys Val Asn
                325                 330                 335
```

```
His Thr Asn Asp Asp Asn Val Asn His Thr Asn Asp Asp Lys Val Asn
            340                 345                 350

His Thr Asn Asp Asp Lys Val Asn His Thr Asn Asp Asp Asn Val Asn
            355                 360                 365

His Thr Asn Asp Asp Lys Val Asn His Thr Asn Asp Asp Lys Val Asn
            370                 375                 380

His Thr Asn Asp Asp Lys Val Asn His Thr Asn Asp Asp Lys Val Asn
385                 390                 395                 400

His Thr Asn Asp Asp Lys Val Asn His Thr Asn Asp Asp Lys Val Asn
                405                 410                 415

His Thr Asn Asp Asp Lys Val Asn His Thr Asn Asp Asp Lys Val Asn
                420                 425                 430

His Thr Asn Asn Tyr Tyr Asn Asp Lys Lys Asn Asn Ala Gly Asp Ile
                435                 440                 445

Lys Thr Asn Asn Ser Ile Arg Glu Glu Lys Lys Leu Glu His Pro Asp
            450                 455                 460

Arg Asn Ile Glu Lys Glu Asp Arg Phe Asn Tyr Ile Lys Lys Asp Arg
465                 470                 475                 480

Arg Ile Leu Gln Tyr Asn Phe Ile Phe Phe Arg Ile Asn Asn Ile Ile
                485                 490                 495

Ser Lys Glu Thr Asn Leu Asn Tyr Tyr Thr Lys Leu Leu Thr Leu Asp
            500                 505                 510

Lys Tyr Lys Asn Met Tyr Asn Cys Leu Asn Asn Asp Ile Ser Lys Ile
                515                 520                 525

Tyr Glu Lys Ala Ile Leu Phe Phe Thr Arg Val Leu Tyr Ile Gln Lys
            530                 535                 540

Lys Ile Lys Ser Ser Trp Ile Glu Ser Gln Tyr Lys Ile Leu Leu Phe
545                 550                 555                 560

Phe Ser Tyr Cys His Ile Phe Ile Phe Val Thr Asn Ile Thr Lys Ile
                565                 570                 575

Arg Trp Thr Asp Val Tyr Leu Ser Glu Ile Thr Ile Lys Asp Thr Glu
            580                 585                 590

Ser Phe Asn Ser Ser Gly Tyr Lys Asn Gln Glu Asn Lys Thr Tyr Glu
            595                 600                 605

Thr Thr Glu Lys Lys Glu Asn Ser Leu Leu Glu Ser Ser Ser Tyr Lys
            610                 615                 620

Asp Leu Tyr Tyr Val Ser Ser Glu Tyr Tyr Asp Tyr Val Ser Lys Cys
625                 630                 635                 640

Leu Ile Trp Ser Asn Tyr Tyr Phe Phe Asn Tyr Met Ser Thr Thr Ile
                645                 650                 655

Val Tyr Ser Val Lys Lys Arg Ser Tyr Glu Tyr Ile Glu Lys Glu Lys
            660                 665                 670

Ser Lys Ile Asn Leu Phe Leu Glu Tyr Ala His Asn Asp Ile Ile Glu
            675                 680                 685

Tyr Ile Lys Asp Ile Thr Tyr Tyr Phe Lys Leu Ile Val Asn Lys Ile
            690                 695                 700

Glu Ser Lys Arg Leu Phe Ser Glu Pro Val Met Leu Cys Phe Gln Leu
705                 710                 715                 720

Phe Ser Asp His Tyr Leu Tyr Leu Leu Lys Asn Ile Leu Ser Ile Leu
                725                 730                 735

Leu Ile His Ile Glu Lys Pro Val Thr Arg Lys Ser Asn Arg Asp Leu
            740                 745                 750
```

-continued

```
Lys Lys Ile Phe Asn Cys Ile Lys Asp Gln Glu Asn Ile Thr Lys Asn
            755                 760                 765

Ile Leu Asp Glu Phe His Ser Lys Asn Lys Ile Arg Tyr Asn Pro Thr
        770                 775                 780

Glu Phe Leu Ile Tyr Lys Phe Ser Ser Ile Gln Tyr Lys Gln Asn
785                 790                 795                 800

Ile Ala His Lys Tyr Ile Ile Gln Ser Asn Ile Asn Ile Ile Ser Leu
                805                 810                 815

Met Leu Lys Ile Phe Asn Tyr Phe His Ile Leu Val Ile Ser Leu Ile
            820                 825                 830

Phe Tyr Leu Asn Leu His Ser Met Tyr Thr Leu Phe Ile Asp Leu Asp
            835                 840                 845

Ile Asp Asp Thr Leu Lys Phe Gln His Asp Gln Glu Phe Leu Asn Tyr
        850                 855                 860

Phe Lys Arg Tyr Gln Asp Phe Asn Asn Gln Leu Phe Asp Ser Phe Arg
865                 870                 875                 880

Ser Asp Asp Arg

<210> SEQ ID NO 7
<211> LENGTH: 16
<212> TYPE: PRT
<213> ORGANISM: Plasmodium falciparum

<400> SEQUENCE: 7

Asp Asp Glu Val Ser Asn Ile Asn Asp Asp Glu Val Ser Asn Ile Asn
1               5                   10                  15

<210> SEQ ID NO 8
<211> LENGTH: 16
<212> TYPE: PRT
<213> ORGANISM: Plasmodium falciparum

<400> SEQUENCE: 8

Asp Asp Glu Val Ser Asn Ile Asn Asp Asp Glu Val Ser Asn Ile Lys
1               5                   10                  15

<210> SEQ ID NO 9
<211> LENGTH: 16
<212> TYPE: PRT
<213> ORGANISM: Plasmodium falciparum

<400> SEQUENCE: 9

Asp Asp Val Val Arg Asn Ile Asn Asp Asp Val Val Arg Asn Ile Asn
1               5                   10                  15

<210> SEQ ID NO 10
<211> LENGTH: 16
<212> TYPE: PRT
<213> ORGANISM: Plasmodium falciparum

<400> SEQUENCE: 10

Asp Asp Glu Val His His Thr Asn Asp Asp Lys Val Asn His Thr Asn
1               5                   10                  15

<210> SEQ ID NO 11
<211> LENGTH: 16
<212> TYPE: PRT
<213> ORGANISM: Plasmodium falciparum

<400> SEQUENCE: 11

Asp Asp Lys Val Asn His Thr Asn Asp Asp Lys Val Asn His Thr Asn
```

<210> SEQ ID NO 12
<211> LENGTH: 16
<212> TYPE: PRT
<213> ORGANISM: Plasmodium falciparum

<400> SEQUENCE: 12

Asp Asp Asn Val Asn His Thr Asn Asp Lys Val Asn His Thr Asn
1               5                   10                  15

<210> SEQ ID NO 13
<211> LENGTH: 18
<212> TYPE: PRT
<213> ORGANISM: Plasmodium falciparum

<400> SEQUENCE: 13

Met Tyr Lys Lys Cys Phe Ile Leu Tyr Pro Ile Phe Phe Pro Ser Leu
1               5                   10                  15

Tyr Ile

<210> SEQ ID NO 14
<211> LENGTH: 11
<212> TYPE: PRT
<213> ORGANISM: Plasmodium falciparum

<400> SEQUENCE: 14

Ser Phe Ser Arg Ile Ile Ala Glu Tyr Cys Asp
1               5                   10

<210> SEQ ID NO 15
<211> LENGTH: 23
<212> TYPE: PRT
<213> ORGANISM: Plasmodium falciparum

<400> SEQUENCE: 15

Tyr Phe His Ile Leu Val Ile Ser Leu Ile Phe Tyr Leu Asn Leu His
1               5                   10                  15

Ser Met Tyr Thr Leu Phe Ile
            20

<210> SEQ ID NO 16
<211> LENGTH: 39
<212> TYPE: PRT
<213> ORGANISM: Plasmodium falciparum

<400> SEQUENCE: 16

Asp Leu Asp Ile Asp Asp Thr Leu Lys Phe Gln His Asp Gln Glu Phe
1               5                   10                  15

Leu Asn Tyr Phe Lys Arg Tyr Gln Asp Phe Asn Asn Gln Leu Phe Asp
            20                  25                  30

Ser Phe Arg Ser Asp Asp Arg
            35

<210> SEQ ID NO 17
<211> LENGTH: 20
<212> TYPE: PRT
<213> ORGANISM: Plasmodium falciparum

<400> SEQUENCE: 17

Leu Lys Phe Gln His Asp Gln Glu Phe Leu Asn Tyr Phe Lys Arg Tyr
1               5                   10                  15

Gln Asp Phe Asn
            20

<210> SEQ ID NO 18
<211> LENGTH: 23
<212> TYPE: PRT
<213> ORGANISM: Plasmodium falciparum

<400> SEQUENCE: 18

Val Met Asn Pro Asn Thr Asn Arg Ala Leu Ser Ile Asn Thr Val Phe
1               5                   10                  15

Asn Tyr Asn Lys Glu Asn Lys
            20

<210> SEQ ID NO 19
<211> LENGTH: 23
<212> TYPE: PRT
<213> ORGANISM: Plasmodium falciparum

<400> SEQUENCE: 19

Leu Asn Tyr Tyr Thr Lys Phe Leu Thr Leu Asp Lys Tyr Lys Asn Met
1               5                   10                  15

Tyr Asn Cys Leu Asn Asn Asp
            20

<210> SEQ ID NO 20
<211> LENGTH: 20
<212> TYPE: PRT
<213> ORGANISM: Plasmodium falciparum

<400> SEQUENCE: 20

Pro His Gly Leu Arg Gly Asn Ile Lys Tyr Tyr Tyr Phe Phe Asn Arg
1               5                   10                  15

Ile Val Ser Thr
            20

<210> SEQ ID NO 21
<211> LENGTH: 25
<212> TYPE: PRT
<213> ORGANISM: Plasmodium falciparum

<400> SEQUENCE: 21

Asn Tyr Tyr Phe Phe Asn Tyr Met Ser Thr Thr Ile Val Tyr Ser Val
1               5                   10                  15

Lys Lys Arg Ser Tyr Glu Tyr Ile Gln
            20                  25

<210> SEQ ID NO 22
<211> LENGTH: 31
<212> TYPE: PRT
<213> ORGANISM: Plasmodium falciparum

<400> SEQUENCE: 22

Asp Ile Thr Tyr Tyr Phe Lys Leu Ile Val Asn Lys Ile Glu Ser Lys
1               5                   10                  15

Arg Leu Phe Ser Glu Pro Val Met Leu Cys Phe Gln Leu Phe Ser
            20                  25                  30

<210> SEQ ID NO 23
<211> LENGTH: 23
<212> TYPE: PRT
<213> ORGANISM: Plasmodium falciparum

```
<400> SEQUENCE: 23

Ser Lys Asn Lys Ile Arg Tyr Asn Pro Thr Glu Phe Leu Ile Tyr Lys
1               5                   10                  15

Phe Phe Ser Ser Ile Gln Tyr
            20

<210> SEQ ID NO 24
<211> LENGTH: 13
<212> TYPE: PRT
<213> ORGANISM: Plasmodium falciparum

<400> SEQUENCE: 24

Asp Asp Asn Val Asn His Thr Asn Asp Lys Val Asn
1               5                   10

<210> SEQ ID NO 25
<211> LENGTH: 24
<212> TYPE: PRT
<213> ORGANISM: Plasmodium falciparum

<400> SEQUENCE: 25

Asp Asp Lys Val Asn His Thr Asn Asp Asn Val Asn His Thr Asn
1               5                   10                  15

Asp Asp Lys Val Asn His Thr Asn
            20

<210> SEQ ID NO 26
<211> LENGTH: 19
<212> TYPE: PRT
<213> ORGANISM: Plasmodium falciparum

<400> SEQUENCE: 26

Asp Asp Asn Val Asn His Thr Asn Asp Lys Val Asn His Thr Asn
1               5                   10                  15

Asp Asp Lys

<210> SEQ ID NO 27
<211> LENGTH: 20
<212> TYPE: PRT
<213> ORGANISM: Plasmodium falciparum

<400> SEQUENCE: 27

Gly Glu Ser Ile Leu Gly Ala Thr Ser Ser Arg Ser Thr Ser Leu Asn
1               5                   10                  15

Ile Glu Gln Asn
            20

<210> SEQ ID NO 28
<211> LENGTH: 36
<212> TYPE: PRT
<213> ORGANISM: Plasmodium falciparum

<400> SEQUENCE: 28

Met Tyr Lys Lys Cys Phe Ile Leu Tyr Pro Ile Phe Phe Pro Ser Leu
1               5                   10                  15

Tyr Ile Tyr Ile Ile Lys Asn Asp His Leu Asn Ser Glu Gln Ser Ser
            20                  25                  30

Phe Ser Arg Ile
        35

<210> SEQ ID NO 29
```

```
<211> LENGTH: 72
<212> TYPE: DNA
<213> ORGANISM: Plasmodium falciparum

<400> SEQUENCE: 29
aaaaagcagg cttcgaagga gatagaacca tgatgtataa gaaatgtttc attttatatc    60 ctatctttt tc                                                         72

<210> SEQ ID NO 30
<211> LENGTH: 40
<212> TYPE: DNA
<213> ORGANISM: Plasmodium falciparum

<400> SEQUENCE: 30
agaaagctgg gtctcatctg tcgtcggaac ggaaggaatc                          40

<210> SEQ ID NO 31
<211> LENGTH: 56
<212> TYPE: DNA
<213> ORGANISM: Plasmodium falciparum

<400> SEQUENCE: 31
aaaaagcagg cttcgattta gatattgatg atactttaaa gtttcagcat gatcaa        56

<210> SEQ ID NO 32
<211> LENGTH: 40
<212> TYPE: DNA
<213> ORGANISM: Plasmodium falciparum

<400> SEQUENCE: 32
agaaagctgg gtctcatctg tcgtcggaac ggaaggaatc                          40

<210> SEQ ID NO 33
<211> LENGTH: 47
<212> TYPE: DNA
<213> ORGANISM: Plasmodium falciparum

<400> SEQUENCE: 33
aaaaagcagg cttcgatgat gtggtgagaa atattaacga tgatgtg                  47

<210> SEQ ID NO 34
<211> LENGTH: 64
<212> TYPE: DNA
<213> ORGANISM: Plasmodium falciparum

<400> SEQUENCE: 34
agaaagctgg gtctcaacta ttattagttt ttatatcacc tgcattattc tttttatcat    60
tata                                                                 64

<210> SEQ ID NO 35
<211> LENGTH: 48
<212> TYPE: DNA
<213> ORGANISM: Plasmodium falciparum

<400> SEQUENCE: 35
aaaaagcagg cttcggaaaa agaaaaggat attacctagc aaaaaaac                 48

<210> SEQ ID NO 36
<211> LENGTH: 46
<212> TYPE: DNA
<213> ORGANISM: Plasmodium falciparum

<400> SEQUENCE: 36
```

```
agaaagctgg gtcttaaggt ttctctagca actgtttttg ttgtgg                    46

<210> SEQ ID NO 37
<211> LENGTH: 23
<212> TYPE: DNA
<213> ORGANISM: Plasmodium falciparum

<400> SEQUENCE: 37
gctctttcca taaatactgt att                                             23

<210> SEQ ID NO 38
<211> LENGTH: 17
<212> TYPE: DNA
<213> ORGANISM: Plasmodium falciparum

<400> SEQUENCE: 38
atggccaaac aacatca                                                    17

<210> SEQ ID NO 39
<211> LENGTH: 17
<212> TYPE: DNA
<213> ORGANISM: Plasmodium falciparum

<400> SEQUENCE: 39
acaattggag ggcaagt                                                    17

<210> SEQ ID NO 40
<211> LENGTH: 17
<212> TYPE: DNA
<213> ORGANISM: Plasmodium falciparum

<400> SEQUENCE: 40
ttggagctgg aattacc                                                    17

<210> SEQ ID NO 41
<211> LENGTH: 2502
<212> TYPE: DNA
<213> ORGANISM: Plasmodium falciparum

<400> SEQUENCE: 41
atgtataaga aatgttttcat tttatatcct atctttttttc cctccttata tatttatatt    60
attaagaatg atcatttgaa ctcagaacaa agttcattct caagaataat agcagaatac    120
tgtgatacaa aaaaaaatga atttttttttg ggggaatcta ttttaggtgc tacatcctca   180
agaagcactt ctcttaacat agaacagaat aaaaacacaa atattattaa agataagaat   240
gaacaaagtt atgatgaaca tattgtaatg aatccaaata ccaatcgagc tctttccata   300
aatactgtat tcaattacaa taagaaaaat aaggaaaaaa aattttttc cttctccgaa    360 tttccaaagg aatttaatat acttgatgtt gtttggccat acatgaaaca acctaaagaa   420 cttttttaaaa aatcatctgt aatcactttt ttaatggacc attattttag acatgaacta   480
tatattttag aaagtagaat tgcaatgaaa ccaagaagga gaacatatga agctccatgt   540
tttgaacatg atgattttga attagaaaga gatttttttt ttttagaaga ctgtgatgaa   600
gatcatcaat tttttaataa atacaaaagt tattttttttt cgttgaatgt actagatcat   660
tgtaaaagtt taaggactaa gaagcagaaa tgtaataata tgaaggatga tgaggtgagc   720
aatattaacg atgatgaagt gagcaatatt aacgatgatg aagtgagcaa tattaacgat   780
gatgaagtga gcaatataaa agatgatgtg gtgagaaata ttaacgatga tgtggtgaga   840
```

```
aatattaacg atgatgaggt gcaccataca aatgatgata aggtgaacca tacaaatgat    900
gataaggtga accatacgaa tgatgataag gtgaaccata cgaatgatga taaggtgaac    960
catacaaatg atgataaggt gaaccataca aatgacgata atgtgaacca tacaaatgat   1020
gataaggtga accatacaaa tgacgataag gtgaaccata caaatgacga taaggtgaac   1080
catacaaatg acgataaggt gaaccataca aataattatt ataatgataa aaagaataat   1140
gcaggtgata taaaaactaa taatagtata cgtgaggaaa aaaaactaga gcacccggac   1200
aggaacattg aaaagaagat cgatttaatt acatataata aaaaaaggat agaagaatat   1260
tatgacagta taatttcata tttttcgga ttaataatat tatatcataa taaaaaagag    1320
acgaatctaa attattacac aaaatttta acattagata aatataagaa tatgtataat    1380
tgtttaaata atgatatatc taaaatatat gaaaaagcaa tattattttc acatgaagag   1440
ttttgtataa tacagaaaaa agatttaaaa cctcatggtt tgagaggtaa tataaaatat   1500
tattattttt ttaatcgtat tgttagcaca tctttatatt tgttacatga aatattacaa   1560
aaattagatg gaaagatgta taccttcag aaattaccat taaagataca gaatcattta    1620
attaatcttc cggatataag aatcaaggaa attaaaaaac gtatgagaca acagaaaaaa   1680
aagaatcaaa attctctttt agaaagtagt agttataaag atttatatta tgtatctagt   1740
gaatattatg attatgttag taagtgttta atatggtcta attattattt ttttaattat   1800
atgtctacca ctatagtata tagtgttaaa aaaagaagct atgaatatat acaaaaagaa   1860
aaatccaaaa taaatttatt tttagaatat gcacataatg atattataga atatataaaa   1920
gacataacat attatttaa attaattgtt aataaaatag aatcaaaacg cttattctct    1980
gaacccgtaa tgttatgctt tcaactgttt tctgatcatt atttatattt actcaaaaat   2040
atattatcta tacttttaat acatatagaa aaaccagtta caagaaaatc aaacagagat   2100
ctaaaaaaaa tatttaattg tataaaagat caagaaaata taaccaaaaa tatttagat    2160 gaattccatt ccaaaaataa aattagatat aatccaaccg aattcctcat atataaattt   2220
ttttcaagta acaatataa acaaaatata gcacataaat atataataca aagtaatatt    2280
aatattatat ccttgatgtt gaaaattttt aattattttc atatacttgt tatctcatta   2340 atctttatc taaaccttca ttctatgtat actctattta ttgatttaga tattgatgat    2400
actttaaagt ttcagcatga tcaagagttc ttaaattatt ttaaaagata tcaggattt    2460 aataatcaac tctttgattc cttccgttcc gacgacagat ga                     2502
```